(12) United States Patent
Piwnica-Worms et al.

(10) Patent No.: US 7,442,518 B2
(45) Date of Patent: Oct. 28, 2008

(54) IMAGING REGULATED PROTEIN-PROTEIN INTERACTIONS IN CELLS AND LIVING ANIMALS BY ENHANCED LUCIFERASE PROTEIN FRAGMENT COMPLEMENTATION

(75) Inventors: David Piwnica-Worms, Laduc, MO (US); Kathryn Luker, Ann Arbor, MI (US); Gary Luker, Ann Arbor, MI (US)

(73) Assignee: Washington University, St. Louis, MO (US)

( * ) Notice: Subject to any disclaimer, the term of this patent is extended or adjusted under 35 U.S.C. 154(b) by 224 days.

(21) Appl. No.: 10/912,862

(22) Filed: Aug. 6, 2004

(65) Prior Publication Data

US 2005/0144661 A1      Jun. 30, 2005

Related U.S. Application Data

(60) Provisional application No. 60/492,920, filed on Aug. 6, 2003.

(51) Int. Cl.
*C12Q 1/66* (2006.01)
*G01N 33/53* (2006.01)
*C12N 15/62* (2006.01)

(52) U.S. Cl. .............................. 435/8; 435/7.1; 435/7.6; 435/7.8; 435/189; 435/320.1; 536/23.4

(58) Field of Classification Search ....................... None
See application file for complete search history.

(56) References Cited

OTHER PUBLICATIONS

R. Paulmurugan et al. . "Noninvasive imaging of protein-protein interactions in living subjects by using reporter protein complementation and reconstitution strategies". Proc Natl Acad Sci. 99(24): 15608-5613 (Nov. 18, 2002).*

* cited by examiner

*Primary Examiner*—Rebecca E. Prouty
(74) *Attorney, Agent, or Firm*—Armstrong Teasdale LLP

(57) ABSTRACT

An enhanced firefly luciferase protein fragment complementation assay method is described that produces a robust and broadly applicable bioluminescence signal and demonstrates both modification-independent and phosphorylation-dependent protein interactions in intact living human cells and animals useful as a diagnostic and testing tool in living biologic systems in research and in assays.

7 Claims, 16 Drawing Sheets

IMAGING REGULATED PROTEIN-PROTEIN INTERACTIONS IN CELLS AND LIVING ANIMALS BY ENHANCED LUCIFERASE PROTEIN FRAGMENT COMPLEMENTATION

This application claims the benefit of U.S. Provisional Patent Application Ser. No. 60/492,920, filed Aug. 6, 2003 which is incorporated herein in its entirety by reference.

STATEMENT REGARDING FEDERALLY SPONSORED RESEARCH AND DEVELOPMENT

This work was funded by National Institutes of Health grant P50 CA94056. The government may have certain rights in this discovery.

FIELD OF THE INVENTION

This discovery relates generally to a method of detecting protein-protein interactions. More particularly this discovery relates to an enhanced method of detecting protein to protein interactions in living systems.

A portion of the disclosure of this patent document contains material which is subject to copyright protection. The copyright owner has no objection to the facsimile reproduction by anyone of the patent document or the patent disclosure, as it appears in the U.S. Patent and Trademark Office patent file or records, but otherwise reserves all copyright rights whatsoever.

BACKGROUND OF THE INVENTION

Protein-protein interactions are fundamental to all living systems. Dynamic association and dissociation of protein complexes control most cellular functions, including cell cycle progression, signal transduction, and metabolic pathways. Complexes of transcription factors, co-repressors, and chromatin-binding proteins maintain normal cells in a quiescent state, and disruption of these protein interactions may be significant in permitting unregulated growth of cancer cells (1).

On a whole organism scale, protein-protein interactions regulate signals that affect overall homeostasis, patterns of development, normal physiology and disease in living animals. Examples include homo- and hetero-dimers of different homeobox proteins that control limb bud and craniofacial development (2), and interactions among various cell surface receptors, scaffold proteins, and transcription factors that regulate activation and trafficking of immune cells (3).

Additionally, protein interactions in signaling pathways have emerged as important therapeutic targets for cancer and other human diseases (4, 5). However, these pathways of protein interactions in specific tissues produce regional effects that cannot be investigated fully with in vitro systems and thus, there is considerable interest in imaging protein-protein interactions noninvasively in their normal physiological context within living animals with positron emission tomography (PET) (6, 7) or bioluminescence imaging (8, 9).

Regulated protein-protein interactions are fundamental to living systems, mediating many cellular functions, including cell cycle progression, signal transduction, and metabolic pathways (1, 2). In cancer, aberrant patterns of protein interactions arise from dysregulated phosphorylation of receptor tyrosine kinases (e.g., EGFR, Erb2/HER2), tumor suppressors (e.g., p53, PTEN) and targets that mediate downstream signaling in cell proliferation, survival and growth (e.g., STATs, mTOR, PI3K-Akt) (3). Thus, protein kinases and mediated protein-protein interactions comprising the kinome have emerged as important therapeutic targets in cancer and other human diseases (3-6). However, many protein interactions arise from host-cell interactions in tissue-specific pathways that cannot be investigated fully with in vitro systems and thus, there is considerable interest in imaging protein-protein interactions noninvasively in their normal physiological context within living animals with positron emission tomography (PET) (7, 8) or bioluminescence imaging (9, 10).

Current strategies for detecting protein-protein interactions include activation of transcription, repression of transcription, activation of signal transduction pathways or reconstitution of a disrupted enzymatic activity (8, 11, 12). In particular, protein fragment complementation depends on division of a monomeric enzyme into two separate components that do not spontaneously reassemble and function (13, 14). Enzyme activity occurs only upon complementation induced by the interaction of fused protein binding partners or by small molecules (drugs) that induce the interaction of fused proteins (FIG. 1). Of the available complementation strategies, feasibility studies with luciferase complementation have demonstrated the potential to observe protein-protein interactions in living animals (15, 16). However, available firefly luciferase fragments suffer from constitutive activity of the N-terminus fragment, while the blue-green emission spectrum of Renilla luciferase penetrates tissues poorly, thereby precluding general use. Furthermore, coelenterazine, the chromophoric substrate for Renilla luciferase, is transported by MDR1 P-glycoprotein (17), complicating applications of Renilla luciferase in vitro. Thus, no enzyme fragment pair yet has been found that satisfies all criteria for noninvasive analysis of protein-protein interactions and enables interrogation in cell lysates, intact cells and living animals.

Most strategies for detecting protein-protein interactions in intact cells are based on fusion of the pair of interacting molecules to defined protein elements to reconstitute a biological or biochemical function. Examples of reconstituted activities include activation of transcription, repression of transcription, activation of signal transduction pathways or reconstitution of a disrupted enzymatic activity (Toby and Golemis, 2001).

A variety of these techniques have been developed to investigate protein-protein interactions in cultured cells. The two-hybrid system is the most widely applied method to identify and characterize protein interactions. However, several features of protein fragment complementation make it attractive as an approach for in vivo imaging of protein interactions in cells, and particularly, in live animals. Below the inventors describe major features of these two methods and compare their potential utility for in vivo imaging in relation to other strategies based on our experience and published work.

Two-hybrid systems exploit the modular nature of transcription factors, many of which can be separated into discrete DNA-binding and activation domains (Fields and Song, 1989). Proteins of interest are expressed as fusions with either a DNA-binding domain (BD) or activation domain (AD), creating hybrid proteins. If the hybrid proteins bind to each other as a result of interaction between the proteins of interest, then the separate BD and AD of the transcription factor are brought together within the cell nucleus to drive expression of a reporter gene. In the absence of specific interaction between the hybrid proteins, the reporter gene is not expressed because the BD and AD do not associate independently. Two-hybrid assays can detect transient and/or unstable interactions between proteins, and the technique is reported to be independent of expression of endogenous proteins (von Mering et al., 2002).

Although the two-hybrid assay originally was developed in yeast, commercial systems (BD Biosciences Clontech) are now available for studies in bacteria and mammalian cells. The inventors and other investigators have shown that two-hybrid systems can be used to image protein interactions in living mice with positron emission tomography (PET) (Luker et al., 2002; Luker et al., 2003a; Luker et al., 2003c, b) or bioluminescence imaging (Ray et al., 2002). However, the two-hybrid method has some limitations. Some types of proteins do not lend themselves to study by the two-hybrid method. For example, because production of signal in the two-hybrid method requires nuclear localization of the hybrid proteins, membrane proteins cannot be studied in their intact state. Also, the time delay associated with both transcriptional activation of the reporter gene and degradation of the reporter protein and mRNA limits kinetic analysis of protein interactions (Rossi et al., 2000).

Protein-fragment complementation (PFC) assays depend on division of a monomeric reporter enzyme into two separate inactive components that can reconstitute function upon association. When these reporter fragments are fused to interacting proteins, the reporter is re-activated upon association of the interacting proteins. PFC strategies based on several enzymes, including β-galactosidase, dihydrofolate reductase (DHFR), β-lactamase, and luciferase have been used to monitor protein-protein interactions in mammalian cells (Rossi et al., 1997; Remy and Michnick, 1999; Remy et al., 1999; Ozawa et al., 2001; Galarneau et al., 2002; Wehrman et al., 2002).

A fundamental advantage of PFC is that the hybrid proteins directly reconstitute enzymatic activity of the reporter. In principle, therefore, protein interactions may be detected in any subcellular compartment, and assembly of protein complexes may be monitored in real time. A disadvantage of prior complementation approaches is that re-assembly of an enzyme may be susceptible to steric constraints imposed by the interacting proteins. Another potential limitation of PFC for application in living animals is that transient interactions between proteins may produce insufficient amounts of active enzyme to allow non-invasive detection. Nonetheless, because most PFC strategies are based on reconstituting active enzymes, these systems offer the potential benefits of signal amplification to enhance sensitivity for detecting interacting proteins in living animals.

The split-ubiquitin system enables signal amplification from a transcription factor-mediated reporter readout (Johnsson and Varshavsky, 1994; Stagljar et al., 1998). In one application, the interaction of two membrane proteins forces reconstitution of two halves of ubiquitin, leading to a cleavage event mediated by ubiquitin-specific proteases that release an artificial transcription factor to activate a reporter gene. As above, indirect readout of the reporter limits kinetic analysis, and the released transcription factor must translocate to the nucleus.

Several variations of recruitment systems have been developed for use in whole cells, including the Ras-recruitment system (Aronheim et al., 1997; Broder et al., 1998) and inter-action traps (Eyckerman et al., 2001). Cells that co-express a test protein fused to a membrane localization signal, such as a myristoylation sequence, and a protein binding partner fused to cytoplasmic protein, such as activated Ras devoid of its membrane targeting signal, will localize mammalian Ras to the membrane only in the presence of interacting proteins. However, Ras-recruitment systems, as originally configured, cannot be applied to mammalian cells, and, while readout is not directly dependent on transcriptional activation, indirect readout by colony growth nonetheless limits kinetic analysis and interrogation of subcellular compartmentation of the interactions.

A testing variation of the recruitment approach applicable to mammalian cells is the cytokine-receptor-based interaction trap. Here, a signaling-deficient receptor provides a scaffold for recruitment of interacting fusion proteins that phosphorylate endogenous STAT3. Activated STAT complexes then drive a nuclear reporter (Eyckerman et al., 2001). This system permits detection of both modification-independent and phosphorylation-dependent interactions in intact mammalian cells, but the transcriptional readout again limits kinetic analysis.

Other approaches to detecting protein-protein interactions in live mammalian cells include fluorescence resonance energy transfer (FRET) and bioluminescence resonance energy transfer (BRET) (Gautier et al., 2001; Boute et al., 2002). For FRET, fluorescently labeled proteins, one coupled to a donor fluorophore and the other coupled to an acceptor fluorophore, produce a characteristic shift in the emission spectra when the protein binding partners interact. A limitation of FRET is inter- and intra-molecular spatial constraints and sensitivity of detection since there is no amplification of the signal. For BRET, the donor molecule is firefly luciferase or a related bioluminescent protein, while the acceptor is green fluorescent protein or a color variant. While intermolecular spatial constraints are thought to be less restrictive with BRET, similar limitations related to sensitivity may apply. However, since the photon donor in BRET is produced by an enzymatic activity (luciferase), the potential for substrate-dependent signal amplification exists. Nonetheless, both suffer from issues related to spectral overlap that can render quantitative analysis of the two interacting fragments difficult in whole cells when expression levels are not exactly matched.

Detecting protein-protein interactions in living animals is difficult. Of the available strategies, complementation of firefly and Renilla luciferases are readily amenable to near real time applications in living animals (Ozawa et al., 2001; Paulmurugan and Gambhir, 2003), but the available fragments unfortunately suffer from considerable constitutive activity of the N-terminus fragments, thereby precluding general use of this strategy.

Thus a continuing need exits for a noninvasive analysis of protein-protein interactions. And so despite the growing body of knowledge in this area, there is still a strong and continuing need in the art to learn the identity and function of proteins engaging in protein protein interactions. In addition, because there is an unmet need to identify therapeutic compounds which modulate such activity there is also need in the art for the continued discovery in this area.

Figure 1:
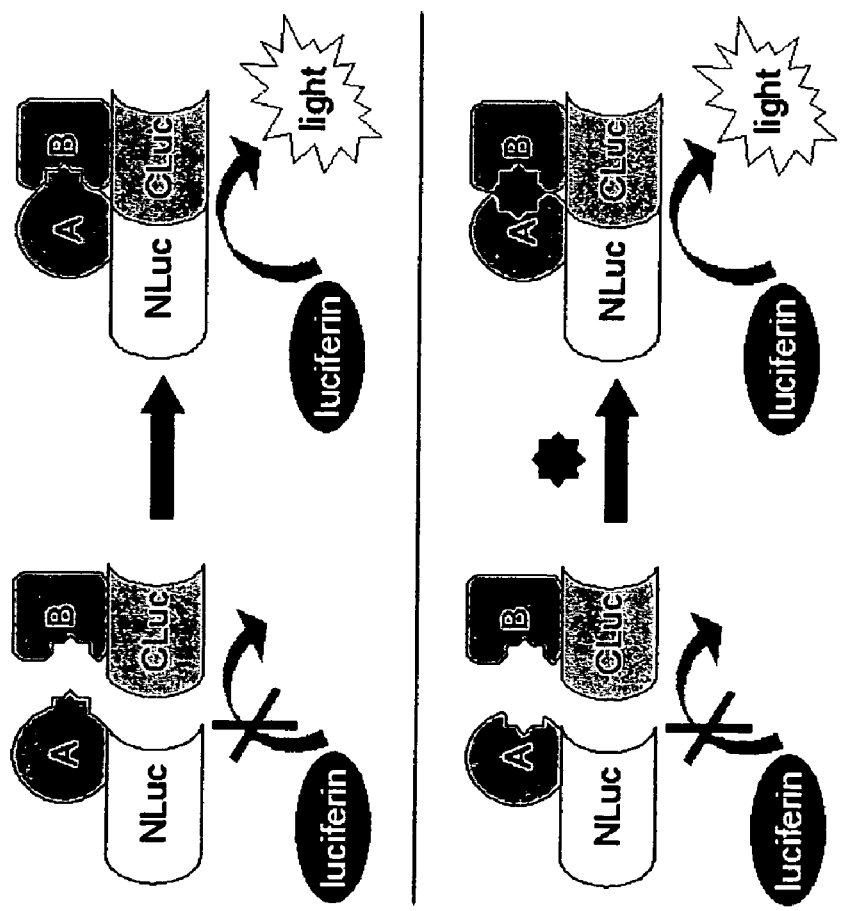
FIG. 1 depicts a schematic of a functional luciferase complementation imaging (LCI) of this discovery. Spontaneous association (upper panel) or drug-induced association (lower panel) of proteins A and B bring inactive fragments of luciferase into sufficiently close proximity to reconstitute emitting bioluminescence activity.

The discovery is described hereinafter in further detail with references to the aforedescribed FIGS. 1-16 in which like items are numbered the same in the aforedescribed Figures.

BRIEF DESCRIPTION OF THE INVENTION

In an aspect the discovery comprises an isolated functional complementation system activated by interaction of fused protein binding partners, the system comprising a protein fused to one luciferase fragment of a pair of companion firefly luciferase fragments, the pair having low background bioluminescence, in proximity to a protein fused to the other respective luciferase fragment of the pair such that reconstitution of the pair of fragments provides an emitting bioluminescent moiety such as a heterodimer. In an aspect the pair of firefly luciferase fragments is bioluminescent functionally capable. In an aspect the discovery comprises an isolated, activated, characterized and functional complementation system for detecting protein protein interactions. The system is usable in living biological systems.

In an aspect the discovery comprises a small molecule inducible complementation system comprising a protein fused to a companion luciferase fragment of a pair of firefly luciferase fragments, the pair having low background bioluminescence, in proximity to a protein fused to the other respective companion luciferase fragment of the pair such that upon reconstitution of the pair provides a bioluminescent heterodimer. In an aspect the pair of firefly luciferase fragments is bioluminescent functionally capable. After preparation and construction the fused proteins and the complementation system is recovered for use in this discovery.

In an aspect, a transgenic living moiety having competently integrated in its genome a functional genomic expression expressing a protein fused to one luciferase fragment of a pair of firefly luciferase fragments, the pair having low background bioluminescence that upon reconstitution provides an emitting (bioluminescent) dimer in proximity to a protein fused to the other respective luciferase fragment of the pair.

In an aspect, an expression vector comprising transcription and translation terminators, initiation sequences, and promoters useful for regulation of the functional expression of the DNA encoding the fusion proteins. The expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, and fusion expression systems such as GST and LacZ. Epitope tags can also e added to recombinant proteins to provide convenient methods of isolation.

Useful expression vectors containing regulatory elements from eukaryotic viruses are typically used in eukaryotic expression vectors, e.g., SV40 vectors, papilloma virus vectors, and vectors derived from Epstein Bar virus. Other exemplary eukaryotic vectors include pMSG, pAV009/A+, pMTO10/A+, pMAMneo-5, baculovirus pDSVE, and any other vector allowing expression of proteins under the direction of the SV40 early promoter, SV40 later promoter, metallothionein promoter, murine mammary tumor virus promoter, Rous sarcoma virus promoter, polyhedrin promoter, or other promoters shown effective for expression in eukaryotic cells.

In an aspect, a process of using a transgenic animal (model) for facilitating drug discovery which comprises subjecting a transgenic animal having a functional genomic expression competently integrated in its genome which expresses a protein fused to one luciferase fragment of a pair of firefly luciferase fragments the pair having low background bioluminescence that upon reconstitution provides an active (bioluminescent) heterodimer in proximity to a protein fused to another respective luciferase fragment of the pair to contact with a candidate drug and determining the effect if any of the contact of the drug on the animal model by determining bioluminescence.

In an aspect with regard to the transgenic animal, the other respective luciferase fragment of the pair is expressed by a functional genomic expression. In another aspect the other respective or both luciferase fragment(s) of the pair is added to the transgenic animal model for example by introduction of plasmid.

In an aspect using a nontransgenic animal the luciferase fragments are added to the animal by introduction of plasmid.

In an aspect, a method of quantifying interaction of two known proteins using a transgenic moiety to examine effects of at least one of cell cycle, signal transduction, induction of differentiation, and drug treatment, which comprises spatially placing a known protein fused to one luciferase fragment of a pair of companion firefly luciferase fragments the pair having low background bioluminescence that only upon reconstitution provides an active (bioluminescent) heterodimer in sufficient and effective spatial proximity to a known protein fused to the other respective companion luciferase fragment, determining if there is detectable bioluminescence and determining whether such bioluminescence is indicative that live cells have been impacted by at least one of cell cycle, signal transduction, induction of differentiation, or drug treatment. In an aspect the placement is carried out in a living cellular biological system by expression of a genomic construction.

In an aspect, the discovery comprises an isolated characterized and purified protein fused to one luciferase fragment of a pair of firefly luciferase fragments the pair having low background bioluminescence that upon reconstitution capably provides an active (bioluminescent) heterodimer that only upon reconstitution provides an active (bioluminescent) heterodimer. The pair is constructed, isolated and recovered for use in practicing this discovery.

In an aspect, an isolated, characterized and functional protein comprises a polypeptide having SEQ. ID. NO. 1 representing FRB protein domain fused to an N-terminal luciferase fragment (amino acid 2-amino acid 416).

In an aspect, isolated, characterized, purified and functional protein comprises a polypeptide having SEQ. ID. NO. 2 representing FKBP protein fused to a C-terminal luciferase fragment (amino acid 398-amino acid 550).

In another aspect, proteins comprise analogous sequences comprising fusion proteins of FRB and N-terminus fragments of firefly luciferase comprising amino acids 2-422 and amino acids 2-432 to be paired with fusion proteins of FKBP and C-terminus fragments of firefly luciferase comprising amino acids 396-550 and amino acids 396-550, respectively, for use in this discovery.

In an aspect, a method of screening an expression library or screening moieties to determine membership placement or permanency in an expression library comprising proteins, which comprises spatially placing a known protein fused to one luciferase fragment of a pair of firefly luciferase fragments (of this discovery) the pair having low background bioluminescence that upon reconstitution capably provides an emitting bioluminescent dimer in proximity to a candidate protein from the expression library fused to the other respective luciferase fragment, determining if there is detectable bioluminescence and determining whether such bioluminescence is indicative of known protein candidate protein interaction.

In an aspect, a method of screening a library of proteins fused to one part of a luciferase companion fragment of a pair of firefly luciferase fragments, the pair having low background bioluminescence that upon reconstitution provides an active emitting (bioluminescent) heterodimer in cell lysates fixed to a solid support which comprises spatially placing a known protein fused to one luciferase in proximity to a candidate protein from the library fused to the other respective luciferase fragment, determining if there is detectable bioluminescence and determining whether such bioluminescence is indicative of known protein candidate protein interaction.

In another aspect, an expression library comprises sequences of a known set of protein functionalities, such as but not restricted to kinases, phosphatases, reductases, or amino-tranferases, which could be capably fused in frame to sequences of either the N-terminal luciferase fragment or C-terminal luciferase fragment using standard molecular cloning techniques. In an aspect members of this fused expression library could then be co-transfected into mammalian cells or bacteria along with a bait protein that has previously been fused in frame with the opposing complementary luciferase fragment. The population of cells or bacteria could then be plated in media, allowed to grow for 24 hrs to 48 hrs, and then an appropriate concentration of D-luciferin could be added to media. The presence of a bioluminescent colony would indicate that a productive protein-protein interaction had occurred in those clones. The plasmids could be recovered from those cells using standard techniques and sequenced, thereby enabling the identification of novel protein-protein interactions from expressed libraries in live cells.

If desired genome-wide functional screening of small interfering RNA knockdown libraries can be carried using this discovery as a research tool.

Illustratively for example, System Biosciences' pFIV™ Lentiviral-Based siRNA Expression Systems, Mountain View, Calif., USA provide an approach to deliver and express small interfering RNA sequences. The luciferase fragments, when fused to target proteins, will enable functional analysis of the ability of members of siRNA libraries to alter upstream regulators and modulators of protein interactions.

As used herein, the term "siRNA" means short interfering RNA.

Other alternative fusion combinations could be envisioned, such as screening for adaptor protein interactions (three protein intereactions), or protein interaction traps modified for use with our complementation luciferase fragments instead of transcriptional activation strategies (Nature Cell Biol 3:1114, 2001).

In an aspect, a method of quantifying interaction of at least two known proteins in live cells in culture, live cells in xenograft models or live transgenic animals to examine effects of at least one of cell cycle, signal transduction, induction of differentiation, or drug treatment, which comprises spatially placing a known protein fused to one luciferase fragment of a pair of companion firefly luciferase fragments the pair having low background bioluminescence that only upon reconstitution provides an active (bioluminescent) heterodimer in proximity to a known protein fused to the other respective luciferase fragment, determining if there is detectable bioluminescence and determining whether such bioluminescence is indicative that live cells have been impacted by at least one of cell cycle, signal transduction, induction of differentiation, or drug treatment.

In an aspect, a method of measuring at least one pharmacological effect (including kinetics, dose-response) in a live mammalian system on association of a protein pair in live animals, live cells, cell lysates or purified protein pairs in that system comprises spatially placing a known protein fused to one luciferase fragment of a pair of firefly luciferase fragments the pair having low background bioluminescence that upon reconstitution capably provides an active (bioluminescent) heterodimer in proximity to a protein fused to the other respective luciferase fragment, determining if there is detectable bioluminescence and determining whether such bioluminescence is indicative of at least one pharmacological.

In an aspect, a high throughput drug screen for identifying compounds that directly or indirectly interrupt or enhance association of a specific protein pair in live cells, cell lysates, or purified protein pairs comprises a spatially placed protein of a protein pair, fused to one luciferase fragment of a pair of firefly luciferase fragments the pair having low background bioluminescence that upon reconstitution capably provides an active (bioluminescent) heterodimer in proximity to a protein of the protein pair fused to the other respective luciferase fragment, determining if there is detectable bioluminescence indicating association of the protein pair, adding a candidate compound to the system and after lapsed time determining if there is detectable bioluminescence and determining if that added compound has interrupted or enhanced association of the protein pair.

Further, in this regard, binding which is occurring or has occurred as a result of a drug candidate is detectable by action of emitted bioluminescence from luciferase. If the bioluminescence is occurring and is detectable and is significantly greater than any background bioluminescence, then a determination is made that the compound is active or potentially biologically active in this screen.

The pair of luciferase fragments are designed and prepared (companion engineered) and recovered for use so that when they are together initially and reassembled that they are functionally the same or substantially the same in all functional respect. This is so the luciferase reconstituted from the enhanced luciferase fragments is likely the same structure as the intact luficerase from which they were derived—but in theory it is possible that the library screen selected another capable functionally valid solution to the structural problem it was asked to solve. At this point it is sufficient to state that the reconstituted enzyme (i.e. the pair of companion fragments) is functionally and structurally similar to the native enzyme.

In an aspect, a method of examining physiological or pharmacological effects on association of protein pairs in living systems comprises spatially placing an isolated protein fused to one luciferase fragment of a pair of firefly luciferase fragments the pair having low background bioluminescence that upon reconstitution capably provides an active (bioluminescent) heterodimer in proximity to a another protein fused to the other respective luciferase fragment, wherein said proteins are members of a protein pair introduced into animals by transgenic breeding strategies, viral or non-viral trangene delivery vectors or carried in cells that are transferred into the host animal (e.g., tumor xenografts, stem cells, T or B lymphocytes) determining if there is detectable bioluminescence and determining whether such bioluminescence is indicative of protein-protein interaction.

In an aspect, a method of tracking live cellular and intracellular events in a living biological system in real time comprises spatially placing a protein fused to one luciferase fragment of a pair of firefly luciferase fragments the pair having low background bioluminescence that upon reconstitution capably provides an active (bioluminescent) heterodimer in proximity to another protein fused to the other respective luciferase fragment, determining if there is detectable bioluminescence and determining whether such bioluminescence is indicative of events that bring proteins of interest into contact through cell fusion events, or cell invasion processes, or host-pathogen interactions as might occur with infectious agents such as viruses, bacteria, parasites or fungi.

In an aspect, a method for identifying a compound that activates or inhibit protein-protein activity comprises bringing a test or candidate compound into contact with a protein-protein capable interactive area of a living biological entity, comprising a protein fused to one luciferase fragment of a pair of firefly luciferase fragments that upon reconstitution capably provides an active (bioluminescent) heterodimer in proximity to another protein fused to the other respective luciferase fragment, determining if there is detectable bioluminescence and determining whether such bioluminescence is indicative of an activation or inactivation of protein-protein interaction and if activation or inactivation has occurred due to the compound, making a determination of a future course of research or commercial action with regard to the candidate.

In an aspect an expression library comprising a library of known proteins. In an aspect an expression library comprises a library of proteins whose function is unknown.

A method for creating and using a knowledge database of protein protein interactions comprising acquiring a plurality of protein protein interactions by using the complementation system of this discovery, creating a knowledge database using that plurality of acquired data by entering acquired protein protein interaction information into the database using a searchable and retrievable organization. In an aspect the database is accessed and protein protein interaction information previously archived retrieved by means of a search and retrieval program functionally capable and adaptive to the database. Protein protein information so retrieved is used as input to make decisions regarding further testing or use of that compound.

In an aspect, screened molecules preferably are small molecule drug candidates. In particular, the method relates to a technique for screening for biological activity of these molecules comprising (a) exposing the fused protein-luciferase fragments or expressing target cells in culture to a candidate compound to produce a treated cell determining the amount of biolumenscence mediated by the exposure after a time and under conditions effective to illicit such lumenscence (c) scoring phenotypic or functional changes in treated cells and comparing the results to results from control cells which were not exposed to the candidate compound. In another embodiment, the method relates to a technique of diagnosing to determine whether a particular disorder in the cell (a) culturing test cells or tissues; (b) administering a compound to the system which can potentially mediate binding (c) measuring the biolumenscence from the cell and noting function effects in the test cells and (d) determining that the compound caused the cell operation if the biolumenscence is significantly different that control cells not exposed to the candidate compound.

DETAILED DESCRIPTION OF THE INVENTION

The inventors have identified, characterized, isolated, purified, sequenced and recovered an enzyme fragment pair (protein-luciferase fragment) that satisfies criteria for successful noninvasive analysis of protein-protein interaction, cell membranes, and capably enables meaningful biological interrogation and responses thereto in cell lysates, intact cells and living animals. Further, the inventors have identified, prepared, isolated and characterized a cellular system which provides a method of screening for compounds having protein protein binding activity.

In an aspect, the binding is detected by detecting emitted bioluminescence of luciferase indicative of binding.

As used herein, the term "activated" includes activated and capable of being active.

As used herein, the term "companion" includes DNA sequences and amino acid sequences that constitute enzyme activity or function when expressed together.

As used herein, the term "complementation" includes separate DNA sequences and amino acid residues that may align end to end, overlap or contain gaps when compared to the native sequences of said protein or reporter enzyme, but when together reconstitute reporter enzyme function.

As used herein, the term "protein" includes any large molecule composed of one or more chains of amino acids in a specific order; the order is determined by the base sequence of nucleotides in the gene that codes for the protein. The term "protein" includes a fragment and functional fragments of proteins.

As used herein, the term "small molecule inducible" means that upon administration of a synthetic organic compound, inorganic compound or natural substance of MW<5,000 or more preferably of MW<1,000, target proteins fused to said luciferase fragments will be brought into close proximity through binding of said compounds to the target proteins.

As defined herein, the term "protein-protein interaction" include any and all type(s) of meaningful interaction that a protein is capable of (such as protein-RNA interaction, receptor-ligand interaction, protein fragment interaction) with another protein, like protein or unlike protein or any other biological DNA or peptide containing the moiety.

As used herein, the term "expression" includes the biosynthesis of a product as an expression product from a gene such as the transcription of a structural gene into mRNA and the translation of mRNA into at least one peptide or at least one polypeptide. The term "expression" includes gene products such as proteins and functional fragments thereof.

As used herein, the term "expression library" includes a database, collection or assemblage of moieties or a system of containing capably identified moieties, cataloged or uncataloged, present or not present in the collection or assemblage and illustratively includes expression products of cDNA such as proteins, and enzymes including those wherein one or more of identity and function or known or are unknown.

As used herein, the term "low background bioluminescence" means low, none, or substantially no emitted or detectable bioluminescence.

A protein-protein complementation kit comprising a container housing an isolated and characterized polypeptide having Seq ID No 1 and an isolated and characterized polypeptide having Seq ID No 2.

As used herein, the term "rapamycin" (also called "sirolimus") is a peptide that was isolated from the bacteria strain *Streptomyces hygroscopicus*.

As used herein, the term "peptide" is any of a group of compounds comprising two or more amino acids linked by chemical bonding between their respective carboxyl and amino groups. The term "peptide" includes peptides and proteins that are of sufficient length and composition to effect a biological response, e.g. antibody production or cytokine activity whether or not the peptide is a hapten. term "peptide" includes modified amino acids, such modifications including, but not limited to, phosphorylation, glycosylation, pegylation, lipidization and methylation.

As used herein, the term "firefly luciferin" is used in a luciferin/luciferase system that requires ATP as a cofactor. Because of this, the firefly luciferase/luciferin system can capably be used as a bio-indicator (reporter) of the presence of energy or life.

As used herein, the term "firefly" includes species *photinus pyralis* and closely related species.

As used herein, the term "mammal" includes living animals including humans and non-human animals such as murine, porcine, canine and feline.

As used herein, the term "low background bioluminescence" means low, none, or substantially no emitted bioluminescence.

The inventors discovered that enzyme activity occurs in living cells or in living animals only upon complementation induced by the interaction of fused protein binding partners or by small molecules (drugs) that induce the interaction of fused proteins (FIG. 1). In using this discovery the complementation induction is brought about by the hereindescribed interaction of fused protein binding partners or by small molecules. It is believed that binding results in the emission of light energy of the associated luciferase.

Useful nonlimiting small drugs include rapamycin, tetracyline, estrogen and ectosone. Small Molecular resources are found on the World Wide Web. Such resources include 2D, USA. (http://www.wustl.edu/) databases including Pharmabase, CambrindgeSoft chemFinder Database, WWW Chemicals, RTAM Database, Klotho Database and the Declarative database at Washington University in St. Louis, One Brookings Drive, St. Louis, Mo. 63130 USA.

Further, three dimensional databases include The Cambridge cystallographic Data Centre (CCDC) and associated software, The CHIRBASE database, Molecular Diversity Preservatin International Database housing over 3200 small moleculae structures available for downloading in db, National Cancer Institute Databases, WWW Chemical Structures, Washington DC. USA The inventors have discovered an enhanced novel protein to protein interaction detection method and system. This discovery is used for effective, real time non-invasive analysis of protein-protein interaction, cell membrane investigations enables interrogation in cell lysates, intact cells, and living animals including living mammals.

Several important advantages and utilities flow from this discovery. In particular one advantage of the inventors' discovery is that the hybrid proteins form a complete biologic assay system that is independent of cell-specific molecular machinery such as transcription. Therefore, the discovery herein is useful in that protein interactions may be detected using this discovery in any subcellular compartment, and assembly of protein complexes may be monitored in real time using this discovery in living cells and living animals.

The inventors discovered that this firefly luciferase protein fragment complementation method and system produces a robust and broadly applicable detectable bioluminescence emission (signal) and demonstrates both modification-independent and phosphorylation-dependent protein interactions in intact living human cells and animals. If desired, one may utilize a sample including a representative sample including live cells of a living human cells and mammals.

This discovery is important to use an effective research tool because specific protein protein interactions are involved in almost any physiological process. If mankind is ever to cure cancer and other debilitating diseases killing humans, thus mankind must have and use bedrock research tools. Sensing extracellular signals is a matter of receptor to adaptor interactions and the shape of the cell is maintained by an intricate network of structural protein interactions. Finding interactions between proteins involved in common cellular functions is an advantageous way to get a broader view of how they work cooperatively in a cell.

As aforementioned, the inventors discovered firefly luciferase protein fragment complementation by screening incremental truncation libraries of N- and C-terminal fragments of luciferase, fused to the FRB domain of the kinase mTOR and FKBP-12, respectively. The inventors found that their enhanced FRB-NLuc/CLuc-FKBP luciferase complementation imaging (hereinafter "LCT") pair reconstituted luciferase activity in cells upon single-site binding of rapamycin in an FK506-competitive manner by using a method to identify and prepare an optimal pair of firefly luciferase fragments (enzymes) that reconstitutes an active (bioluminescent) heterodimer only upon association.

The identified fragments of Photinus pyralis luciferase (derived from pGL3; Promega) are fused to FRB and FKBP by a linker containing a flexible Gly/Ser region. A multiple cloning site also can be inserted between each pair of fused proteins to prepare fusion constructs. In an aspect, these fragments are isolated, recovered and sequenced.

From these isolated fusion constructs, N- and C-terminal incremental truncation libraries are generated by unidirectional exonuclease digestion and validated essentially as described (Ostermeier et al., 1999). The libraries are co-expressed in E. coli and screened in the presence of rapamycin for bioluminescence.

The two enhanced LCI fusion constructs, termed FRB-NLuc and CLuc-FKBP, are expressed from separate mammalian expression plasmids, pcDNA3.1 TOPO (FRB-NLuc) and pEF6-TOPO (CLuc-FKBP) (Invitrogen) and can be isolated, recovered and characterized.

The LCI fusion constructs are successfully transfected into living cells where expression of the fusion constructs occur.

LCI was used in three independent applications as are described hereinafter following.

In live mice bearing implants of cells expressing the FRB-NLuc/CLuc-FKBP LCI pair, dose- and time-dependent luciferase activity allowed target-specific pharmacodynamic analysis of rapamycin-induced protein-protein interactions in vivo.

In living functional mammalian cells expressing a Cdc25C-NLuc/CLuc-14-3-3ε LCI pair, drug-mediated disruption of cell cycle regulated protein-protein interactions was demonstrated by the inventors with the protein kinase inhibitor UCN-01 in a phosphoserine-dependent manner.

When applied to interferon-γ-dependent activation of JAK/STAT1, LCI revealed, even in the absence of interferon-γ-induced phosphorylation, STAT1 proteins existing in live cells as pre-formed dimers.

Thus, the inventors' enhanced LCI provides a platform for real time detection and characterization of regulated and small molecule-induced protein-protein interactions in intact cells and living animals and enables a wide range of novel applications in drug discovery, chemical genetics and proteomics research as an effective and capable research tool.

To develop an enhanced protein fragment complementation imaging system for broad use in living cells and animals, the inventors screened a combinatorial incremental truncation library for reconstitution of the enzymatic activity of a heterodimeric firefly (Photinus pyralis) luciferase (See FIG. 1). This specification describes the rationale and methods for application of luciferase complementation imaging (LCI) to protein pairs of interest.

The inventors gave special attention to considerations specific to LCI in the context of luciferase bioluminescence imaging in whole cells and living animals. In addition to technical aspects of LCI, the inventors addressed issues related to selection of protein pairs to be evaluated as well as cellular and physiologic contexts for the study of protein-protein interactions in vivo. The inventors discovery demonstrates that non-invasive molecular imaging of protein-protein interactions will enable investigators to determine how intrinsic binding specificities of proteins are regulated in a wide variety of normal and pathophysiologic conditions.

Figure 2:
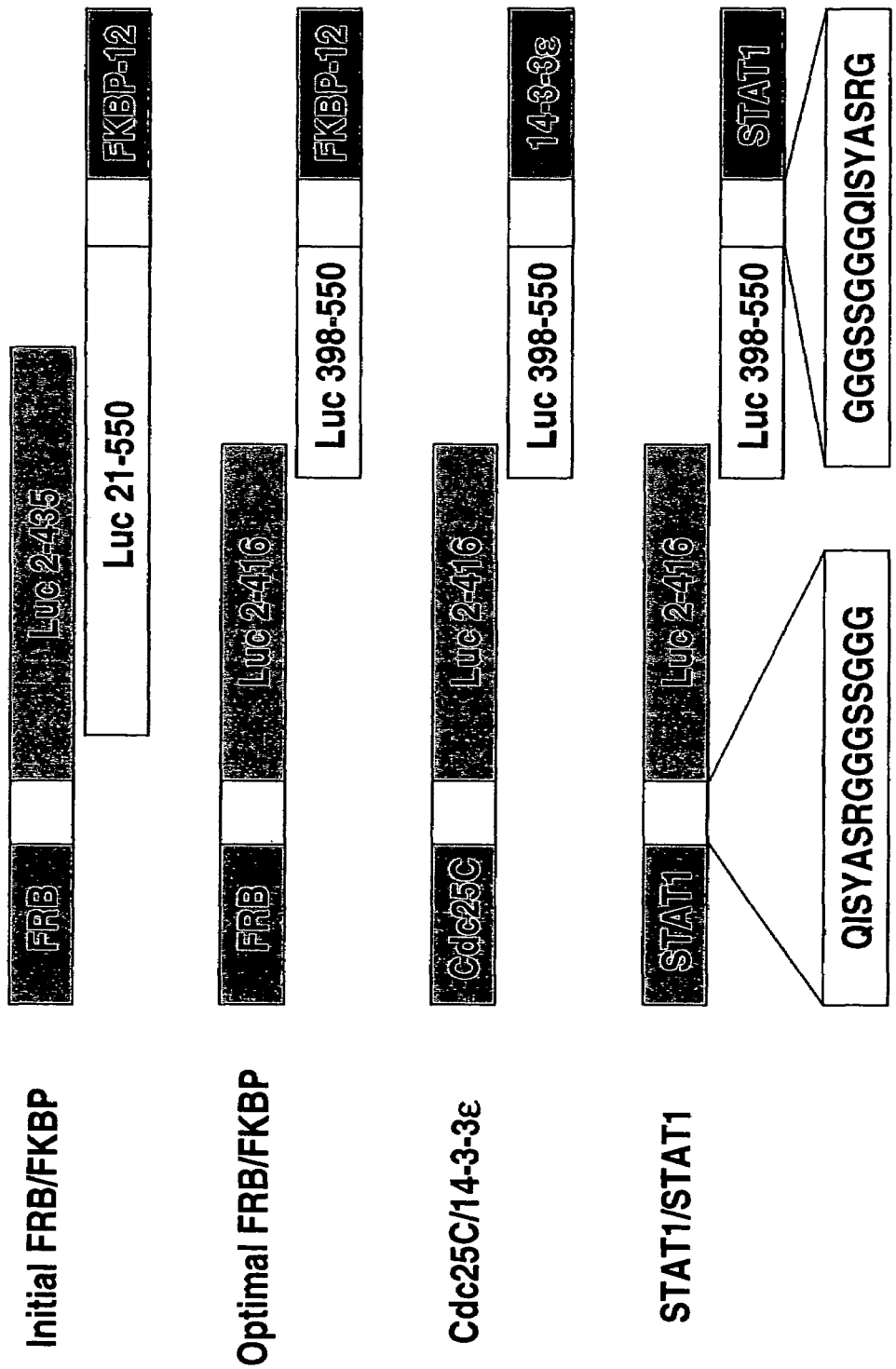
FIG. 2 depict schematic diagrams of functional LCI constructs. The initial FRB-NLuc and CLuc-FKBP fusions were used to generate incremental truncation libraries from which the optimal FRB-NLuc/CLuc-FKBP LCI pair was obtained. Additional constructs were generated by replacement of FRB or FKBP with the indicated open reading frames. The Peptides are shown in SEQ ID NOS 3 & 4, respectively.
Figure 3:
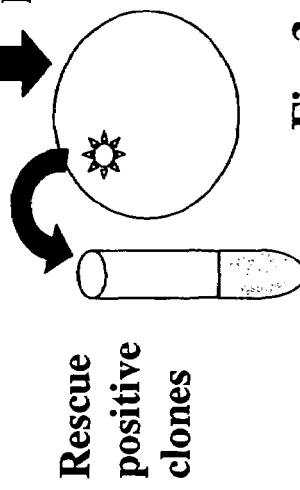
FIG. 3 provides a schematic of library construction and screening for enhancing LCI.
Figure 3:

Enhancing luciferase fragments for complementation. To identify an optimal pair of firefly luciferase fragments that reconstitutes an active (bioluminescent) heterodimer only upon association, the inventors constructed and screened a comprehensive combinatorial incremental truncation library as shown in FIG. 2 and FIG. 3 (Ostermeier et al., 1999). This library employs a well-characterized protein interaction system: rapamycin-mediated association of the FRB domain of human mTOR (residues 2024-2113) with FKBP-12 (Chen et al., 1995; Remy and Michnick, 1999; Galarneau et al., 2002).

Initial fusions of FRB and FKBP with N- and C-terminal fragments of luciferase, respectively, were intentionally designed, engineered and constructed according to this discovery such that the enzymatic activity of the individual overlapping fragments are weak or absent. The fragments of Photinus pyralis luciferase (derived from pGL3; Promega US, 2800 Woods Hollow Road, Madison Wis. 53711, USA) were fused to FRB and FKBP by a suitable effective linker containing a flexible Gly/Ser region. A multiple cloning site also was inserted between each pair of fused proteins.

From these constructs, N- and C-terminal incremental truncation expression libraries were generated by unidirectional exonuclease digestion and validated essentially as described (Ostermeier et al., 1999). The libraries are co-expressed in E. coli, isolated and recovered and screened in the presence of rapamycin for bioluminescence. From this screen, inventors identified an optimal pair of overlapping amino acid sequences for the NLuc fragment and for the CLuc fragment. The enhanced combination of fragments produced no signal in the absence of rapamycin and strong bioluminescence in the presence of the dimerizing agent rapamycin. This has been found to be true for the inventors discovery.

Mammalian expression constructs. For work in mammalian cells, the two enhanced LCI fusion constructs, termed FRB-NLuc and CLuc-FKBP, were expressed in separate mammalian expression plasmids, pcDNA3.1 TOPO (FRB-NLuc) and pEF6-TOPO (CLuc-FKBP) (Invitrogen, 1600 Faraday Avenue, P.O. Box 6482, Carlsbad, Calif. 92008, USA). To generate control constructs, site directed mutagenesis (QuikChange, Stratagene) is used to create point mutations in FRB (S20351) and to introduce a stop codon in CLuc-FKBP at the 3' end of the linker for expression of unfused CLuc.

Determining the fidelity of enhanced LCI for reporting protein association. For initial tests of responsiveness to rapamycin, the dynamic range and time dependence of bioluminescence signal for the FRB-NLuc/CLuc-FKBP pair expressed in live HEK-293 cells and in lysates is measured. In cell lysates, the maximal dynamic range of bioluminescence signal is approximately 4 orders of magnitude for optimal pairs. LCI signal is generated rapidly in cell lysates upon addition of rapamycin, with a half-time of approximately 2 minutes. In live cells, maximal induction of bioluminescence by rapamycin is achieved at 6 hrs, a delay attributable to slow accumulation of rapamycin in cells.

In live cells and in cell lysates, the inventors enhanced LCI system successfully reproduced published apparent $K_d$ values for rapamycin (FIG. 3) (Chen et al., 1995; Remy and Michnick, 1999; Galarneau et al., 2002). To test the specificity of the LCI system, the inventors mutated the FRB fragment in the FRB-NLuc construct to a form FRB(S20351) (Chen et al., 1995), which should be insensitive to rapamycin. The inventors showed that this mutation, even in the presence of rapamycin, produced low bioluminescence signal similar to the optimal pair in absence of rapamycin. An unfused CLuc fragment co-expressed with FRB-NLuc produced 3-fold lower signal than co-expressed FRB-NLuc/CLuc-FKBP in the absence of rapamycin consistent with weak, rapamycin-independent association of FRB and FKBP (Chen et al., 1995; Remy and Michnick, 1999), while expression of single constructs produced no detectable signal relative to untransfected cells.

Thus, advantageously our enhanced LCI pair eliminated the substantial bioluminescence activity of the N-terminal luciferase fragment that was problematic with previous split-luciferase systems based on simple bisection of luciferase (Paulmurugan et al., 2002).

Technical considerations for LCI in cells and lysates. While the process for transfection of cells and expression of the fusion constructs used in LCI will be apparent to one of skill in the art after reading this specification, a few special considerations for assaying protein association by bioluminescence imaging should be noted. Individual fusion proteins should be tested for background bioluminescence activity. To assess specificity of protein interactions, an irrelevant or mutant protein association partner is helpful. Measurement of protein association by LCI can also be confounded by changes in protein levels or cell number rather than association state. To control for events not directly related to protein association it may be useful to incorporate an independent marker into LCI reporter cells, or to include in the study a parallel set of cells or animals expressing intact luciferase. Assays should be planned to allow for the kinetics of light production by luciferase upon addition of luciferin in a particular assay format.

Unlike reporter enzymes that produce a colorimetric output that accumulates steadily with time, luciferase produces a transient signal (good reproducibility can be attained) by integrating the signal over an appropriate time period with relatively stable light production. Commonly, 1 min acquisition times taken 10 min after addition of substrate results in reproducible signals. Overall, the LCI signal is generally lower than that for intact luciferase, although maximal activity is likely to depend on the protein pair under investigation. Therefore, it is important to maximize signal by ensuring that reporter cells express both LCI fusion proteins. It should also be noted that luciferase activity is dependent on magnesium ATP, and thus, variations in cellular ATP affect luminescence output. Therefore, addition of sufficient magnesium ATP to the buffer is necessary for measurement of luciferase activity in cell lysates or permeablized cells. Commercially available luciferase substrate buffers (Promega US, 2800 Woods Hollow Road, Madison Wis. 53711, USA) are appropriate for assaying luciferase activity under these conditions, since these buffers contain appropriate amounts of ATP in addition to luciferin.

Figure 4:
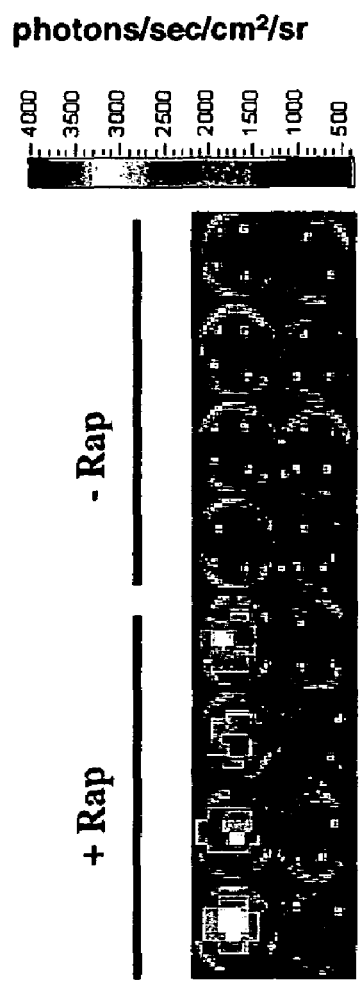
FIG. 4 shows monitoring rapamycin-induced FRB/FKBP association in live cells by LCI. HEK-293 cells transfected with FRB-NLuc/CLuc-FKBP or S2035I FRB-NLuc/CLuc-FKBP were treated for 6 hrs with 50 nM rapamycin. A representative pseudocolor MS bioluminescence image of live cells in a 96-well plate is shown.

Technical considerations for LCI in mouse models. Bioluminescence imaging of animals using CCD cameras such as the IVIS (Xenogen Corporation, 860 Atlantic Avenue, Alameda, Calif. 94501, USA) has been rapidly adopted as a broadly applicable and facile means to quantify relative expression of luciferase reporter activity (FIG. 4). (CCD means Charge Coupled Device: one of the two main types of image sensors used in digital cameras.) The IVIS® Imaging System includes a sensitive CCD camera, a dark imaging chamber to minimize incident light, and specialized software to quantify and analyze the results. IVIS is a registered trademark of Xenogen Corporation. See: http://www.xenogen-.com/prodimagl.html. Any such bioluminescence imaging system can be capably used with the instant discovery.

Because firefly luciferase (such as that from the North American firefly Photinus pyralis) bioluminescence imaging has very high sensitivity and broad dynamic range relative to other techniques for imaging live animals, such as fluorescence or micro-PET (microPET® is registered trademark of Concorde Microsystems, 10427 Cogdill Rd., Suite 500, Knoxville, Tenn. 37932, for dedicated small animal PET scanner). It is perhaps an optimal means for detecting protein interactions in live animals. However, spatial and temporal characteristics of bioluminescence imaging must be considered in planning LCI work.

Typical luminescence images obtained by CCD cameras have resolution on the order of 2 mm, suitable for many, but not all, anatomic imaging purposes. Temporal considerations for imaging include the time needed for image collection and the practical frequency for re-imaging the same animal. Depending on the intensity of the luminescence signal obtained, the time needed to acquire an image may be as little as 1 second or as long as 10 to 20 minutes. In live mice, bioluminescence signals from firefly luciferase reaches a transient plateau phase approximately 10 minutes after i.p. injection of luciferin. For a given mouse, firefly luciferase bioluminescence may be detectable for as much as 4 to 6 hours after administration of luciferin.

Considerations for application of LCI includes a selection of protein pairs for LCI. LCI can theoretically be used to study any process that alters the association state of a pair of proteins, including conformational changes, compartmentation changes, post-translational modifications such as phosphorylation, or protein association mediated by small-molecules. However, the practical utility of LCI to study a particular pair of interacting proteins should be carefully considered. While any reporter strategy may perturb the system under investigation, expression of certain types of protein pairs is more likely to influence cellular function. For example, cellular homeostasis is likely to be disrupted by overexpression of proteins that regulate cellular processes through titration of binding partners. Proteins expressed as LCI fusions may also act as competitors for endogenous proteins. In addition to the effects of enforced protein expression on a system, the nature of the luciferase reporter must be considered. For example, protein interactions that occur in the extracellular space, where ATP (adenosine triphosate) levels are very low, are not likely to be detectable by LCI since luciferase activity is dependent on ATP. Finally, to reduce the likelihood that fusion to the luciferase fragments will negatively impact the function of the protein pair, existing structural information should be considered. Introduction of steric bulk, perturbation of folding patterns, or masking of functional domains and intracellular localization sequences are among the potential causes of poor performance of LCI reporters.

Selection of applications and model systems for luciferase complementation imaging (LCI). In general, luciferase complementation imaging in live animals such as living mammals, permits study of protein interactions in a specific cell population in response to a physiologic event. For example, LCI could be applied to measure pharmacokinetics and pharmacodynamics of inhibition of protein association in tumor xenografts in response to a therapeutic agent. Considerations that affect the design of LCI tests in live animals include the means of incorporation of LCI protein pairs into the animal, expected dynamic range of the LCI signal obtained, and time dependence of the events to be imaged.

Introduction of LCI pairs into animals. There are three main methods for incorporating LCI protein pairs into live animals: 1) ex vivo tranfection, 2) gene therapy, and 3) hydrodynamic infusion.

The most facile of these three methods of choice is transient or stable introduction of the LCI constructs into cells ex vivo. Cells ($3\times10^6$ per 10 cm dish or $1.5\times10^5$ per 35 mm dish) can be transiently co-transfected with pairs of plasmids or single plasmids using FuGene-6 (Roche, Indianapolis, IN or F. Hoffmann-La Roche Ltd, Group Headquarters, Grenzacherstrasse 124, CH-4070 Basel, Switzerland) according to the manufacturer's directions. Twenty four hours after successful transfection, $2\times10^6$ cells suspended in 150 µl Matrigel (B.D. Biosciences, 2350 Qume Drive, San Jose, Calif., USA 95131-1807) can be implanted into the peritoneal cavity (i.p.) of nude mice (male, 6 wk, NCRU-nu/nu (Taconic)) for imaging tests. In addition, stable clones also can be isolated and maintained in medium supplemented with L-glutamine (1%), heat-inactivated fetal bovine serum (10%), penicillin/streptomycin/fungizone (0.1%), and the selection drug G418 (1 mg/ml) in a 5% $CO_2$ incubator at 37° C. Similarly, stably transfected tumor cells can be implanted using Matrigel or alternatively, tumor xenografts can be made in nude mice. For tumor xenografts, cells ($1\times10^7$) can be injected subcutaneously into flanks of 6-week old male NCr nu/nu mice (Taconic Farms, Germantown, N.Y., USA) and allowed to grow until 5-10 mm diameter tumors form (1-2 weeks).

Also, LCI constructs may also be introduced directly into live animals, for example, by gene therapy strategies based on infectious agents (viral), or transduction reagents (liposomes, peptide permeation motifs).

In an aspect, in a mouse model one may hydrodynamically inject a plasmid bearing the LCI genome into tail veins of that mouse model. For example, FVB mice (6 to 8 wk-old males) obtained from Charles River Breeding Laboratory (Wilmington Mass., USA or Indipendenza 11 Calco (Lecco) Italy) and maintained under strict adherence to institutional guidelines can be used. In vivo transfection of cells in mouse livers can be performed using the hydrodynamic method as described previously [Liu F, Song Y, Liu D. Hydrodynamics-based transfection in animals by systemic administration of plasmid DNA. Gene Ther 1999;6(7):1258-66].

Briefly, the plasmid DNA is diluted in phosphate buffer (without $Mg^{++}$, $Ca^{++}$) in a volume of 1 mL/10 g body weight (BW) and is rapidly (within 10 sec) injected into the tail veins of mice using a 3-mL syringe fitted with a 27-gauge needle. Injection of the LCI plasmid successfully induces and produces expression of the fusion proteins in the mouse liver.

Gene Therapy Strategy Based on Using Infectious Agents.

Gene therapy is a broad class having several aspects but normally a gene is inserted into a non-specific location within the genome to replace a gene, or one gene is exchanged for another gene through homologous recombination or if desired a gene is repaired through selective reverse mutation or if desired the regulation (the degree to which a gene is turned on or off) of a gene could be altered.

In the first aspect noted above, a vector (a carrier) is used to deliver the therapeutic gene to the desired patient's target cells. If desired this may be done by using a cassette.

For in vivo delivery (e.g., in methods of gene therapy) genetic material of the discovery (preferably contained within a suitable expression vector) can be administered to a subject in a pharmaceutically acceptable carrier. The term "pharmaceutically acceptable carrier", as used herein, is intended to include any physiologically acceptable vehicle for stabilizing nucleic moieties of the present discovery for administration in vivo, including, for example, saline and aqueous buffer solutions, solvents, dispersion media, antibacterial and antifungal agents, isotonic and absorption delaying agents, and the like. The use of such media and agents for pharmaceutically active substances is well known in the art. Except insofar as any conventional media is incompatible with the polynucleotide-carrier complexes of the present discovery, use thereof in a therapeutic composition is contemplated.

One common vector is a virus genetically altered to carry normal human DNA. Viruses can encapsuled and deliver their carried genes to human cells in a pathogenic manner.

Illustrative viruses which can be employed herein include adenoviruses, adeno-associated viruses, retroviruses, lentiviruses, and Herpes simplex viruses.

In any event, target cells such as the patient's liver or lung cells are infected with the viral vector. The vector then provides the therapeutic gene into the target cell. The generation of a functional protein product from the therapeutic gene follows.

Some of the different types of viruses used as gene therapy vectors: including retroviruses, adenoviruses, adeno associated viruses and Herpes simplex viruses. More in detail, retroviruses are viruses that can create double-stranded DNA copies of their RNA genomes; adenoviruses are viruses with double-stranded DNA genomes, adeno-associated viruses are small, single-stranded DNA viruses that can insert their genetic material at a specific site on chromosome 19 and Herpes simplex viruses are double-stranded DNA viruses that infect a particular cell type, neurons.

There are several nonviral options for gene delivery. The simplest method is the direct introduction of therapeutic DNA into target cells. This approach is limited in its application because it can be used only with certain tissues and requires large amounts of DNA. The direct approach may involve use of the gene gun.

Another nonviral approach is to use an artificial lipid sphere with an aqueous core. This liposome, which carries the therapeutic DNA, passes the DNA through the target cell's membrane.

Therapeutic DNA also can get inside target cells by chemically linking the DNA to a molecule that will bind to special cell receptors. Once bound to these receptors, the therapeutic DNA constructs are engulfed by the cell membrane and passed into the interior of the target cell. This delivery system tends to be less effective than other options.

In addition, transgenic mouse models may be useful in some instances. Ex vivo preparation of cells with LCI constructs permits the investigator to maximize signal by selecting or sorting cells to ensure incorporation of both LCI constructs into the same cell (if the constructs are not incorporated into single DNA plasmids). Ex vivo preparation of cells also permits introduction of the LCI pair into the widest variety of tissue types and genetic backgrounds. Standard electroporation, transfection or viral transduction techniques can be used to deliver plasmid DNA to cells for production of transgenic models.

Transgenic Animals

As used herein the term "transgenic animal" is a mouse or a living animal that carries a foreign gene that has been deliberately inserted into its genome. The foreign gene is constructed using recombinant DNA methodology.

Two main methods are used: (1) transforming embryonic stem cells (ES cells) growing in tissue culture with the desired DNA and injecting the desired gene into the pronucleus of a fertilized mouse egg and (2) the pronucleus method.

In addition to a structural gene, the DNA usually includes other sequences to enable it to be incorporated into the DNA of the host and to be capably expressed correctly by the cells of the host. Transgenes should include promoter, enhancer, gene to be expressed, splice donor and acceptor and intron sequences, and termination/polyadenylation sequences. Transgenes must be excised from the bacterial plasmid sequences in order to be expressed in mice.

In (1) DNA, immediately above, is built using recombinant DNA methods, the DNA containing the structural gene you desire, and then vectoring DNA to enable the molecules to be inserted into the host DNA molecules. Use promoter and enhancer sequences are used to enable capable gene expression by host cells. Host cells are transformed in culture by exposing cultured cells to the DNA so that some cells will incorporate it. One then selects for successfully transformed cells and injects these cells into the inner cell mass of mouse blastocysts. Embryo transfer is carried out by preparing a pseudopregnant mouse (by mating a female mouse with a vasectomized male). The stimulus of mating elicits hormonal changes needed to make the uterus of the female mouse receptive. Embryos are transferred into the uterus wherein they implant successfully and develop into healthy pups. Offspring are tested by removing a small piece of tissue from the tail and examining its DNA for the desired gene by Southern blotting. Typically, 10-20% of pups will be heterozygous for the gene. Two heterozygous mice are mated. Screening of their offspring should result in 1:4 homozygous for the transgene. Mating these will find the transgenic strain.

Prepare the DNA as in (1) immediately above, but additionally transform fertilized eggs in that freshly fertilized eggs are harvested before the sperm head has become a pronucleus. Inject the male pronucleus with this DNA. When the pronuclei have fused to form the diploid zygote nucleus, allow the zygote to divide by mitosis to form a 2-cell embryo. Then implant the embryos in a pseudopregnant foster mother and proceed as above.

Particle Gun Technology

Particle gun technology may be employed as a delivery system and a means to introduce desired DNA materials into cells. The particle guns shoot DNA-coated materials into living cells providing direct deposit of genetic material into living cells, intact tissues, and microscopic organelles. Du Pont Co., DuPont Building, 1007 Market Street, Wilmington, Del. 19898, USA., and Agracetus Inc., 8520 University Green, Middleton Wis. 53562, USA, have United States patent applications pending. Useful nonlimiting examples of particle guns includes the Biolistic gene gun and the Particle Gun.

Advantageously the detection of protein interactions in living animals can provide useful information about the molecular basis of physiologic and pathophysiologic events as well as molecular response to therapeutic agents.

Overall, luciferase complementation imaging of protein interactions in cells and small animal models has been developed to permit rapid and repetitive measurement of protein pairs of interest. Enhanced luciferase complementation, quantified by imaging with a CCD camera equipped with appropriate software, can provide an accurate measure of relative protein association in animals and quantitative measurement of protein association in live cells.

The firefly luciferin is readily available. For example analytical Luminescence Laboratory offers firefly luciferin, luciferase, buffers, and standards in a variety of combinations, plus protocols for applications in genetic engineering and for detecting bacteria and yeast. Firefly luciferin and luciferase are also offered by Accurate Chemical and Scientific Corp., Westbury, N.Y., USA; Boehringer Mannheim Biochemicals Inc., Indianapolis; Calbiochem—Novabiochem Corp., San Diego; ICN Biomedicals, Costa Mesa, Calif.; Promega Corp (Promega US, 2800 Woods Hollow Road, Madison Wis. 53711, USA., Madison, Wis.; R&D Systems Corp., Minneapolis; Sigma Chemical Corp., Sigma-Aldrich, 3050 Spruce St., St. Louis, Mo. 63103, USA. St. Louis; Worthington Biochemical Corp., Freehold, N.J.; and others.

Methods of measuring bioluminescence include using a luminometer which is capably configured for use with firefly luciferase. One illustrated luminometer is Turner Designs Model 20, Turner Designs, Inc., 845 W. Maude Avenue, Sunnyvale, Calif. 94085, USA which is a direct current luminometer employing photon counting to quantify light emission. This unit allows for direct measurements of luminescence of living cells and tissues.

1. In an aspect a determination is made of the signal differential regarding detected and measured bioluminescence from the system of this discovery being evaluated such as a living system having an added small molecule or an added candidate compound. In an aspect a signal differential is considered significant if it shows greater than about two fold change in bioluminescence of detected bioluminescence over either of background or standard bioluminescence. In an aspect the signal differential is considered significant if it shows greater than about five or ten fold over either of background or standard bioluminescence. In some instances a signal differential is considered significant if it shows greater than about a 100 fold increase over background or standard. In an aspect signal differential used in making a decision or determination of the activity of the small molecule, its influence or utility in such a system based on that respective signal differential. In an aspect the system comprises An isolated, characterized and functional complementation system comprising a protein fused to one luciferase fragment of a pair of firefly luciferase fragments, the pair commonly having low background bioluminescence, in proximity to a protein fused to the other respective luciferase fragment of the pair such that upon reconstitution of the pair provides a bioluminescent emitting moiety. A system wherein the system is small molecule inducible. The system is operated for a meaningful time and in a meaningful capably functional manner in accordance with this discovery so as to achieve the desired objective of this discovery.

EXAMPLES

The following examples are illustrative and are not meant to limit the discovery in any way.

Chemicals and Reagents

UCN-01 (NSC 638850) was provided by Drug Synthesis and Chemistry Branch, NCI, National Institutes of Health, U.S. Government, Washington D.C., USA. D-luciferin was obtained from Xenogen Corporation, 860 Atlantic Avenue, Alameda, Calif. 94501, USA. Rapamycin and all other reagents were from Sigma Chemical Co, Sigma-Aldrich, 3050 Spruce St., St. Louis, Mo. 63103, USA.

Library Construction and Screening

Initial N-terminal and C-terminal fragments of firefly (*Photinus pyralis*) luciferase were amplified from pGL3-Control (Promega US, ). The FRB domain of human mTOR (residues 2024-2113) and hu(Promega US, 2800 Woods Hollow Road, Madison Wis. 53711, USA man FKBP-12 were generated by PCR amplification from plasmids kindly provided by X. F. Zheng (Washington University in St. Louis, One Brookings Drive, St. Louis, Mo. 63130, USA). A flexible Gly/Ser linker and a multiple cloning site (BglII, BsiWI, MluI, SmaI) were added using synthetic oligonucleotide primers. The fusions were expressed in *E. coli* in plasmids pDIM-N2 and pDIM-C6 (gift of S. Benkovic, The Pennsylvania State University 201 Shields Building, Box 3000 University Park, Pa. 16804-3000, USA (15) and isolated.

Briefly, N- and C-terminal incremental truncation libraries were constructed by unidirectional digestion with exonuclease III (Exo III) essentially as described (15). Both libraries were characterized by sequencing and restriction digest of randomly chosen clones to confirm that the obtained truncations covered the full length of each luciferase fragment. Libraries were packaged in phage and *E. coli* were co-infected with phage libraries, followed by selection on LB agar plates containing 50 µg/ml ampicillin, 50 µg/ml chloramphenicol, 0.3 mM IPTG and 1 µM rapamycin. To visualize positive clones, colonies were blotted to sterile nitrocellulose filters. Filters were moistened with substrate solution (1 mM D-luciferin in 0.1 M sodium acetate (pH 5.0) for 3-5 min) (16), and then imaged with an IVIS CCD camera (Xenogen; 1 min exposure, f-stop=1, binning 8, FOV 15 cm) to locate bioluminescent colonies. Clones of interest were isolated and re-tested for rapamycin-inducible bioluminescence.

Plasmids were rescued from these clones, separated, and re-transformed into *E. coli* to confirm that plasmid pairs, not single plasmids, recapitulated the original phenotype. The extent of deletion in candidate LCI pairs was characterized by sequencing. Fusions were amplified with primers adding a Kozak consensus sequence to the 5' end and ligated into mammalian expression vectors pcDNA3.1 TOPO (FRB-NLuc) and pEF6-TOPO (CLuc-FKBP) (Invitrogen).

DNA Constructs

To replace the FRB with human Cdc25C or human p91 STAT1 (J. E. Darnell Jr., The Rockefeller University, 1230 York Avenue, NY, N.Y. 10021, USA.) in the NLuc fusion vector, open reading frames of these cDNAs were amplified by PCR using 5' primers containing a BamHI site and Kozak consensus sequence upstream of the start site and 3' primers which reconstituted the linker region up to the BsiWI site. FRB was replaced using the BamHI and BsiWI sites. FKBP was similarly replaced with 14-3-3ε or STAT1 using BsiWI at the 3' end and EcoRV at the 5' end.

Site directed mutagenesis (QuikChange, Stratagene) was used to generate point mutations in FRB (S2035I), Cdc25C (S216A), and STAT1 (Y701F) and to introduce a stop codon in CLuc-FKBP at the 3' end of the linker for expression of unfused CLuc. Unfused NLuc (2-416) was amplified from pGL3 and ligated into pcDNA3.1-V5/HIS TOPO.

The STAT1-NLuc and CLuc-STAT1 open reading frames were cloned into lentiviral vectors (gift of J. Milbrandt, Washington University in St. Louis, One Brookings Drive, St. Louis, Mo. 63130, USA ) downstream of a CMV promoter and upstream of an IRES linked to EGFP (Clontech) or mRFP (R. Tsien, UCSD), respectively.

Cell Culture

HEK-293 cells were cultured in Dulbecco's Modified Eagle Medium (DMEM), (Life Technologies, 2575 University Ave. W., St. Paul, Minn. 55114 USA) supplemented with 10% fetal calf serum (FCS), 1% glutamine, 0.1% P/S, 0.1% fungizone. Cells ($3 \times 10^6$/10 cm dish or $1.5 \times 10^5$ per 35 mm dish) were transiently co-transfected with pairs of plasmids as indicated using FuGene-6 (Roche) according to the manufacturers directions.

Cells ($1 \times 10^4$/well in 100 µl media) were transferred to 96-well black walled plates 16-24 hrs after transfection. At the times indicated, growth media was replaced with media containing appropriate drugs or vehicles. To image live cells, D-luciferin (10 µl of 1.5 mg/ml in PBS) was added to wells. Photon flux for each well was measured 8-10 min after addition of D-luciferin with an IVIS CCD camera (1 min exposure, f-stop=1, binning 8, FOV 15 cm). Cell lyastes used for imaging were prepared using Reporter Lysis Buffer (Promega US, 2800 Woods Hollow Road, Madison Wis. 53711, USA) according to the manufacturers directions. Lysates (16 µg protein/20 µl) were incubated with rapamycin or vehicle (drug solvent) for 1 min to 30 min and 100 µl Luciferase Assay Reagent (Promega US, (Promega US, 2800 Woods Hollow Road, Madison Wis. 53711, USA) was added to each well.

Bioluminescence was measured immediately using the IVIS as above and luminescence was normalized to protein content in samples as determined by BCA (Pierce Biotechnology, Inc., Customer Service Department, P.O. Box 117, Rockford, Ill. 61105 U.S.A) or Bradford assay (Bio-Rad, Life Science Research, 2000 Alfred Nobel Drive, Hercules, Calif. 94547, USA).

Western Blot Analysis

Cells ($3 \times 10^6$/10 cm dish) were transfected with the indicated plasmids (6 µg each). Media was removed 6 hrs prior to lysis and replaced with media containing UCN-01 at the concentrations indicated. Cells were washed with PBS and lysed by incubation for 30 min at 4° C. with 1 ml RIPA buffer containing protease inhibitors (50 mM tris-HCl, pH 7.4, 1% NP-40, 0.25% deoxycholic acid, 150 mM NaCl, 1 mM EDTA, 1 mM each PMSF, sodium orthovanadate, and NaF, 1 µg/ml each leupeptin, aprotinin, pepstatin). After centrifugation to remove insoluble material, protein concentration was determined by BCA (Pierce Biotechnology, Inc., Customer Service Department, P.O. Box 117, Rockford, Ill. 61105 U.S.A). The Bicinchoninic Acid (BCA) test to determine protein concentration is a highly sensitive alternate assay to the Lowry assay.

Proteins (200 µg) were separated by SDS-PAGE and analyzed using polyclonal primary antibodies against pGL3 luciferase (Promega US, 2800 Woods Hollow Road, Madison Wis. 53711, USA) or phospho-S216-Cdc25C (Santa Cruz Biotechnologies, 2145 Delaware Avenue, Santa Cruz, Calif. 95060, U.S.A.). Bound primary antibodies were visualized with horseradish peroxidase-conjugated secondary antibodies using ECL (Amersham Corporation, 800 Centennial Avenue, P.O. Box 1327, Piscataway, N.J. 08855-1327, USA).

Mouse Imaging

HEK-293 cells were transfected (6 µg each plasmid per $4 \times 10^6$ cells) with FRB-NLuc/CLuc-FKBP or S2035I FRB-NLuc/CLuc-FKBP as indicated. Mice (male, 6 wk, NCRU-nu/nu (Taconic, 273 Hover Avenue, Germantown, N.Y. 12526, USA)) were implanted i.p. 24 hrs after transfection with $2 \times 10^6$ cells suspended in 150 µl Matrigel. (B.D. Biosciences, 800 Centennial Avenue, P.O. Box 1327, Piscataway, N.J. 08855-1327, USA). Two hours later, mice were injected i.p. with D-luciferin (150 µg/g in PBS) and imaged 10 min later with the IVIS (1 min exposure, binning 8, f-stop 1, FOV 15 cm). After an additional 18 hrs, groups of 4 mice were treated with rapamycin (i.p.; 1.0, 2.0 or 4.5 mg/kg) in vehicle (80% DMSO, 20% EtOH) or vehicle only. At the indicated times after treatment with rapamycin, mice were again humanely injected i.p. with D-luciferin and imaged 10 min later in an approved protocol. All animals survived the imaging studies and could be re-imaged over and over to serve as their own controls thereby demonstrating an advantage of this non-invasive method for detecting protein-protein interactions in vivo. Photon flux (photons/sec/cm$^2$/steradian) was quantified on images using a uniform rectangular region of interest (ROI) encompassing the entire abdomen and analyzed with LivingImage (Xenogen) and Igor (Wavementrics, Lake Oswego, Oreg., USA) image analysis software.

EXAMPLES AND DISCUSSION

To identify an optimal pair of fragments of firefly (*Photinus pyralis*) luciferase that reconstitute an active (bioluminescent) heterodimer only upon association, the inventors constructed and screened a comprehensive combinatorial incremental truncation library (15). This library employed a well-characterized protein interaction system, rapamycin-mediated association of the FRB domain of human mTOR (residues 2024-2113) with FKBP-12. Initial FRB-NLuc and CLuc-FKBP fusions (FIG. 2) were designed with overlapping fragments of luciferase in which enzymatic activity of the individual fragments was weak (FRB-NLuc) or absent (CLuc-FKBP). From these constructs, N- and C-terminal incremental truncation libraries were generated by unidirectional exonuclease digestion and validated essentially as described (15). The FRB-NLuc and CLuc-FKBP truncation libraries were then co-expressed in *E. coli* in the presence of rapamycin to identify pairs of luciferase fragments reconstituting bioluminescence. Of the ~19,000 colonies screened, 123 (0.65%) produced significant bioluminescence (>10-fold over background). Subsequent analysis yielded three truncation pairs displaying the strongest increase in rapamycin-inducible bioluminescence in *E. coli*. Notably, the three optimal LCI pairs contained open reading frames that were very similar (NLuc/CLuc combinations of amino acids 2-416/398-550, 2-422/396-550 and 2-432/396-550).

The Ser-Thr kinase mTOR is inhibited by FKBP-12 in a rapamycin-dependent manner (22). The inventors chose FRB, the 11 kD domain of human mTOR that binds with high affinity to the rapamycin-FKBP complex, to construct and screen a comprehensive incremental truncation library for enhanced LCI. Open reading frames for FRB and FKBP were fused in frame with overlapping inactive N- and C-fragments of firefly (Photinus pyralis) luciferase (15, 23), respectively (FIG. 2). From these constructs, N- and C-terminal incremental truncation libraries were generated by unidirectional exonuclease digestion and validated for coverage of all possible deletions essentially as described (18). The FRB-NLuc and CLuc-FKBP incremental truncation libraries were then co-expressed in *E. coli* in the presence of rapamycin to identify pairs of luciferase fragments reconstituting bioluminescence. Of the ~19,000 colonies screened, 123 (0.65%) produced significant bioluminescence (>10-fold over background). Positive clones were subsequently tested for bioluminescence in the presence and absence of rapamycin to identify pairs of luciferase fragments that exhibited strong rapamycin-inducible bioluminescence. Three truncation pairs emerged displaying the strongest rapamycin-inducible increase in bioluminescence in *E. coli*. Notably, the three optimal LCI pairs contained open reading frames that were highly conserved (NLuc/CLuc combinations of amino acids 2-416/398-550, 2-422/396-550 and 2-432/396-550).

Figure 6:
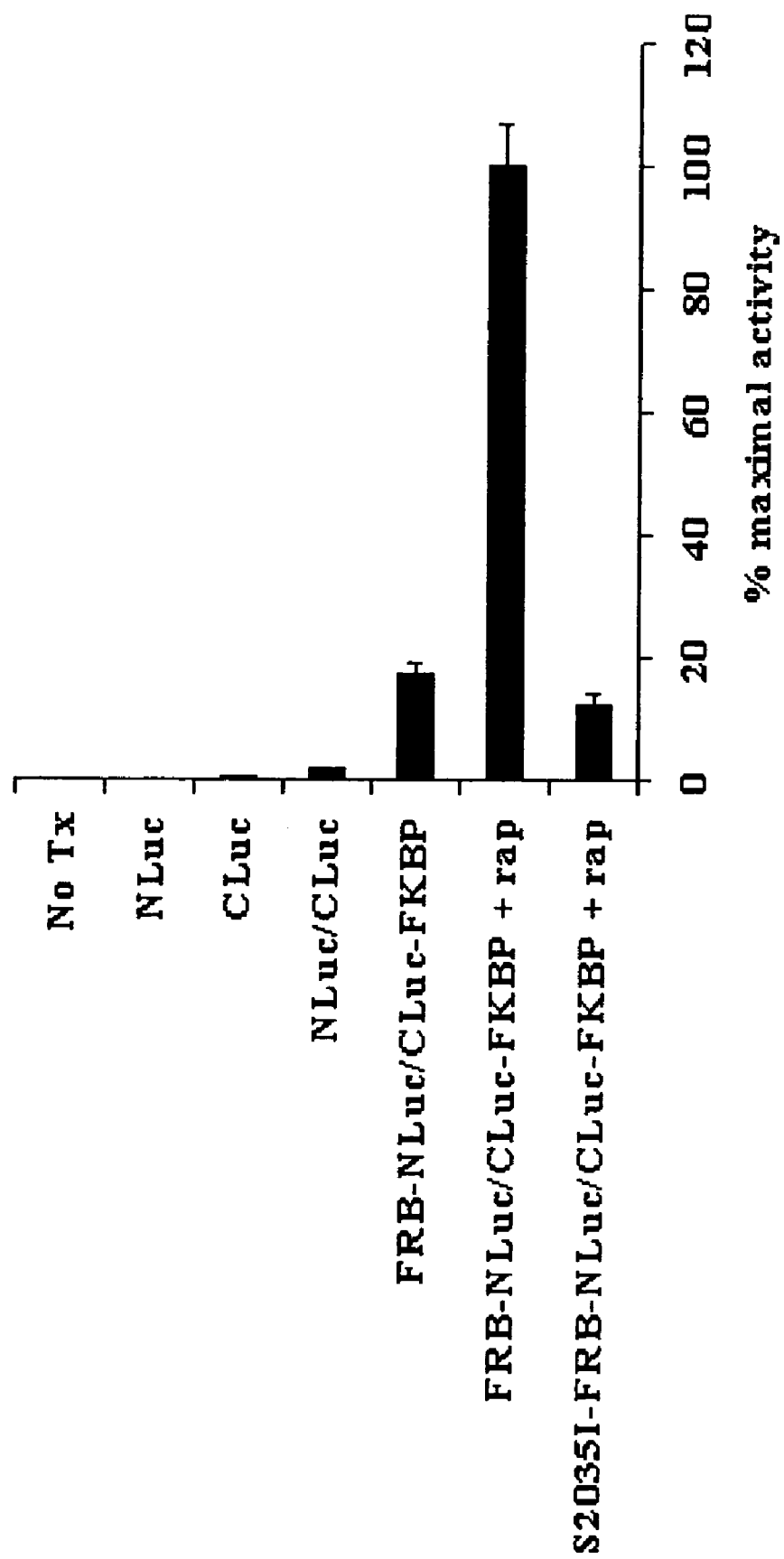
FIG. 6 shows a characterization of FRB-NLuc/CLuc-FKBP LCI in cells. Untransfected HEK-293 cells (no Tx) or cells transfected with various LCI pairs as indicated were treated with vehicle alone or with rapamycin (80 nM) for 6 hrs prior to IVIS imaging. Data are expressed as percent of maximal bioluminescence and represent the mean±SEM of quadruplicate wells.

Rapamycin-induced association of FRB and FKBP. When expressed transiently in HEK-293 cells, the minimal LCI pair (FRB-NLuc(2-416)/CLuc(398-550)-FKBP (FIG. 2), hereafter referred to as FRB-NLuc/CLuc-FKBP) produced strong, rapamycin-induced bioluminescence (FIG. 4). Under optimal transient transfection conditions, FRB-NLuc/CLuc-FKBP plus rapamycin produced a maximal mean signal 72-fold over untransfected cells (FIG. 6). Compared with untreated cells transfected with the FRB-NLuc/CLuc-FKBP LCI pair, rapamycin (80 nM) consistently produced a 6-fold mean maximal increase in bioluminescence within 4-6 hrs (FIG. 6). However, in lysates of similarly transfected cells, bioluminescence induction by rapamycin (80 nM) reached a maximal level 18-fold over untreated lysates of transfected cells within 15 minutes (half-time<1 min; data not shown), suggesting that the membrane permeability of rapamycin limited the kinetics and maximal induction of bioluminescence in intact cells. Furthermore, in intact HEK-293 cells co-expressing the FRB-NLuc/CLuc-FKBP LCI pair, bioluminescence readout displayed single-site rapamycin binding with an apparent $K_d$ of 1.5±0.3 nM (n=3) (FIG. 8), comparable with previously reported FRB-FKBP complementation systems (17, 18). Rapamycin did not alter expression of FRB-NLuc or CLuc-FKBP as assessed by Western blotting (data not shown).

Figure 5:
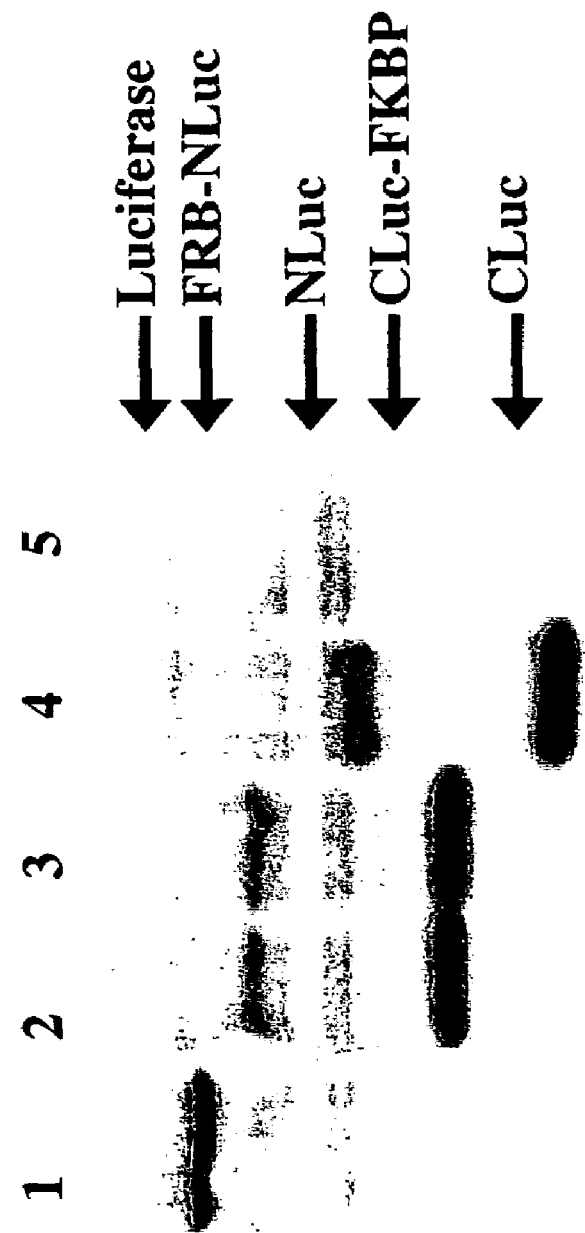
FIG. 5 shows Western blots of whole cell extracts (100 μg protein/lane) from untransfected HEK-293 cells (lane 5) or cells transfected with intact luciferase (lane 1), FRB-NLuc/CLuc-FKBP (lane 2), S2035I FRB-NLuc/CLuc-FKBP (lane 3) or unfused NLuc/CLuc (lane 4). Western blots were probed with a polyclonal anti-luciferase antibody prepared against full length luciferase. (Kindly note that the polyclonal antibody recognizes different epitopes on the NLuc and CLuc fragments so that relative levels of the two fragments cannot be directly assessed.)
Figure 7:
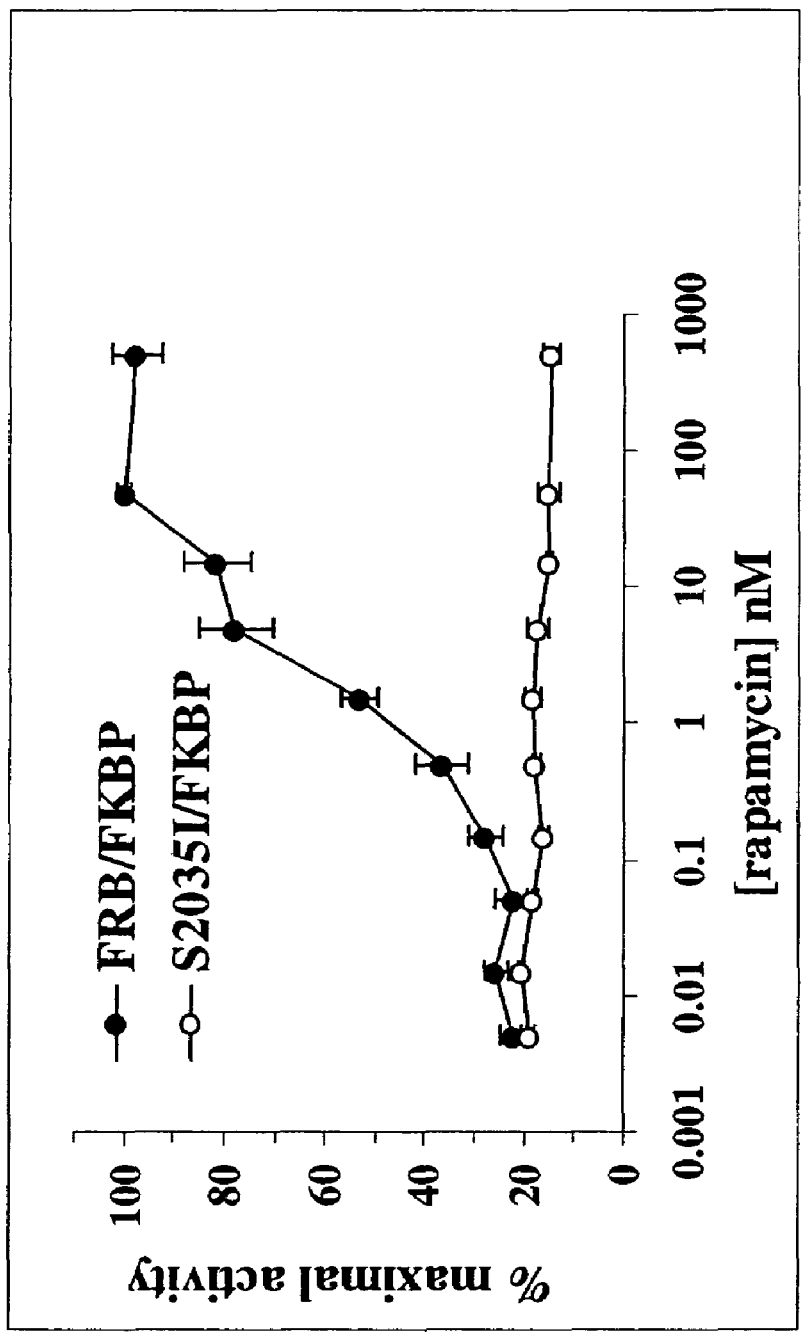
FIG. 7 is a graph of data showing concentration dependence of rapamycin-induced FRB/FKBP association and effect of mutant FRB(S2035I) measured by LCI. HEK-293 cells were transfected with FRB-NLuc/CLuc-FKBP or S2035I FRB-NLuc/CLuc-FKBP and treated with various concentrations of rapamycin for 6 hrs prior to IVIS imaging. Data are expressed as percent of maximal bioluminescence and represent the mean±SEM of quadruplicate wells.
Figure 8:
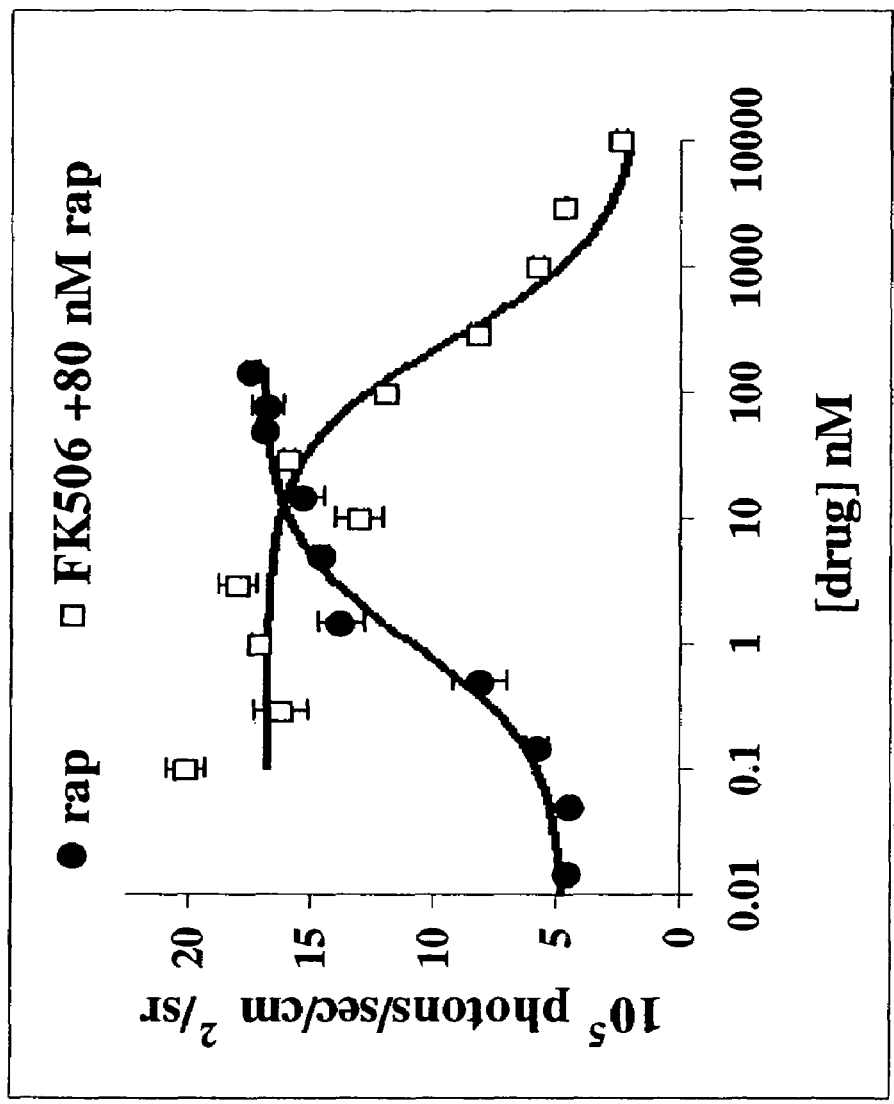
FIG. 8 shows a determination of the apparent $K_d$ of rapamycin-induced as well as $K_i$ of FK506-mediated inhibition of rapamycin-induced FRB/FKBP association in live cells. To assure complete drug permeation, HEK-293 cells transfected with FRB-NLuc/CLuc-FKBP were pretreated 22 hrs prior to LCI with the indicated concentrations of rapamycin alone or with rapamycin at the $EC_{90}$ (80 nM) in the presence of the indicated concentrations of FK506. Data, expressed as mean photon flux±SEM of quadruplicate wells, are representative of three independent tests.

Induction of bioluminescence by rapamycin was saturable and specific in intact HEK-293 cells co-expressing the FRB-NLuc/CLuc-FKBP LCI pair. Displaying single-site rapamycin binding with an apparent $K_d$ of 1.5±0.3 nM (n=3) (FIG. 8), LCI compared favorably with previously reported FRB-FKBP colorimetric and fluorescence-based complementation systems (24, 25). FK506, a competitive inhibitor of rapamycin binding to FKBP (25, 26), inhibited rapamycin-induced luciferase activity in situ with an apparent $K_i$ of 4.2 nM (average value; n=2) (FIG. 8). Furthermore, the S2035I mutation of mTOR is known to abrogate rapamycin-induced association of FKBP with FRB (26). Herein, the S2035I FRB-NLuc/CLuc-FKBP LCI pair produced low, rapamycin-insensitive luciferase activity in live cells similar to FRB-NLuc/CLuc-FKBP in the absence of rapamycin (FIG. 7, 6, 4), consistent with the previously described weak rapamycin-independent association of FRB and FKBP (25, 26). Expression levels of the S2035I FRB-NLuc/CLuc-FKBP pair were identical to FRB-NLuc/CLuc-FKBP as assessed by Western blotting (FIG. 5).

To characterize background bioluminescence, the inventors transfected cells with individual fusion constructs as well as an unfused NLuc/CLuc pair. Individual fusion constructs produced no detectable bioluminescence relative to untransfected cells in both HEK-293 and 293T cells under maximal transfection conditions (FIG. 6 and data not shown), a significant improvement over the activity of N-terminal fragments of firefly luciferase in previously described split enzyme reporters based on naturally occurring domains of luciferase (10, 15). In cells expressing a pair of unfused NLuc and CLuc fragments, dim bioluminescence was observed (FIG. 6). This background due to self-association of the luciferase fragments per se was 12-fold less than the FRB-NLuc/CLuc-FKBP LCI pair in the absence of rapamycin and 100-fold less than the specific signal obtained for the FRB-NLuc/CLuc-FKBP fusion pair in the presence of rapamycin. Western blotting confirmed similar expression levels for all unfused and corresponding fused luciferase fragments (FIG. 5). Overall, these data indicated that the bioluminescence output of this LCI system was dominated by association of the interacting proteins. Furthermore, the quantitative pharmacological titration of rapamycin strongly suggested that the overall free energy contribution of luciferase fragment folding was effectively zero (27).

Figure 9:
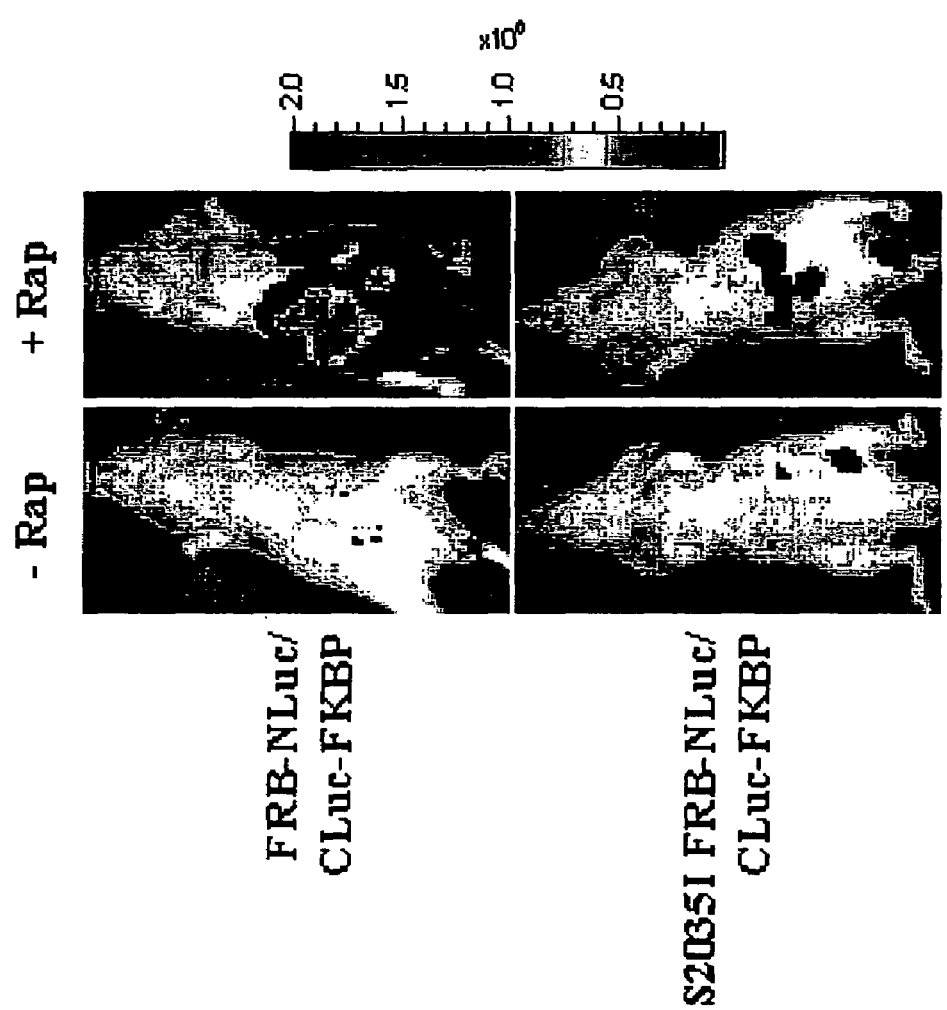
FIG. 9 shows the LCI of two representative nu/nu mice, one implanted with HEK-293 cells expressing FRB-NLuc/CLuc-FKBP (upper panels) and the other with cells expressing mutant S2035I FRB-NLuc/CLuc-FKBP (lower panels). The LCI images were taken 18 hrs prior to treatment with rapamycin (left panels) and 2.5 hrs after receiving a single dose of rapamycin (4.5 mg/kg, i.p.) (right panels).
Figure 10:
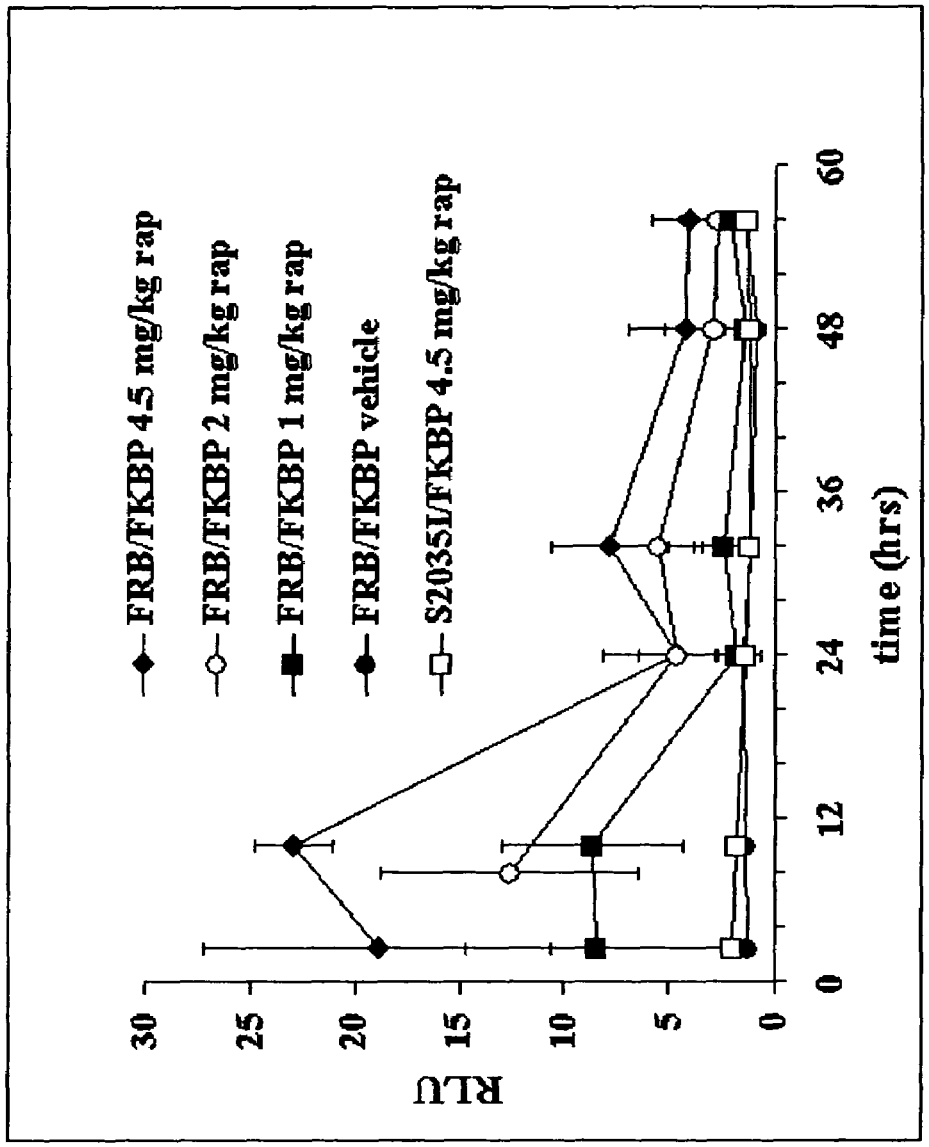
FIG. 10 shows monitoring rapamycin-induced FRB/FKBP association in mice by LCI. At the indicated times after treatment with various doses of rapamycin, mice implanted as above were imaged with an IVIS. Data represent the mean±SEM 4 mice in each group imaged repeatedly over the course of the experiment and are expressed relative to background bioluminescence of unimplanted mice (RLU).

The inventors next applied LCI to pharmacodynamic analysis of rapamycin-induced protein-protein interactions in living mice. The inventors measured luciferase activity in mice with intraperitoneal (i.p.) implants of cells expressing FRB-NLuc/CLuc-FKBP LCI pairs (FIG. 9, 10). In the absence of rapamycin, bioluminescence in implanted mice did not differ from unimplanted mice. Mice treated with a single administration of rapamycin at a dose sufficient to produce anti-angiogenic and antitumor effects (i.p.; 1.0, 2.0 or 4.5 mg/kg) (28) showed dose-dependent increases in bioluminescence with a maximum signal of 23-fold over untreated mice. Induction of bioluminescence by a single dose of rapamycin was maximal 2.5 hrs following treatment, remained high for 10 hours and then decreased by 24 hrs to a low steady state of ~25% of maximum. In contrast, mice implanted with cells expressing mutant S2035I FRB-NLuc/CLuc-FRB showed no detectable signal over background and no response to rapamycin. Interestingly, the kinetics and fold-induction of bioluminescence produced by rapamycin in mouse peritoneal HEK-293 cell implants was similar to cell lysates and both were more rapid and of greater magnitude than for identically transfected HEK-293 cells in tissue culture. Therefore, it seems likely that the pharmacokinetics and cell permeation properties of rapamycin are enhanced in situ in the living animal. LCI produced strong, specific bioluminescence that could be used to repetitively quantify and spatially localize target proteins of interest in a dose- and time-dependent manner in living mice.

Association of Cdc25C with 14-3-3ε.

Figure 11:
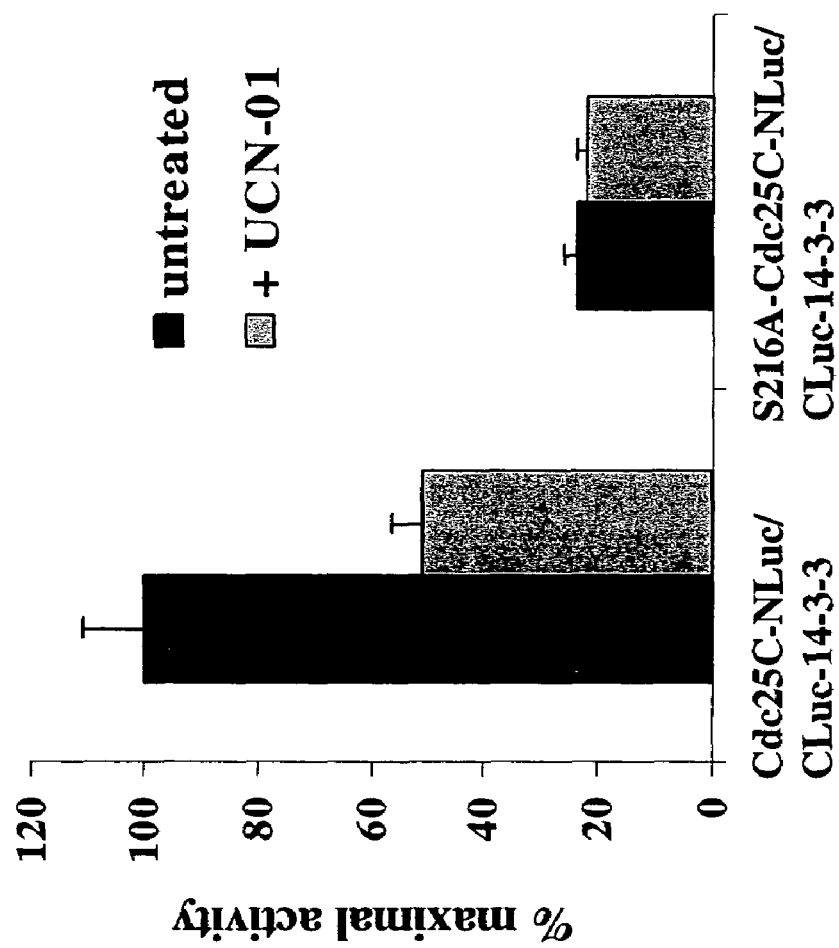
FIG. 11 shows LCI of phospho-serine specific interactions of Cdc25C and 14-3-3ε in cells. HEK-293 cells transfected with Cdc25C-NLuc/CLuc-14-3-3ε or mutant S216A Cdc25C-NLuc/CLuc-14-3-3ε were treated with vehicle alone or UCN-01 (1 μM) for 6 hrs prior to LCI. Data are expressed as percent of bioluminescence relative to untreated Cdc25C-NLuc/CLuc-14-3-3ε in cells and represent the mean±SEM of three independent experiments, n=4 each.
Figure 12:
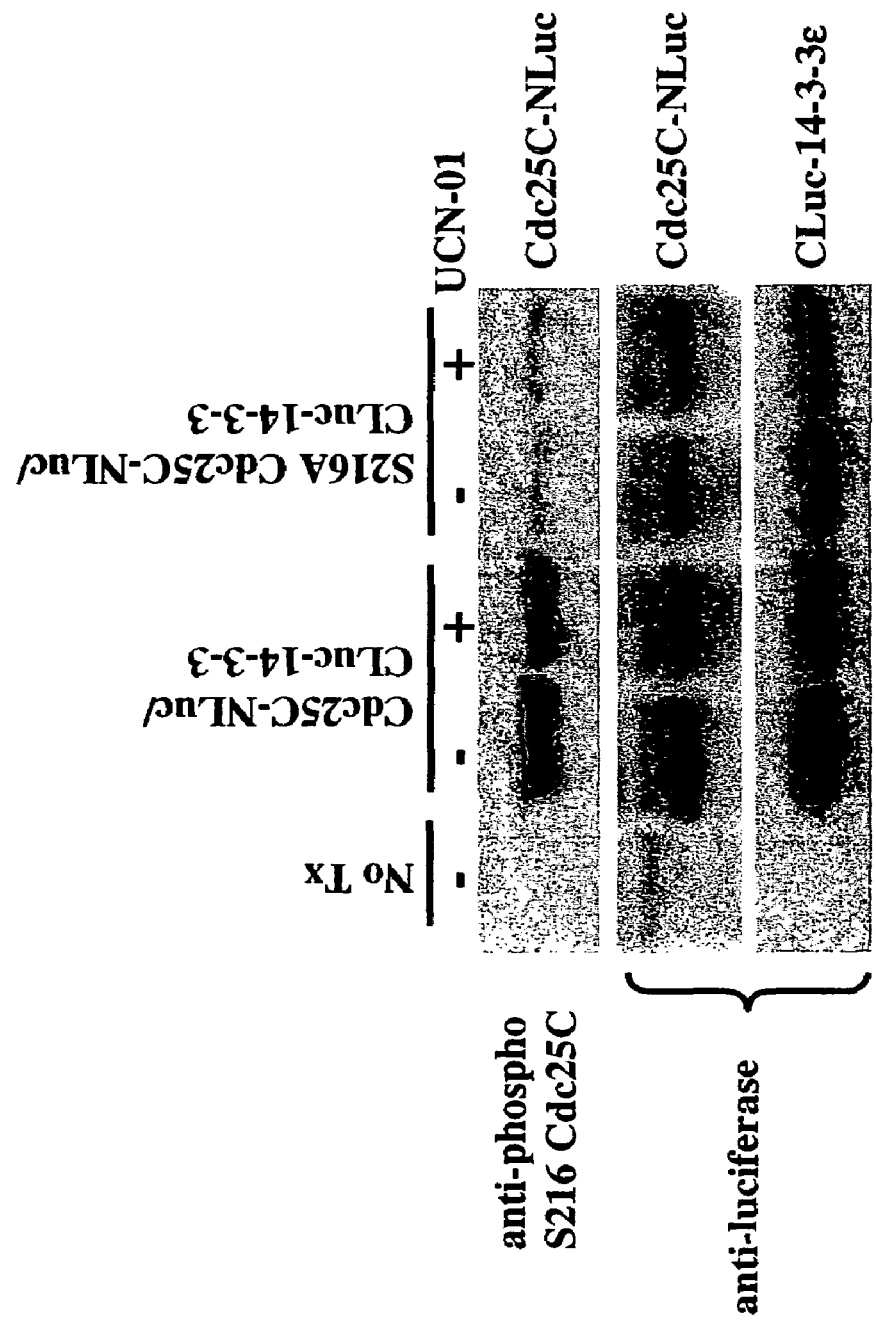
FIG. 12 shows Western blots of untransfected HEK-293 cells (no Tx) or cells transfected with Cdc25C-NLuc/CLuc-14-3-3ε or S216A Cdc25C-NLuc/CLuc-14-3-3ε. Cells were left untreated or treated with UCN-01 (1 μM) for 6 hrs prior to lysis, processed for Western analysis and then probed with the antibodies indicated to visualize expression, phosphorylation, and the effect of UCN-01 on the LCI constructs.

In another illustrative example, LCI was used to monitor the phosphorylation-dependent interactions between human Cdc25C with 14-3-3ε. Cdc25C is a protein phosphatase that positively regulates the cell division cycle by activating cyclin-dependent protein kinases (29). Perturbation of the Cdc25C/14-3-3 regulatory pathway causes partial abrogation of the DNA-replication and DNA damage checkpoints (30). The staurosporine analog UCN-01, a protein kinase inhibitor in phase II clinical trials for cancer treatment, inhibits protein kinases that phosphorylate Cdc25C on S216, thereby diminishing 14-3-3ε binding to Cdc25C (21). In HEK-293 cells co-expressing a Cdc25C-NLuc/CLuc-14-3-3ε LCI pair (FIG. 2), a maximum signal of $1.4 \times 10^6$ photon flux units/$1 \times 10^4$ cells in a 96-well format was obtained (defined as 100% activity) (FIG. 11). This indicated a productive interaction between the Cdc25C and 14-3-3ε fusion proteins. Importantly, the S216A mutation abrogates 14-3-3ε binding to Cdc25C (30) and substantially reduced bioluminescence output (FIG. 11), confirming specificity of the LCI signal. Furthermore, UCN-01 decreased bioluminescence (FIG. 11), correlating with a reduction in phosphorylation of Cdc25C-NLuc on S216 (FIG. 12, lanes 2 and 3). Thus, LCI monitored noninvasively within living cells the activity of protein kinase inhibitors known to block phosphorylation-dependent protein-protein interactions.

STAT1 Homodimerization

Figure 13:
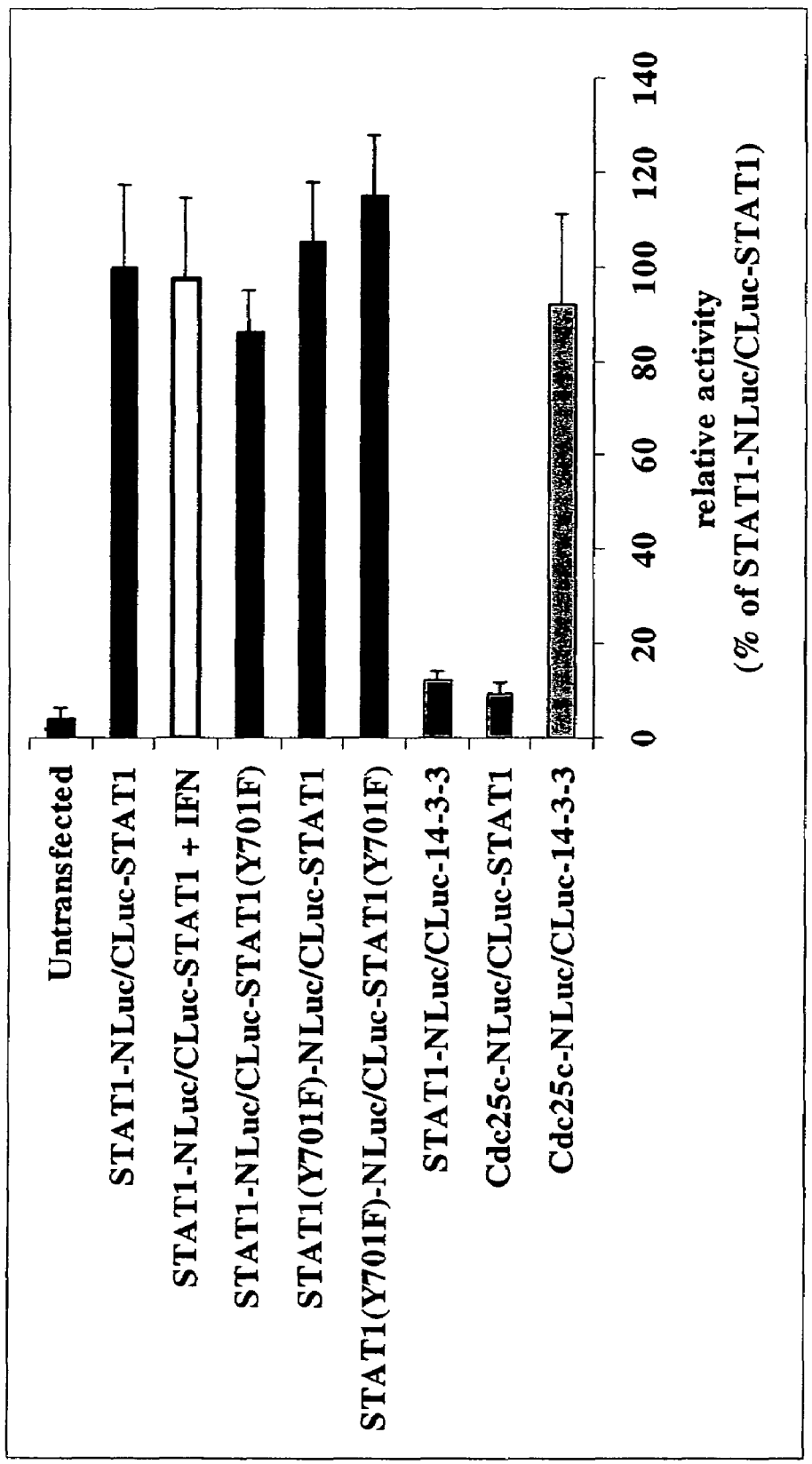
FIG. 13 shows characterization of STAT1-NLuc/CLuc-STAT1 LCI in live cells. Untransfected HEK-293 cells or cells transfected with various LCI pairs are indicated. STAT1/STAT1 pairs were untreated (red bar) or treated with IFN-γ (1000 U/ml) for 30 min (unfilled bar) prior to IVIS imaging. Y701F mutant STAT1 was expressed with wild-type STAT1 or as a mutant pair (black bars). As evidence for specificity of the STAT1/STAT1 interaction, STAT1 fusions were mismatched with Cdc25C or 14-3-3ε fusions (grey bars). The interacting pair Cdc25C-NLuc/CLuc-14-3-3ε (green bar) is included as a positive control. Data are expressed as percent of STAT1-NLuc/CLuc-STAT1 Bioluminescence and represent the mean±SEM (n=4) of a representative experiment.

In another example of utility, LCI was applied to studies of STAT proteins in signal transduction. STAT transcription factors are activated by JAK1-mediated phosphorylation on Y701 in response to IFN-γ (31) and thought to signal through phosphorylation-dependent dimerization of STAT proteins with subsequent translocation of the active dimer to the nucleus (31). However, several recent studies have suggested the existence of a non-phosphorylated pool of STAT dimers (32-35). The inventors applied LCI to directly test for preassociation of non-phosphorylated homodimers of p91 STAT1 in intact cells. Initial tests showed that the STAT1-NLuc/CLuc-STAT1 LCI pair produced strong IFN-γ-independent bioluminescence in HEK-293 cells that was specific for the matched STAT1 LCI pair and not observed with mismatched STAT1 LCI pairs (FIG. 13). In addition, Y701F mutation of the STAT1 reporters resulted in bioluminescence identical to cells transfected with wild-type STAT1 reporters, whether these were expressed as homodimeric mutant pairs or as heterodimers with wild-type STAT1 fusions (FIG. 13).

STAT1 fusions mismatched with Cdc25C-NLuc or CLuc-14-3-3ε (FIG. 13) or mismatched with FRB-NLuc, CLuc-FKBP, NLuc, or CLuc (data not shown) showed low bioluminescence, confirming specificity of the STAT1 homodimeric signal.

Figure 14:
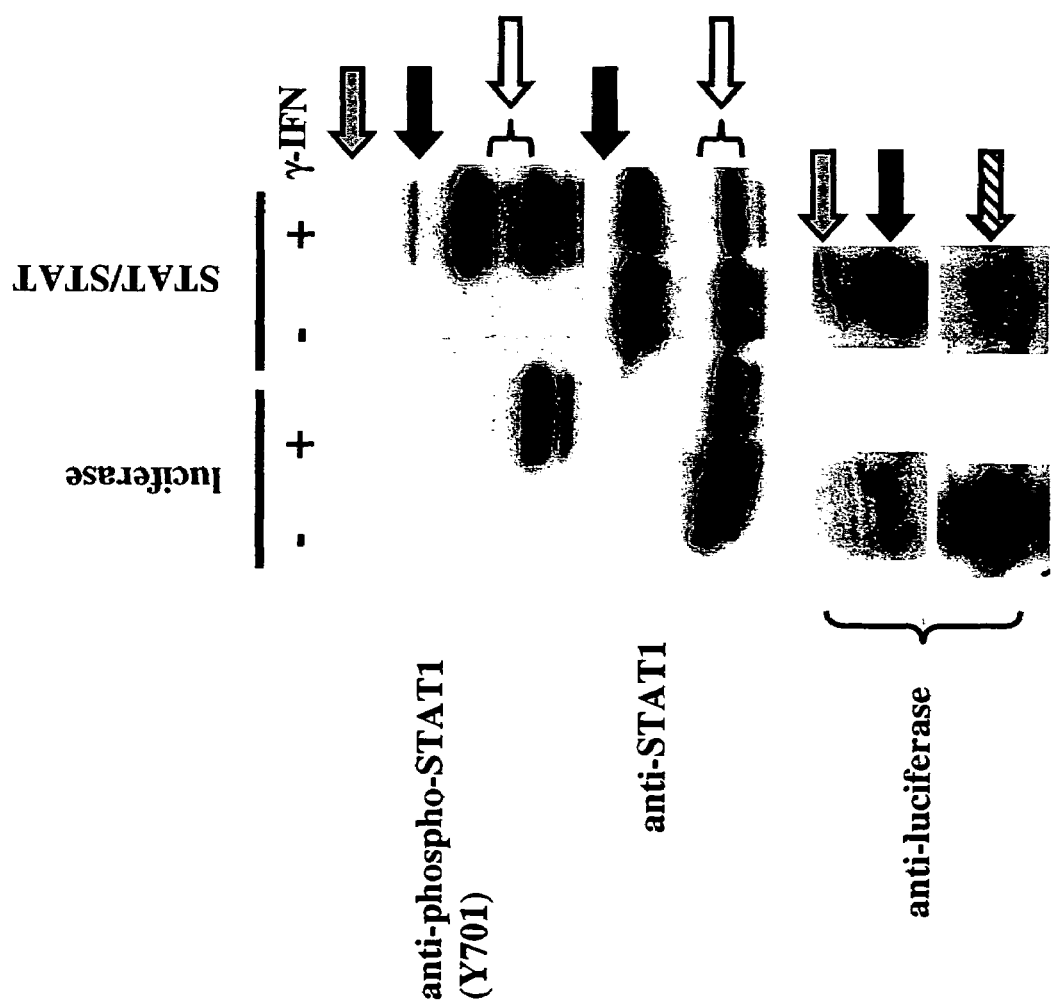
FIG. 14 shows the results of Western blots of whole cell lysates of HEK-293 cells co-transduced with STAT1-NLuc/CLuc-STAT1 lentiviruses or singly transduced with a luciferase lentivirus. Cells were left untreated or treated with IFN-γ (1000 U/ml) for 30 min prior to lysis, processed for Western analysis and then probed with the antibodies indicated to visualize expression and IFN-γ-induced phosphorylation of STAT1-NLuc (grey arrows), CLuc-STAT1 (black arrows), and endogenous p91 and p84 STAT1 (unfilled arrows). Intact luciferase expression (hatched arrow) is also shown. Note that while STAT1-NLuc could not be visualized using the STAT1 antibody, the fusion could be visualized with both Luc and phospho-STAT1 antibodies.

Several possible explanations existed for the persistent bioluminescence of the STAT1 LCI pair. These included constitutive association of unphosphorylated STAT1 reporters, constitutive phosphorylation-dependent association, lack of phosphorylation due to competition by endogenous STATs for JAK1, or inability of JAK1 to recognize one or both of the reporter proteins due to steric bulk of the fused luciferase fragments. For further analysis, the inventors constructed separate lentiviruses expressing STAT1-NLuc or CLuc-STAT1 fusions driven by CMV promotors and co-expressing EGFP or mRFP from an IRES, respectively. HEK-293 cells were infected with STAT1 LCI viral pairs and then sorted by FACS to enrich for co-transduced cells. Similarly, HEK-293 cells infected with a control EGFP-tagged lentivirus encoding intact firefly luciferase were sorted and enriched. Sorted, but untreated transfectants, showed high bioluminescence and Western blotting confirmed expression of both STAT1-NLuc and CLuc-STAT1 proteins, each unphosphorylated on Y701 (FIG. 14, 15). Treatment with IFN-γ resulted in phosphorylation of both STAT1-NLuc and CLuc-STAT1 as well as endogenous p91 and p84 STAT1 (FIG. 14).

Figure 15:
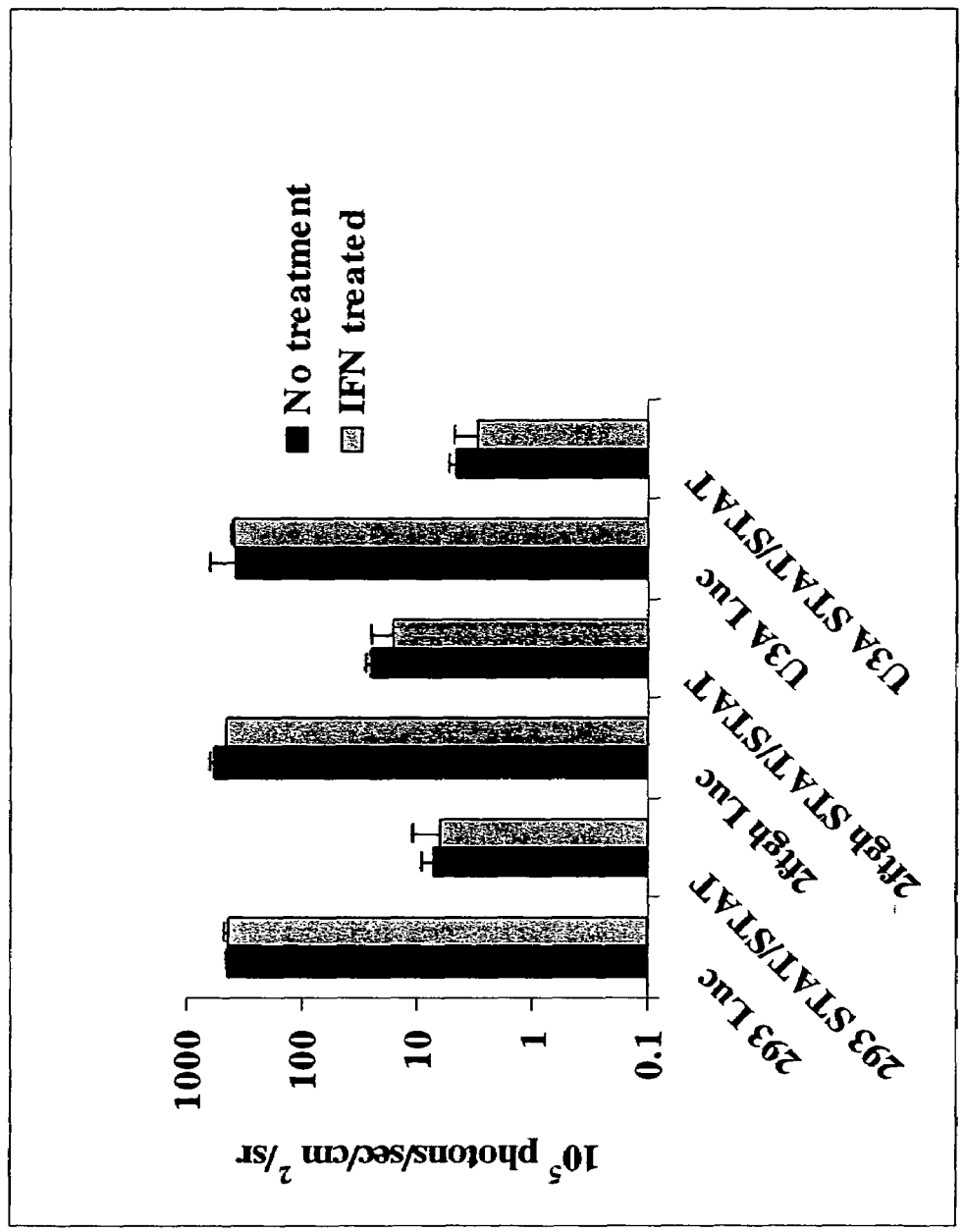
FIG. 15 shows the effect of IFN-γ on bioluminescence of intact cells (HEK-293, 2ftgh, and U3A) transduced with lentiviral constructs expressing STAT1-NLuc/CLuc-STAT1 (STAT1/STAT1) or intact luciferase (Luc). Each transduced cell line was sorted by FACS for expression of appropriate fluorescence markers (EGFP and mRFP) to enrich for cells carrying the imaging constructs. These enriched populations were seeded in a 96-well format (104 cells/well), and left untreated or treated with IFN-δ (1000 U/ml for 30 min). Bars represent the mean +/−SEM (n=4) for a representative test. Note the y-axis log scale.

To investigate competition from endogenous STAT1, the inventors similarly co-transduced and sorted a STAT1-deficient cell line, U3A, and its parental 2ftgh fibrosarcoma cell line (36). While the sorted cell populations showed different levels of constitutive bioluminescence, all co-transduced cells failed to change bioluminescence upon treatment with IFN-γ at any time or at any dose (FIG. 15). Western blots of transduced and sorted U3A and 2ftgh cells were similar in all respects to those shown in FIG. 14 for HEK-293 cells, and confirmed the absence of endogenous STAT1 in U3A cells (data not shown). Thus, the failure of IFN-γ to induce an increase in bioluminescence of the STAT1-NLuc/CLuc-STAT1 pair could not be attributed to competitive inhibition by endogenous STAT1.

Figure 16:
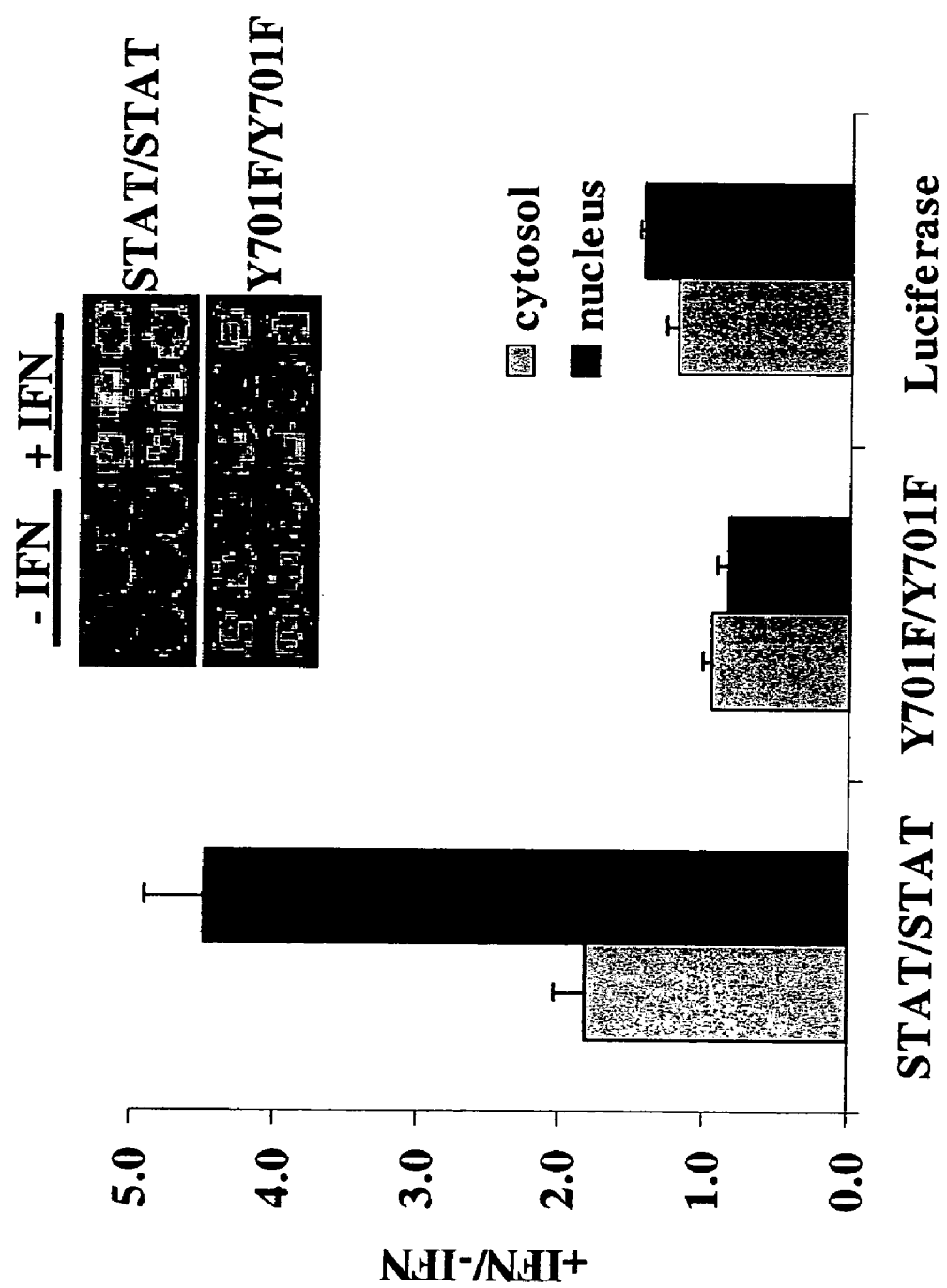
FIG. 16 shows dependence of bioluminescence of cytoplasmic and nuclear extracts on IFN-γ treatment. HEK-293 cells were transiently transfected with STAT1-NLuc/CLuc-STAT1, the Y701F STAT1 mutant LCI pair, or intact luciferase. Forty-eight hours after transfection, cells were left untreated or treated with IFN-γ (1000 U/ml for 20 min) (n=3 for each) and then extracts prepared. To measure bioluminescence in extracts, an assay buffer including D-luciferin and ATP (Luciferase Assay Buffer, Promega, USA) was added to duplicate samples of each extract. Bars show the ratio +/−SEM of mean photon flux/μg protein for extracts of IFN-γ treated over untreated cells. The inset shows raw bioluminescence data for nuclear extracts of cells transfected with the indicated pairs. Duplicate determinations are vertically arranged with independent extracts arrayed horizontally.

To confirm that phosphorylated STAT1 LCI pairs were biologically functional, the inventors measured the IFN-γ-inducible nuclear accumulation of bioluminescence activity. Cytoplasmic and nuclear extracts were prepared from untreated and IFN-γ-treated HEK-293 cells transiently co-transfected with the STAT1-NLuc/CLuc-STAT1 LCI pair, the Y701F mutant pair, or intact luciferase. Bioluminescence (photon flux/μg protein) was specifically increased in nuclear extracts prepared from IFN-γ-treated cells (20 min, 100 U/ml) (FIG. 16). No such IFN-γ-induced increase in nuclear bioluminescence was observed in extracts of cells transfected with the mutant STAT1 LCI pair or intact luciferase. In similar tests, U3A cells co-transduced with the STAT1-NLuc/CLuc-STAT1 LCI pair also showed a 6-fold increase (n=3) in bioluminescence of nuclear extracts (photon flux/μg protein) upon treatment with IFN-γ (30 min, 100 U/ml). Western blots of the cytoplasmic and nuclear extracts used in FIG. 16. confirmed purity of the extracts, neither fraction showing cross-contamination as assessed by the marker proteins β-tubulin (cytoplasm) and Topo II (nucleus), respectively (data not shown). Western blots also confirmed virtually identical expression levels of wild-type and Y701F mutant LCI pairs as well as appropriate phosphorylation of STAT1 proteins and reporters (data not shown).

These data show that the STAT1-NLuc/CLuc-STAT1 LCI pair associated constitutively and specifically in live cells, was appropriately phosphorylated in response to IFN-γ treatment, and that bioluminescent dimers translocated to the nucleus in an IFN-γ-dependent manner. While it is well known that Y701 phosphorylation stabilizes STAT1 homodimers (37), the inventors propose that the behavior of the STAT1 LCI reporter reflected a lower affinity constitutive association of STAT1 that was stabilized and translocated upon Y701 phosphorylation without altering the total pool of low- and high-affinity STAT1 homodimers.

Discussion

Our work shows that LCI can detect and quantify regulated protein interactions in live cells and in whole animals with strong and specific induction of bioluminescence. Once synthesized, LCI hybrid proteins form a complete assay system independent of cell-specific molecular complexes, such as the transcriptional machinery required for readout with two-hybrid strategies (8) and thus, protein interactions may be detectable in any subcellular compartment in near real time. Protein fragment complementation strategies based on reconstituting active enzymes also offer the potential benefit of signal amplification to enhance sensitivity for detecting weaker interacting proteins (8). Herein, the dynamic range of enhanced LCI was robust, with drug-specific induction of bioluminescence reaching 1200-fold over background, exceeding currently available systems. This property enabled lower affinity protein-protein interactions, such as non-phosphorylated STAT1 homodimers, to be characterized in their native state in living cells and may broaden the dynamic range of proteomic studies compared to conventional methods.

A structural explanation for the properties of our optimal LCI pair can be obtained from examination of the fragments within the secondary and tertiary structure of firefly luciferase. The crystal structure of luciferase shows two essentially independent folding domains, the N-terminal domain consisting of residues 1-436 and a C-terminal domain of residues 440-550, connected by a disordered flexible region (38). The active site is considered to be in a cleft between these two domains, enclosing the substrate and excluding water during the reaction. Interestingly, our genetic screen selected an LCI pair for productive interaction-induced activity that fulfilled many criteria of complementary fragments derived from rational protein design applied to other enzymes (27). The enhanced LCI pair deleted key structural and active site regions from the N-terminal fragment and, in effect, transferred these regions to the C-terminal fragment (38). The NLuc fragment would be unlikely to adopt an entirely native fold because the core of a β-barrel subdomain is missing, including β-strands C5 and C6 (residues 418-437) containing several invariant and highly conserved residues of the putative active site. Upon interaction, the CLuc fragment would complement the missing subdomains in the NLuc fragment, including a region of overlap (398-416) encompassing β-strand 8 and helix 12 of subdomain A.

While enhanced LCI appears to be broadly adaptable, steric constraints of the system remain to be fully explored. Herein, LCI applications to drug-induced association of heterodimeric complexes (FRB/FKBP), phospho-dependent association of heterodimeric complexes (Cdc25C/14-3-3ε), and ligand-induced translocation of homodimeric complexes (STAT1/STAT1) demonstrated high sensitivity to regulation at the post-translational level in situ and in vitro. LCI showed no background bioluminescence arising from individual LCI fragments and minimal bioluminescence arising from unregulated association of the firefly luciferase fragments themselves. Thus, this novel LCI system may finally prove useful for assessing interactions of proteins in live animals in the context of normal function and disease. Enhanced LCI provides a promising new tool for high throughput screening, direct and indirect quantification of drug binding to specific protein targets, and noninvasively characterizing mechanisms of therapeutic response in living organisms.

Our discovery can be used to study cellular processes such as signal transduction and to screen for test compounds which modulate protein-protein activity which may have mammalistic therapeutic potential. Other protein fragment complementation systems for study of protein-protein interactions only work in vitro or with cell lysates. Other strategies require a fluorescence microscope for readout. None of the known protein fragment complementation technologies enable protein-protein interactions to be non-invasively visualized in intact cells or living animals, except for luciferase. There exists two prior luciferase fragment pairs in the literature. However, one prior pair shows high background bioluminescence from the N-terminal fragment alone, severely limiting its application, while the other is based on Renilla luciferase which emits blue-green, a spectral range not useful for use in vivo. Furthermore, it has not been demonstrated with the prior pairs that small molecule-inducible complementation could be accomplished. Our newly discovered firefly luciferase fragments are unique, could not be predicted based on the crystal structure of the luciferase protein, and importantly, show no bioluminescence when each fragment is expressed alone or when each fragment is fused to an inducible protein binding partner, but in the absence of an inducer. Thus, background activity of our pair is very low, representing a major improvement over the prior art. For example, in studies with the FRB-NLuc/CLuc-FKBP LCI pair, in the absence of the inducer (rapamycin), bioluminescence in implanted mice did not differ from unimplanted mice.

In an aspect a method of detecting the interaction of a first and second protein is carried out in a test sample housed in a container, the test sample comprising cellular ingredients supporting and sustaining the living cell and a protein fused to one luciferase fragment of a pair of firefly luciferase fragments the pair having low background bioluminescence that upon reconstitution capably provides an active biolumiscent moiety, in proximity to another protein fused to the other companion respective luciferase fragment, wherein binding or interaction of the two proteins results in reconstitution of luciferase and detecting such interaction by determining the level of bioluminescence. In an aspect such determining/determination is carried out by measuring luminescence with a luminometer. In that regard conditions are effective to permit protein to protein interaction.

Useful luminometers include those from Turner BioSystems, such as the 20/20 n luminometer, Veritas ™ Microplate Luminometer, TD-20/20 Single tube luminometer, Reporter Multiwell plate luminometer and the GloRunner multiwell plate luminometer, as well as the xenogen IVIS bioluminescence imaging system.

As will be appreciated those constructs, expression vectors and the like which are prepared in a part of this discovery, are isolated, recovered and utliyzed in another part in order to successfully practice this discovery. Those of skill in the art will be able to carry this out after reading the specification and claims and drawings.

This discovery is additionally useful in assessing the status of compounds with regard to whether or not the compound is to remain in a screening program or to promoted or advance in such a screening program because of activity of the compound. The ability to make continual assessment of the viability of a compound in an evaluation program is of utmost importance in today's competitive environment for discovering and bringing drugs to the market. Today's strategy requires high throughput determinative screens such as this discovery. The paradigm is one of volume and accuracy. The capability to make such prioritizations will mean that a cancer type candidate drug showing activity in such a screen as this discovery will be rapidly advance in prioritization over other drugs not showing such activity.

While the discovery has been described in terms of various specific embodiments, those skilled in the art will recognize that the discovery can be practiced with modification within the spirit and scope of the claims.

Sequence listings:

```
Seq Id. No 1 FRB-NLuc:
GACGGATCGGGAGATCTCCCGATCCCCTATGGTCGACTCTCAGTACAATCTGCTCTGAT       SEQ ID 1

GCCGCATAGTTAAGCCAGTATCTGCTCCCTGCTTGTGTGTTGGAGGTCGCTGAGTAGTG

CGCGAGCAAAATTTAAGCTACAACAAGGCAAGGCTTGACCGACAATTGCATGAAGAATCT

GCTTAGGGTTAGGCGTTTTGCGCTGCTTCGCGATGTACGGGCCAGATATACGCGTTGAC

ATTGATTATTGACTAGTTATTAATAGTAATCAATTACGGGGTCATTAGTTCATAGCCCATA

TATGGAGTTCCGCGTTACATAACTTACGGTAAATGGCCCGCCTGGCTGACCGCCCAACG

ACCCCCGCCCATTGACGTCAATAATGACGTATGTTCCCATAGTAACGCCAATAGGGACTT

TCCATTGACGTCAATGGGTGGACTATTTACGGTAAACTGCCCACTTGGCAGTACATCAAG

TGTATCATATGCCAAGTACGCCCCCTATTGACGTCAATGACGGTAAATGGCCCGCCTGG

CATTATGCCCAGTACATGACCTTATGGGACTTTCCTACTTGGCAGTACATCTACGTATTA

GTCATCGCTATTACCATGGTGATGCGGTTTTGGCAGTACATCAATGGGCGTGGATAGCG

GTTTGACTCACGGGGATTTCCAAGTCTCCACCCCATTGACGTCAATGGGAGTTTGTTTTG

GCACCAAAATCAACGGGACTTTCCAAAATGTCGTAACAACTCCGCCCCATTGACGCAAAT

GGGCGGTAGGCGTGTACGGTGGGAGGTCTATATAAGCAGAGCTCTCTGGCTAACTAGA

GAACCCACTGCTTACTGGCTTATCGAAATTAATACGACTCACTATAGGGAGACCCAAGCT
```

-continued

```
GGCTAGTTAAGCTTGGTACCGAGCTCGGATCCACTAGTCCAGTGTGGTGGAATTGCCCT
TACACCACCatgGAGATGTGGCATGAAGGCCTGGAAGAGGCATCTCGTTTGTACTTTGGG
GAAAGGAACGTGAAAGGCATGTTTGAGGTGCTGGAGCCCTTGCATGCTATGATGGAACG
GGGCCCCCAGACTCTGAAGGAAACATCCTTTAATCAGGCCTATGGTCGAGATTTAATGG
AGGCCCAAGAGTGGTGCAGGAAGTACATGAAATCAGGGAATGTCAAGGACCTCACCCAA
GCCTGGGACCTCTATTATCATGTGTTCCGACGAATCTCAAAGCAGCAGATCTCGTACGC
GTCCCGGGGCGGTGGCTCATCTGGCGGAGGTGAAGACGCCAAAAACATAAAGAAAGGC
CCGGCGCCATTCTATCCGCTGGAAGATGGAACCGCTGGAGAGCAACTGCATAAGGCTAT
GAAGAGATACGCCCTGGTTCCTGGAACAATTGCTTTTACAGATGCACATATCGAGGTGG
ACATCACTTACGCTGAGTACTTCGAAATGTCCGTTCGGTTGGCAGAAGCTATGAAACGAT
ATGGGCTGAATACAAATCACAGAATCGTCGTATGCAGTGAAAACTCTCTTCAATTCTTTAT
GCCGGTGTTGGGCGCGTTATTTATCGGAGTTGCAGTTGCGCCCGCGAACGACATTTATA
ATGAACGTGAATTGCTCAACAGTATGGGCATTTCGCAGCCTACCGTGGTGTTCGTTTCC
AAAAAGGGGTTGCAAAAAATTTTGAACGTGCAAAAAAAGCTCCCAATCATCCAAAAAATTA
TTATCATGGATTCTAAAACGGATTACCAGGGATTTCAGTCGATGTACACGTTCGTCACAT
CTCATCTACCTCCCGGTTTTAATGAATACGATTTTGTGCCAGAGTCCTTCGATAGGGACA
AGACAATTGCACTGATCATGAACTCCTCTGGATCTACTGGTCTGCCTAAAGGTGTCGCTC
TGCCTCATAGAACTGCCTGCGTGAGATTCTCGCATGCCAGAGATCCTATTTTTGGCAATC
AAATCATTCCGGATACTGCGATTTTAAGTGTTGTTCCATTCCATCACGGTTTTGGAATGTT
TACTACACTCGGATATTTGATATGTGGATTTCGAGTCGTCTTAATGTATAGATTTGAAGAA
GAGCTGTTTCTGAGGAGCCTTCAGGATTACAAGATTCAAAGTGCGCTGCTGGTGCCAAC
CCTATTCTCCTTCTTCGCCAAAAGCACTCTGATTGACAAATACGATTTATCTAATTTACAC
GAAATTGCTTCTGGTGGCGCTCCCCTCTCTAAGGAAGTCGGGGAAGCGGTTGCCAAGA
GGTTCCATCTGCCAGGTATCAGGCAAGGATATGGGCTCACTGAGACTACATCAGCTATT
CTGATTACACCCGAGGGGGATGATAAACCGGGCGCGGTCGGTAAAGTTGTTCCATTTTT
TGAAGCGAAGGTTGTGGATCTGGATACCGGGAAAACGCTGGGCGTTAATCAAAGAGGC
GAACTGTGTGTGAGAGGTCCTATGATTATGTCCGGTTATGTAAACAATCCGGAAGCGAC
CAACGCCTTGATTGACAAGGATGGATGATAACATTCTGGtagCTAGGTAATGCATAACTAG
CTAAGGTACCCAATTAAGGGCAATTCTGCAGATATCCAGCACAGTGGCGGCCGCTCGAG
TCTAGAGGGCCCGCGGTTCGAAGGTAAGCCTATCCCTAACCCTCTCCTCGGTCTCGATT
CTACGCGTACCGGTCATCATCACCATCACCATTGAGTTTAAACCCGCTGATCAGCCTCG
ACTGTGCCTTCTAGTTGCCAGCCATCTGTTGTTTGCCCCTCCCCCGTGCCTTCCTTGAC
CCTGGAAGGTGCCACTCCCACTGTCCTTTCCTAATAAAATGAGGAAATTGCATCGCATTG
TCTGAGTAGGTGTCATTCTATTCTGGGGGGTGGGGTGGGCAGGACAGCAAGGGGGA
GGATTGGGAAGACAATAGCAGGCATGCTGGGGATGCGGTGGGCTCTATGGCTTCTGAG
GCGGAAAGAACCAGCTGGGGCTCTAGGGGGTATCCCCACGCGCCCTGTAGCGGCGCA
TTAAGCGCGGCGGGTGTGGTGGTTACGCGCAGCGTGACCGCTACACTTGCCAGCGCCC
TAGCGCCCGCTCCTTTCGCTTTCTTCCCTTCCTTTCTCGCCACGTTCGCCGGCTTTCCC
CGTCAAGCTCTAAATCGGGGCATCCCTTTAGGGTTCCGATTTAGTGCTTTACGGCACCT
CGACCCCAAAAAACTTGATTAGGGTGATGGTTCACGTAGTGGGCCATCGCCCTGATAGA
```

-continued

```
CGGTTTTTCGCCCTTTGACGTTGGAGTCCACGTTCTTTAATAGTGGACTCTTGTTCCAAA
CTGGAACAACACTCAACCCTATCTCGGTCTATTCTTTTGATTTATAAGGGATTTTGGGGA
TTTCGGCCTATTGGTTAAAAAATGAGCTGATTTAACAAAAATTTAACGCGAATTAATTCTG
TGGAATGTGTGTCAGTTAGGGTGTGGAAAGTCCCCAGGCTCCCCAGGCAGGCAGAAGT
ATGCAAAGCATGCATCTCAATTAGTCAGCAACCAGGTGTGGAAAGTCCCCAGGCTCCCC
AGCAGGCAGAAGTATGCAAAGCATGCATCTCAATTAGTCAGCAACCATAGTCCCGCCCC
TAACTCCGCCCATCCCGCCCCTAACTCCGCCCAGTTCCGCCCATTCTCCGCCCCATGGC
TGACTAATTTTTTTATTTATGCAGAGGCCGAGGCCGCCTCTGCCTCTGAGCTATTCCAG
AAGTAGTGAGGAGGCTTTTTTGGAGGCCTAGGCTTTTGCAAAAAGCTCCCGGGAGCTTG
TATATCCATTTTCGGATCTGATCAAGAGACAGGATGAGGATCGTTTCGCATGATTGAACA
AGATGGATTGCACGCAGGTTCTCCGGCCGCTTGGGTGGAGAGGCTATTCGGCTATGAC
TGGGCACAACAGACAATCGGCTGCTCTGATGCCGCCGTGTTCCGGCTGTCAGCGCAGG
GGCGCCCGGTTCTTTTTGTCAAGACCGACCTGTCCGGTGCCCTGAATGAACTGCAGGA
CGAGGCAGCGCGGCTATCGTGGCTGGCCACGACGGGCGTTCCTTGCGCAGCTGTGCT
CGACGTTGTCACTGAAGCGGGAAGGGACTGGCTGCTATTGGGCGAAGTGCCGGGGCA
GGATCTCCTGTCATCTCACCTTGCTCCTGCCGAGAAAGTATCCATCATGGCTGATGCAAT
GCGGCGGCTGCATACGCTTGATCCGGCTACCTGCCCATTCGACCACCAAGCGAAACAT
CGCATCGAGCGAGCACGTACTCGGATGGAAGCCGGTCTTGTCGATCAGGATGATCTGG
ACGAAGAGCATCAGGGGCTCGCGCCAGCCGAACTGTTCGCCAGGCTCAAGGCGCGCAT
GCCCGACGGCGAGGATCTCGTCGTGACCCATGGCGATGCCTGCTTGCCGAATATCATG
GTGGAAAATGGCCGCTTTTCTGGATTCATCGACTGTGGCCGGCTGGGTGTGGCGGACC
GCTATCAGGACATAGCGTTGGCTACCCGTGATATTGCTGAAGAGCTTGGCGGCGAATG
GGCTGACCGCTTCCTCGTGCTTTACGGTATCGCCGCTCCCGATTCGCAGCGCATCGCC
TTCTATCGCCTTCTTGACGAGTTCTTCTGAGCGGGACTCTGGGGTTCGCGAAATGACCG
ACCAAGCGACGCCCAACCTGCCATCACGAGATTTCGATTCCACCGCCGCCTTCTATGAA
AGGTTGGGCTTCGGAATCGTTTTCCGGGACGCCGGCTGGATGATCCTCCAGCGCGGGG
ATCTCATGCTGGAGTTCTTCGCCCACCCCAACTTGTTTATTGCAGCTTATAATGGTTACA
AATAAAGCAATAGCATCACAAATTTCACAAATAAAGCATTTTTTTCACTGCATTCTAGTTGT
GGTTTGTCCAAACTCATCAATGTATCTTATCATGTCTGTATACCGTCGACCTCTAGCTAG
AGCTTGGCGTAATCATGGTCATAGCTGTTTCCTGTGTGAAATTGTTATCCGCTCACAATT
CCACACAACATACGAGCCGGAAGCATAAAGTGTAAAGCCTGGGGTGCCTAATGAGTGAG
CTAACTCACATTAATTGCGTTGCGCTCACTGCCCGCTTTCCAGTCGGGAAACCTGTCGT
GCCAGCTGCATTAATGAATCGGCCAACGCGCGGGGAGAGGCGGTTTGCGTATTGGGCG
CTCTTCCGCTTCCTCGCTCACTGACTCGCTGCGCTCGGTCGTTCGGCTGCGGCGAGCG
GTATCAGCTCACTCAAAGGCGGTAATACGGTTATCCACAGAATCAGGGGATAACGCAGG
AAAGAACATGTGAGCAAAAGGCCAGCAAAAGGCCAGGAACCGTAAAAAGGCCGCGTTG
CTGGCGTTTTTCCATAGGCTCCGCCCCCCTGACGAGCATCACAAAAATCGACGCTCAAG
TCAGAGGTGGCGAAACCCGACAGGACTATAAAGATACCAGGCGTTTCCCCCTGGAAGCT
CCCTCGTGCGCTCTCCTGTTCCGACCCTGCCGCTTACCGGATACCTGTCCGCCTTTCTC
CCTTCGGGAAGCGTGGCGCTTTCTCAATGCTCACGCTGTAGGTATCTCAGTTCGGTGTA
```

-continued

```
GGTCGTTCGCTCCAAGCTGGGCTGTGTGCACGAACCCCCGTTCAGCCCGACCGCTGC
GCCTTATCCGGTAACTATCGTCTTGAGTCCAACCCGGTAAGACACGACTTATCGCCACT
GGCAGCAGCCACTGGTAACAGGATTAGCAGAGCGAGGTATGTAGGCGGTGCTACAGAG
TTCTTGAAGTGGTGGCCTAACTACGGCTACACTAGAAGGACAGTATTTGGTATCTGCGC
TCTGCTGAAGCCAGTTACCTTCGGAAAAAGAGTTGGTAGCTCTTGATCCGGCAAACAAA
CCACCGCTGGTAGCGGTGGTTTTTTTGTTTGCAAGCAGCAGATTACGCGCAGAAAAAA
GGATCTCAAGAAGATCCTTTGATCTTTTCTACGGGGTCTGACGCTCAGTGGAACGAAAA
CTCACGTTAAGGGATTTTGGTCATGAGATTATCAAAAAGGATCTTCACCTAGATCCTTTTA
AATTAAAAATGAAGTTTTAAATCAATCTAAAGTATATATGAGTAAACTTGGTCTGACAGTTA
CCAATGCTTAATCAGTGAGGCACCTATCTCAGCGATCTGTCTATTTCGTTCATCCATAGT
TGCCTGACTCCCCGTCGTGTAGATAACTACGATACGGGAGGGCTTACCATCTGGCCCCA
GTGCTGCAATGATACCGCGAGACCCACGCTCACCGGCTCCAGATTTATCAGCAATAAAC
CAGCCAGCCGGAAGGGCCGAGCGCAGAAGTGGTCCTGCAACTTTATCCGCCTCCATCC
AGTCTATTAATTGTTGCCGGGAAGCTAGAGTAAGTAGTTCGCCAGTTAATAGTTTGCGCA
ACGTTGTTGCCATTGCTACAGGCATCGTGGTGTCACGCTCGTCGTTTGGTATGGCTTCA
TTCAGCTCCGGTTCCCAACGATCAAGGCGAGTTACATGATCCCCCATGTTGTGCAAAAA
AGCGGTTAGCTCCTTCGGTCCTCCGATCGTTGTCAGAAGTAAGTTGGCCGCAGTGTTAT
CACTCATGGTTATGGCAGCACTGCATAATTCTCTTACTGTCATGCCATCCGTAAGATGCT
TTTCTGTGACTGGTGAGTACTCAACCAAGTCATTCTGAGAATAGTGTATGCGGCGACCG
AGTTGCTCTTGCCCGGCGTCAATACGGGATAATACCGCGCCACATAGCAGAACTTTAAA
AGTGCTCATCATTGGAAAACGTTCTTCGGGGCGAAAACTCTCAAGGATCTTACCGCTGTT
GAGATCCAGTTCGATGTAACCCACTCGTGCACCCAACTGATCTTCAGCATCTTTTACTTT
CACCAGCGTTTCTGGGTGAGCAAAAACAGGAAGGCAAAATGCCGCAAAAAAGGGAATAA
GGGCGACACGGAAATGTTGAATACTCATACTCTTCCTTTTTCAATATTATTGAAGCATTTA
TCAGGGTTATTGTCTCATGAGCGGATACATATTTGAATGTATTTAGAAAAATAAACAAATA
GGGGTTCCGCGCACATTTCCCCGAAAAGTGCCACCTGACGTC
Seq Id. No 2 CLuc-FKBP:
AATATTATTGAAGCATTTATCAGGGTTATTGTCTCATGAGCGGATACATATTTGAATGTAT   SEQ ID 2
TTAGAAAAATAAACAAATAGGGGTTCCGCGCACATTTCCCCGAAAAGTGCCACCTGACGT
CGACGGATCGGGAGATCTCCCGATCCCCTATGGTCGACTCTCAGTACAATCTGCTCTGA
TGCCGCATAGTTAAGCCAGTATCTGCTCCCTGCTTGTGTGTTGGAGGTCGCTGAGTAGT
GCGCGAGCAAAATTTAAGCTACAACAAGGCAAGGCTTGACCGACAATTGCATGAAGAAT
CTGCTTAGGGTTAGGCGTTTTGCGCTGCTTCGCGATGTACGGGCCAGATATACGCGTTG
ACATTGATTATTGACTAGGCTTTTGCAAAAAGCTTTGCAAAGATGGATAAAGTTTTAAACA
GAGAGGAATCTTTGCAGCTAATGGACCTTCTAGGTCTTGAAAGGAGTGCCTCGTGAGGC
TCCGGTGCCCGTCAGTGGGCAGAGCGCACATCGCCCACAGTCCCCGAGAAGTTGGGG
GGAGGGGTCGGCAATTGAACCGGTGCCTAGAGAAGGTGGCGCGGGGTAAACTGGGAA
AGTGATGTCGTGTACTGGCTCCGCCTTTTTCCCGAGGGTGGGGGAGAACCGTATATAAG
TGCAGTAGTCGCCGTGAACGTTCTTTTTCGCAACGGGTTTGCCGCCAGAACACAGGTAA
GTGCCGTGTGTGGTTCCCGCGGGCCTGGCCTCTTTACGGGTTATGGCCCTTGCGTGCC
```

-continued

```
TTGAATTACTTCCACCTGGCTGCAGTACGTGATTCTTGATCCCGAGCTTCGGGTTGGAA
GTGGGTGGGAGAGTTCGAGGCCTTGCGCTTAAGGAGCCCCTTCGCCTCGTGCTTGAGT
TGAGGCCTGGCCTGGGCGCTGGGGCCGCCGCGTGCGAATCTGGTGGCACCTTCGCGC
CTGTCTCGCTGCTTTCGATAAGTCTCTAGCCATTTAAAATTTTTGATGACCTGCTGCGAC
GCTTTTTTTCTGGCAAGATAGTCTTGTAAATGCGGGCCAAGATCTGCACACTGGTATTTC
GGTTTTTGGGGCCGCGGGCGGCGACGGGGCCCGTGCGTCCCAGCGCACATGTTCGGC
GAGGCGGGGCCTGCGAGCGCGGCCACCGAGAATCGGACGGGGGTAGTCTCAAGCTGG
CCGGCCTGCTCTGGTGCCTGGCCTCGCGCCGCCGTGTATCGCCCCGCCCTGGGCGGC
AAGGCTGGCCCGGTCGGCACCAGTTGCGTGAGCGGAAAGATGGCCGCTTCCCGGCCC
TGCTGCAGGGAGCTCAAAATGGAGGACGCGGCGCTCGGGAGAGCGGGCGGGTGAGTC
ACCCACACAAAGGAAAAGGGCCTTTCCGTCCTCAGCCGTCGCTTCATGTGACTCCACGG
AGTACCGGGCGCCGTCCAGGCACCTCGATTAGTTCTCGAGCTTTTGGAGTACGTCGTCT
TTAGGTTGGGGGAGGGGTTTTATGCGATGGAGTTTCCCCACACTGAGTGGGTGGAGA
CTGAAGTTAGGCCAGCTTGGCACTTGATGTAATTCTCCTTGGAATTTGCCCTTTTTGAGT
TTGGATCTTGGTTCATTCTCAAGCCTCAGACAGTGGTTCAAAGTTTTTTTCTTCCATTTCA
GGTGTCGTGAGGAATTAGCTTGGTACTAATACGACTCACTATAGGGAGACCCAAGCTGG
CTAGGTAAGCTTGGTACCGAGCTCGGATCCACTAGTCCAGTGTGGTGGAATTGCCCTTA
CACCACCatgTCCGGTTATGTAAACAATCCGGAAGCGACCAACGCCTTGATTGACAAGGA
TGGATGGCTACATTCTGGAGACATAGCTTACTGGGACGAAGACGAACACTTCTTCATCG
TTGACCGCTGAAGTCTCTGATTAAGTACAAAGGCTATCAGGTGGCTCCCGCTGAATTG
GAATCCATCTTGCTCCAACACCCCAACATCTTCGACGCAGGTGTCGCAGGTCTTCCCGA
CGATGACGCCGGTGAACTTCCCGCCGCCGTTGTTGTTTTGGAGCACGGAAAGACGATG
ACGGAAAAAGAGATCGTGGATTACGTCGCCAGTCAAGTAACAACCGCGAAAAAGTTGCG
CGGAGGAGTTGTGTTTGTGGACGAAGTACCGAAAGGTCTTACCGGAAAACTCGACGCAA
GAAAAATCAGAGAGATCCTCATAAAGGCCAAGAAGGGCGGAAAGATCGCCGTGGGAGG
TGGCTCATCTGGCGGAGGTCAGATCTCGTACGCGTCCCGGGCGGAGTGCAGGTGGA
AACCATCTCCCCAGGAGACGGGCGCACCTTCCCCAAGCGCGCCAGACCTGCGTGGTG
CACTACACCGGGATGCTTGAAGATGGAAGAAATTTGATTCCTCCCGGGACAGAAACAA
GCCCTTTAAGTTTATGCTAGGCAAGCAGGAGGTGATCCGAGGCTGGGAAGAAGGGGTT
GCCCAGATGAGTGTGGGTCAGAGAGCCAAACTGACTATATCTCCAGATTATGCCTATGG
TGCCACTGGGCACCCAGGCATCATCCCACCACATGCCACTCTCGTCTTCGATGTGGAGC
TTCTAAAACTGGAAtgaACTAGTTAGTAAGCTTCTGCAGAAGGGCAATTCTGCAGATATCC
AGCACAGTGGCGGCCGCTCGAGTCTAGAGGGCCCGCGGTTCGAAGGTAAGCCTATCCC
TAACCCTCTCCTCGGTCTCGATTCTACGCGTACCGGTCATCATCACCATCACCATTGAGT
TTAAACCCGCTGATCAGCCTCGACTGTGCCTTCTAGTTGCCAGCCATCTGTTGTTTGCC
CCTCCCCCGTGCCTTCCTTGACCCTGGAAGGTGCCACTCCCACTGTCCTTTCCTAATAA
AATGAGGAAATTGCATCGCATTGTCTGAGTAGGTGTCATTCTATTCTGGGGGGTGGGGT
GGGGCAGGACAGCAAGGGGGAGGATTGGGAAGACAATAGCAGGCATGCTGGGGATGC
GGTGGGCTCTATGGCTTCTGAGGCGGAAAGAACCAGCTGGGGCTCTAGGGGGTATCCC
CACGCGCCCTGTAGCGGCGCATTAAGCGCGGCGGGTGTGGTGGTTACGCGCAGCGTG
```

-continued

```
ACCGCTACACTTGCCAGCGCCCTAGCGCCCGCTCCTTTCGCTTTCTTCCCTTCCTTTCT
CGCCACGTTCGCCGGCTTTCCCCGTCAAGCTCTAAATCGGGGCATCCCTTTAGGGTTCC
GATTTAGTGCTTTACGGCACCTCGACCCCAAAAAACTTGATTAGGGTGATGGTTCACGTA
GTGGGCCATCGCCCTGATAGACGGTTTTTCGCCCTTTGACGTTGGAGTCCACGTTCTTT
AATAGTGGACTCTTGTTCCAAACTGGAACAACACTCAACCCTATCTCGGTCTATTCTTTT
GATTTATAAGGGATTTTGGGGATTTCGGCCTATTGGTTAAAAAATGAGCTGATTTAACAA
AAATTTAACGCGAATTAATTCTGTGGAATGTGTGTCAGTTAGGGTGTGGAAAGTCCCCAG
GCTCCCCAGGCAGGCAGAAGTATGCAAAGCATGCATCTCAATTAGTCAGCAACCAGGTG
TGGAAAGTCCCCAGGCTCCCCAGCAGGCAGAAGTATGCAAAGCATGCATCTCAATTAGT
CAGCAACCATAGTCCCGCCCCTAACTCCGCCCATCCCGCCCCTAACTCCGCCCAGTTCC
GCCCATTCTCCGCCCCATGGCTGACTAATTTTTTTATTTATGCAGAGGCCGAGGCCGC
CTCTGCCTCTGAGCTATTCCAGAAGTAGTGAGGAGGCTTTTTTGGAGGCCTAGGCTTTT
GCAAAAAGCTCCCGGGAGCTTGTATATCCATTTTCGGATCTGATCAGCACGTGTTGACAA
TTAATCATCGGCATAGTATATCGGCATAGTATAATACGACAAGGTGAGGAACTAAACCAT
GGCCAAGCCTTTGTCTCAAGAAGAATCCACCCTCATTGAAAGAGCAACGGCTACAATCAA
CAGCATCCCCATCTCTGAAGACTACAGCGTCGCCAGCGCAGCTCTCTCTAGCGACGGC
CGCATCTTCACTGGTGTCAATGTATATCATTTTACTGGGGGACCTTGTGCAGAACTCGTG
GTGCTGGGCACTGCTGCTGCTGCGGCAGCTGGCAACCTGACTTGTATCGTCGCGATCG
GAAATGAGAACAGGGGCATCTTGAGCCCCTGCGGACGGTGTCGACAGGTGCTTCTCGA
TCTGCATCCTGGGATCAAAGCGATAGTGAAGGACAGTGATGGACAGCCGACGGCAGTT
GGGATTCGTGAATTGCTGCCCTCTGGTTATGTGTGGGAGGGCTAAGCACTTCGTGGCC
GAGGAGCAGGACTGACACGTGCTACGAGATTTCGATTCCACCGCCGCCTTCTATGAAAG
GTTGGGCTTCGGAATCGTTTTCCGGGACGCCGGCTGGATGATCCTCCAGCGCGGGAT
CTCATGCTGGAGTTCTTCGCCCACCCCAACTTGTTTATTGCAGCTTATAATGGTTACAAA
TAAAGCAATAGCATCACAAATTTCACAAATAAAGCATTTTTTTCACTGCATTCTAGTTGTG
GTTTGTCCAAACTCATCAATGTATCTTATCATGTCTGTATACCGTCGACCTCTAGCTAGA
GCTTGGCGTAATCATGGTCATAGCTGTTTCCTGTGTGAAATTGTTATCCGCTCACAATTC
CACACAACATACGAGCCGGAAGCATAAAGTGTAAAGCCTGGGGTGCCTAATGAGTGAGC
TAACTCACATTAATTGCGTTGCGCTCACTGCCCGCTTTCCAGTCGGGAAACCTGTCGTG
CCAGCTGCATTAATGAATCGGCCAACGCGCGGGGAGAGGCGGTTTGCGTATTGGGCGC
TCTTCCGCTTCCTCGCTCACTGACTCGCTGCGCTCGGTCGTTCGGCTGCGGCGAGCGG
TATCAGCTCACTCAAAGGCGGTAATACGGTTATCCACAGAATCAGGGGATAACGCAGGA
AAGAACATGTGAGCAAAAGGCCAGCAAAAGGCCAGGAACCGTAAAAAGGCCGCGTTGCT
GGCGTTTTTCCATAGGCTCCGCCCCCCTGACGAGCATCACAAAAATCGACGCTCAAGTC
AGAGGTGGCGAAACCCGACAGGACTATAAAGATACCAGGCGTTTCCCCCTGGAAGCTC
CCTCGTGCGCTCTCCTGTTCCGACCCTGCCGCTTACCGGATACCTGTCCGCCTTTCTCC
CTTCGGGAAGCGTGGCGCTTTCTCAATGCTCACGCTGTAGGTATCTCAGTTCGGTGTAG
GTCGTTCGCTCCAAGCTGGGCTGTGTGCACGAACCCCCCGTTCAGCCCGACCGCTGCG
CCTTATCCGGTAACTATCGTCTTGAGTCCAACCCGGTAAGACACGACTTATCGCCACTG
GCAGCAGCCACTGGTAACAGGATTAGCAGAGCGAGGTATGTAGGCGGTGCTACAGAGT
```

-continued

```
TCTTGAAGTGGTGGCCTAACTACGGCTACACTAGAAGGACAGTATTTGGTATCTGCGCT

CTGCTGAAGCCAGTTACCTTCGGAAAAAGAGTTGGTAGCTCTTGATCCGGCAAACAAAC

CACCGCTGGTAGCGGTGGTTTTTTTGTTTGCAAGCAGCAGATTACGCGCAGAAAAAAG

GATCTCAAGAAGATCCTTTGATCTTTTCTACGGGGTCTGACGCTCAGTGGAACGAAAACT

CACGTTAAGGGATTTTGGTCATGAGATTATCAAAAAGGATCTTCACCTAGATCCTTTTAAA

TTAAAAATGAAGTTTTAAATCAATCTAAAGTATATATGAGTAAACTTGGTCTGACAGTTAC

CAATGCTTAATCAGTGAGGCACCTATCTCAGCGATCTGTCTATTTCGTTCATCCATAGTT

GCCTGACTCCCCGTCGTGTAGATAACTACGATACGGGAGGGCTTACCATCTGGCCCCA

GTGCTGCAATGATACCGCGAGACCCACGCTCACCGGCTCCAGATTTATCAGCAATAAAC

CAGCCAGCCGGAAGGGCCGAGCGCAGAAGTGGTCCTGCAACTTTATCCGCCTCCATCC

AGTCTATTAATTGTTGCCGGGAAGCTAGAGTAAGTAGTTCGCCAGTTAATAGTTTGCGCA

ACGTTGTTGCCATTGCTACAGGCATCGTGGTGTCACGCTCGTCGTTTGGTATGGCTTCA

TTCAGCTCCGGTTCCCAACGATCAAGGCGAGTTACATGATCCCCATGTTGTGCAAAAA

AGCGGTTAGCTCCTTCGGTCCTCCGATCGTTGTCAGAAGTAAGTTGGCCGCAGTGTTAT

CACTCATGGTTATGGCAGCACTGCATAATTCTCTTACTGTCATGCCATCCGTAAGATGCT

TTTCTGTGACTGGTGAGTACTCAACCAAGTCATTCTGAGAATAGTGTATGCGGCGACCG

AGTTGCTCTTGCCCGGCGTCAATACGGGATAATACCGCGCCACATAGCAGAACTTTAAA

AGTGCTCATCATTGGAAAACGTTCTTCGGGGCGAAAACTCTCAAGGATCTTACCGCTGTT

GAGATCCAGTTCGATGTAACCCACTCGTGCACCCAACTGATCTTCAGCATCTTTTACTTT

CACCAGCGTTTCTGGGTGAGCAAAAACAGGAAGGCAAATGCCGCAAAAAAGGGAATAA

GGGCGACACGGAAATGTTGAATACTCATACTCTTCCTTTTC
```

REFERENCES

1. Newton, A. (2003) Biochem J 370, 361-371.
2. Ogawa, H., Ishiguro, S., Gaubatz, S., Livingston, D. & Nakatani, Y. (2002) Science 296, 1132-1136.
3. Luo, J., Manning, B. & Cantley, L. (2003) Cancer Cell 4, 257-262.
4. Heldin, C. (2001) Stem Cells 19, 295-303.
5. Darnell, J. E., Jr. (2002) Nature Rev Cancer 2, 740-749.
6. Manning, G., Whyte, D., Martinez, R., Hunter, T. & Sudarsanam, S. (2002) Science 298, 1912-1934.
7. Luker, G., Sharma, V., Pica, C., Dahlheimer, J., Li, W., Ochesky, J., Ryan, C., Piwnica-Worms, H. & Piwnica-Worms, D. (2002) Proc Natl Acad Sci USA 99, 6961-6966.
8. Luker, G., Sharma, V. & Piwnica-Worms, D. (2003) Methods 29, 110-122.
9. Ray, P., Pimenta, H., Paulmurugan, R., Berger, F., Phelps, M., Iyer, M. & Gambhir, S. (2002) Proc Natl Acad Sci USA 99, 2105-3110.
10. Paulmurugan, R., Umezawa, Y. & Gambhir, S. S. (2002) Proc Natl Acad Sci USA 99, 15608-13.
11. Toby, G. & Golemis, E. (2001) Methods 24, 201-217.
12. Lievens, S., Heyden, J., Vertenten, E., Plum, J., Vandekerckhove, J. & Tavernier, J. (2004) Methods Mol Biol 263, 293-310.
13. Rossi, F., Charlton, C. & Blau, H. (1997) Proc Natl Acad Sci USA 94, 8405-8410.
14. Remy, I., Galarneau, A. & Michnick, S. W. (2002) Methods Mol Biol 185, 447-59.
15. Ozawa, T., Kaihara, A., Sato, M., Tachihara, K. & Umezawa (2001) Anal Chem 73, 2516-2521.
16. Paulmurugan, R. & Gambhir, S. (2003) Anal Chem 75, 1584-1589.
17. Pichler, A., Prior, J. & Piwnica-Worms, D. (2004) Proc Natl Acad Sci USA 101, 1702-1707.
18. Ostermeier, M., Nixon, A., Shim, J. & Benkovic, S. (1999) Proc Natl Acad Sci USA 96, 3562-3567.
19. Cebolla, A., Vazquez, M. & Palomares, A. (1995) Appl Environ Microbiol 61, 660-668.
20. Weber-Nordt, R., Riley, J., Greenlund, A., Moore, K., Darnell, J. & Schreiber, R. (1996) J Biol Chem 271, 27954-27961.
21. Graves, P., Yu, L., Schwarz, J., Gales, J., Sausville, E., O'Connor, P. & Piwnica-Worms, H. (2000) J Biol Chem 275, 5600-5605.
22. Harris, T. & Lawrence, J. (2003) Science STKE 212, rel5.
23. Sung, D. & Kang, H. (1998) Photochem Photobiol 68, 749-753.
24. Galarneau, A., Primeau, M., Trudeau, L.-E. & Michnick, S. (2002) Nat Biotechnol 20, 619-622.
25. Remy, I. & Michnick, S. (1999) Proc Natl Acad Sci USA 96, 5394-5399.
26. Chen, J., Zheng, X., Brown, E. & Schreiber, S. (1995) Proc Natl Acad Sci USA 92, 4947-4951.
27. Michnick, S. W. (2001) Curr Opin Struct Biol 11, 472-7.
28. Guba, M., von Breitenbuch, P., Steinbauer, M., Koehl, G., Flegel, S., Hornung, M., Bruns, C. J., Zuelke, C., Farkas, S., Anthuber, M., Jauch, K. W. & Geissler, E. K. (2002) Nat Med 8, 128-35.
29. Nilsson, I. & Hoffmann, I. (2000) Prog Cell Cycle Res 4, 107-114.

30. Peng, C., Graves, P., Thoma, R., Wu, Z., Shaw, A. & Piwnica-Worms, H. (1997) Science 277, 1501-1505.

31. Levy, D. E. & Darnell, J. E., Jr. (2002) Nat Rev Mol Cell Biol 3, 651-662.

32. Stancato, L. F., David, M., CarterSu, C., Larner, A. C. & Pratt, W. B. (1996) J Biol Chem 271, 4134-4137.

33. Braunstein, J., Brutsaert, S., Olson, R. & Schindler, C. (2003) J Biol Chem 278, 34133-34140.

34. Kretzschmar, A. K., Dinger, M. C., Henze, C., Brocke-Heidrich, K. & Horn, F. (2004) Biochem J 377, 289-297.

35. Ota, N., Brett, T. J., Murphy, T. L., Fremont, D. H. & Murphy, K. M. (2004) Nature Immunology 5, 208-215.

36. Mckendry, R., John, J., Flavell, D., Muller, M., Kerr, I. M. & Stark, G. R. (1991) Proc Natl Acad Sci USA 88, 11455-11459.

37. Shuai, K., Horvath, C. M., Huang, L. H. T., Qureshi, S. A., Cowburn, D. & Darnell, J. E. (1994) Cell 76, 821-828.

38. Conti, E., Franks, N. P. & Brick, P. (1996) Structure 4, 287-98.

Aronheim, A., Zandi, E., Hennemann, H., Elledge, S., and Karin, M. (1997). Isolation of an AP-1 repressor by a novel method for detecting protein-protein interactions. Molec Cell Biol 17, 3094-3102.

Boute, N., Jockers, R., and Issad, T. (2002). The use of resonance energy transfer in high-throughput screening: BRET versus FRET. Trends Pharmacol Sci 23, 351-354.

Broder, Y., Katz, S., and Aronheim, A. (1998). The Ras recruitment system, a novel approach to the study of protein-protein interactions. Current Biol 8, 1121-1124.

Chen, J., Zheng, X. F., Brown, E. J., and Schreiber, S. L. (1995). Identification of an 11-kDa FKBP12-rapamycin-binding domain within the 289-kDa FKBP12-rapamycin-associated protein and characterization of a critical serine residue. Proc Natl Acad Sci USA 92, 4947-4951.

Darnell, J. E., Jr. (2002). Transcription factors as targets for cancer therapy. Nature Rev Cancer 2, 740-749.

Eyckerman, S., Verhee, A., Van der Heyden, J., Lemmens, I., Van Ostade, X., Vandekerckhove, J., and Tavernier, J. (2001). Design and application of a cytokine-receptor-based interaction trap. Nat Cell Biol 3, 1114-1119.

Fields, S., and Song, O. (1989). A novel genetic system to detect protein-protein interaction. Nature 340, 245-246.

Galarneau, A., Primeau, M., Trudeau, L.-E., and Michnick, S. (2002). β-Lactamase protein fragment complementation assays as in vivo and in vitro sensors of protein-protein interactions. Nat Biotechnol 20, 619-622.

Gautier, I., Tranier, M., Durieux, C., Coppey, J., Pansu, R., Nicolas, J., Kernnitz, K., and Coppey-Moisan, M. (2001). Homo-FRET Microscopy in Living Cells to Measure Monomer-Dimer Transition of GFP-Tagged Proteins. Biophysical Journal 80, 3000-3008.

Heldin, C. (2001). Signal transduction: multiple pathways, multiple options for therapy. Stem Cells 19, 295-303.

Johnsson, N., and Varshavsky, A. (1994). Split ubiquitin as a sensor of protein interactions in vivo. Proc Natl Acad Sci USA 91, 10340-10344.

Luker, G., Sharma, V., Pica, C., Dahlheimer, J., Li, W., Ochesky, J., Ryan, C., Piwnica-Worms, H., and Piwnica-Worms, D. (2002). Noninvasive imaging of protein-protein interactions in living animals. Proc Natl Acad Sci USA 99, 6961-6966.

Luker, G., Sharma, V., Pica, C., Prior, J., Li, W., and Piwnica-Worms, D. (2003a). Molecular imaging of protein-protein Interactions: controlled expression of p53 and large T antigen fusion proteins in vivo. Cancer Res 63, 1780-1788.

Luker, G., Sharma, V., and Piwnica-Worms, D. (2003b). Noninvasive imaging of protein-protein interactions in living animals. Handbook of Proteomic Methods, P.M. Conn (Ed.), Humana Press, Inc., Totowa, N.J. pp. 283-298.

Luker, G., Sharma, V., and Piwnica-Worms, D. (2003c). Visualizing protein-protein interactions in living animals. Methods 29, 110-122.

Ogawa, H., Ishiguro, S., Gaubatz, S., Livingston, D., and Nakatani, Y. (2002). A complex with chromatin modifiers that occupies E2F- and Myc-responsive genes in G0 cells. Science 296, 1132-1136.

Ostermeier, M., Nixon, A., Shim, J., and Benkovic, S. (1999). Combinatorial protein engineering by incremental truncation. Proc Natl Acad Sci USA 96, 3562-3567.

Ozawa, T., Kaihara, A., Sato, M., Tachihara, K., and Umezawa. (2001). Split luciferase as an optical probe for detecting protein-protein interactions in mammalian cells based on protein splicing. Anal Chem 73, 2516-2521.

Paulmurugan, R., and Gambhir, S. (2003). Monitoring protein-protein interactions using split synthetic Renilla luciferase protein-fragment-assisted complementation. Anal Chem 75, 1584-1589.

Paulmurugan, R., Umezawa, Y., and Gambhir, S. S. (2002). Noninvasive imaging of protein-protein interactions in living subjects by using reporter protein complementation and reconstitution strategies. Proc Natl Acad Sci USA 99, 15608-15613.

Ray, P., Pimenta, H., Paulmurugan, R., Berger, F., Phelps, M., Iyer, M., and Gambhir, S. (2002). Noninvasive quantitative imaging of protein-protein interactions in living subjects. Proc Natl Acad Sci USA 99, 2105-3110.

Remy, I., and Michnick, S. (1999). Clonal selection and in vivo quantitation of protein interactions with protein-fragment complementation assays. Proc Natl Acad Sci USA 96, 5394-5399.

Remy, I., Wilson, I., and Michnick, S. (1999). Erythropoietin receptor activation by a ligand-induced conformation change. Science 283, 990-993.

Rossi, F., Blakely, B., and Blau, H. (2000). Interaction blues: protein interactions monitored in live mammalian cells by beta-galactosidase complementation. Trends Cell Biol 10, 119-122.

Rossi, F., Charlton, C., and Blau, H. (1997). Monitoring protein-protein interactions in intact eukaryotic cells by beta-galactosidase complementation. Proc Natl Acad Sci USA 94, 8405-8410.

Stagljar, I., Korostensky, C., Johnsson, N., and te Heesen, S. (1998). A genetic system based on split-ubiquitin for the analysis of interactions between membrane proteins in vivo. Proc Natl Acad Sci USA 95, 5187-5192.

Stark, G., Kerr, I., Williams, B., Silverman, R., and Schreiber, R. (1998). How cells respond to interferons. Annu Rev Biochem 67, 227-264.

Toby, G., and Golemis, E. (2001). Using the yeast interaction trap and other two-hybrid-based approaches to study protein-protein interactions. Methods 24, 201-217.

von Mering, C., Krause, R., Snel, B., Cornell, M., Oliver, S., Fields, S., and Bork, P. (2002). Comparative assessment of large-scale sets of protein-protein interactions. Nature 471, 399-403.

Wehrman, T., Kleaveland, B., Her, J. H., Balint, R. F., and Blau, H. M. (2002). Protein-protein interactions monitored in mammalian cells via complementation of beta-lactamase enzyme fragments. Proc Natl Acad Sci USA 99, 3469-3474.

Zhang, H., Hu, G., Wang, H., Sciavolino, P., Iler, N Shen, M., and Abate-Shen, C. (1997). Heterodimerization of Msx and Dlx homeoproteins results in functional antagonism. Mol Cell Biol 17, 2920-2932.

What is claimed is:

1. An isolated, characterized and functional complementation system comprising a pair of fusion proteins, each protein fused to one luciferase fragment of a pair of firefly luciferase fragments, the pair commonly having a background bioluminescence when in proximity to a protein fused to the other respective luciferase fragment of the pair such that reconstitution of the pair provides a bioluminescent emitting moiety, wherein the protein pair comprises a polypeptide encoded by SEQ. ID. NO. 1 and a polypeptide encoded by SEQ. ID. NO. 2.

2. A system in accordance with claim 1 wherein the complementation system has capable analytical means associated therewith to capably and faithfully detect bioluminescence.

3. A system in accordance with claim 1 wherein the constitutive activity of the N-terminus fragment is nil.

4. A system in accordance with claim 1 wherein the system is small molecule inducible.

5. A system in accordance with claim 2 wherein the complementation system further comprises a means for monitoring the bioluminescence of a sample of live cells.

6. A system in accordance with claim 2 wherein the functional analytical means comprise means sufficient to determine changes in bioluminescence upon addition of a small molecule to the system.

7. A plasmid comprising at least one of a DNA sequence and an RNA sequence that encodes the pair of fusion proteins in accordance with claim 1.

* * * * *

SEQUENCE LISTING

<160> NUMBER OF SEQ ID NOS: 4

<210> SEQ ID NO 1
<211> LENGTH: 7145
<212> TYPE: DNA
<213> ORGANISM: Artificial Sequence
<220> FEATURE:
<223> OTHER INFORMATION: Description of Artificial Sequence: Synthetic polynucleotide construct FRB-NLuc

<400> SEQUENCE: 1

```
gacggatcgg gagatctccc gatcccctat ggtcgactct cagtacaatc tgctctgatg      60
ccgcatagtt aagccagtat ctgctccctg cttgtgtgtt ggaggtcgct gagtagtgcg     120
cgagcaaaat ttaagctaca caaggcaag gcttgaccga caattgcatg aagaatctgc     180
ttagggttag gcgttttgcg ctgcttcgcg atgtacgggc cagatatacg cgttgacatt     240
gattattgac tagttattaa tagtaatcaa ttacggggtc attagttcat agcccatata     300
tggagttccg cgttacataa cttacggtaa atggcccgcc tggctgaccg cccaacgacc     360
cccgcccatt gacgtcaata atgacgtatg ttcccatagt aacgccaata gggactttcc     420
attgacgtca atgggtggac tatttacggt aaactgccca cttggcagta catcaagtgt     480
atcatatgcc aagtacgccc cctattgacg tcaatgacgg taaatggccc gcctggcatt     540
atgcccagta catgacctta tgggactttc ctacttggca gtacatctac gtattagtca     600
tcgctattac catggtgatg cggttttggc agtacatcaa tgggcgtgga tagcggtttg     660
actcacgggg atttccaagt ctccacccca ttgacgtcaa tgggagtttg ttttggcacc     720
aaaatcaacg ggactttcca aaatgtcgta caactccgc cccattgacg caaatgggcg     780
gtaggcgtgt acggtgggag gtctatataa gcagagctct ctggctaact agagaaccca     840
ctgcttactg gcttatcgaa attaatacga ctcactatag ggagacccaa gctggctagt     900
taagcttggt accgagctcg gatccactag tccagtgtgg tggaattgcc cttacaccac     960
catggagatg tggcatgaag gcctggaaga ggcatctcgt ttgtactttg ggaaaggaa    1020
cgtgaaaggc atgtttgagg tgctggagcc cttgcatgct atgatggaac ggggccccca    1080
gactctgaag gaaacatcct ttaatcaggc ctatggtcga gatttaatgg aggcccaaga    1140
gtggtgcagg aagtacatga atcagggaa tgtcaaggac ctcacccaag cctgggacct    1200
ctattatcat gtgttccgac gaatctcaaa gcagcagatc tcgtacgcgt cccggggcgg    1260
tggctcatct ggcggaggtg aagacgccaa aaacataaag aaaggcccgg cgccattcta    1320
tccgctggaa gatggaaccg ctggagagca actgcataag gctatgaaga gatacgccct    1380
ggttcctgga acaattgctt ttacagatgc acatatcgag gtggacatca cttacgctga    1440
gtacttcgaa atgtccgttc ggttggcaga agctatgaaa cgatatgggc tgaatacaaa    1500
tcacagaatc gtcgtatgca gtgaaaactc tcttcaattc tttatgccgg tgttgggcgc    1560
gttatttatc ggagttgcag ttgcgcccgc gaacgacatt tataatgaac gtgaattgct    1620
caacagtatg ggcatttcgc agcctaccgt ggtgttcgtt tccaaaaagg ggttgcaaaa    1680
aattttgaac gtgcaaaaaa agctcccaat catccaaaaa attattatca tggattctaa    1740
aacggattac cagggatttc agtcgatgta cacgttcgtc acatctcatc tacctcccgg    1800
ttttaatgaa tacgattttg tgccagagtc cttcgatagg gacaagacaa ttgcactgat    1860
catgaactcc tctggatcta ctggtctgcc taaaggtgtc gctctgcctc atagaactgc    1920
```

```
ctgcgtgaga ttctcgcatg ccagagatcc tattttttggc aatcaaatca ttccggatac   1980
tgcgatttta agtgttgttc cattccatca cggtttttga atgtttacta cactcggata   2040
tttgatatgt ggatttcgag tcgtcttaat gtatagattt gaagaagagc tgtttctgag   2100
gagccttcag gattacaaga ttcaaagtgc gctgctggtg ccaaccctat tctccttctt   2160
cgccaaaagc actctgattg acaaatacga tttatctaat ttacacgaaa ttgcttctgg   2220
tggcgctccc ctctctaagg aagtcgggga agcggttgcc aagaggttcc atctgccagg   2280
tatcaggcaa ggatatgggc tcactgagac tacatcagct attctgatta cacccgaggg   2340
ggatgataaa ccgggcgcgg tcggtaaagt tgttccattt tttgaagcga aggttgtgga   2400
tctggatacc gggaaaacgc tgggcgttaa tcaaagaggc gaactgtgtg tgagaggtcc   2460
tatgattatg tccggttatg taaacaatcc ggaagcgacc aacgccttga ttgacaagga   2520
tggatgataa cattctggta gctaggtaat gcataactag ctaaggtacc caattaaggg   2580
caattctgca gatatccagc acagtggcgg ccgctcgagt ctagagggcc cgcggttcga   2640
aggtaagcct atccctaacc ctctcctcgg tctcgattct acgcgtaccg gtcatcatca   2700
ccatcaccat tgagtttaaa cccgctgatc agcctcgact gtgccttcta gttgccagcc   2760
atctgttgtt tgcccctccc ccgtgccttc cttgaccctg gaaggtgcca ctcccactgt   2820
cctttcctaa taaaatgagg aaattgcatc gcattgtctg agtaggtgtc attctattct   2880
ggggggtggg gtggggcagg acagcaaggg ggaggattgg gaagacaata gcaggcatgc   2940
tggggatgcg gtgggctcta tggcttctga ggcggaaaga accagctggg gctctagggg   3000
gtatccccac gcgccctgta gcggcgcatt aagcgcggcg ggtgtggtgg ttacgcgcag   3060
cgtgaccgct acacttgcca gcgccctagc gcccgctcct ttcgctttct tcccttcctt   3120
tctcgccacg ttcgccggct ttccccgtca agctctaaat cggggcatcc ctttagggtt   3180
ccgatttagt gctttacggc acctcgaccc caaaaaactt gattagggtg atggttcacg   3240
tagtgggcca tcgccctgat agacggtttt tcgccctttg acgttggagt ccacgttctt   3300
taatagtgga ctcttgttcc aaactggaac aacactcaac cctatctcgg tctattcttt   3360
tgatttataa gggattttgg ggatttcggc ctattggtta aaaaatgagc tgatttaaca   3420
aaaatttaac gcgaattaat tctgtggaat gtgtgtcagt tagggtgtgg aaagtcccca   3480
ggctccccag gcaggcagaa gtatgcaaag catgcatctc aattagtcag caaccaggtg   3540
tggaaagtcc ccaggctccc cagcaggcag aagtatgcaa agcatgcatc tcaattagtc   3600
agcaaccata gtcccgcccc taactccgcc catcccgccc taactccgcc cagttccgc   3660 ccattctccg ccccatggct gactaatttt ttttatttat gcagaggccg aggccgcctc   3720
tgcctctgag ctattccaga agtagtgagg aggcttttt ggaggcctag cttttgcaa   3780 aaagctcccg ggagcttgta tatccatttt cggatctgat caagagacag gatgaggatc   3840
gtttcgcatg attgaacaag atggattgca cgcaggttct ccggccgctt gggtggagag   3900
gctattcggc tatgactggg cacaacagac aatcggctgc tctgatgccg ccgtgttccg   3960
gctgtcagcg caggggcgcc cggttctttt tgtcaagacc gacctgtccg gtgccctgaa   4020
tgaactgcag gacgaggcag cgcggctatc gtggctggcc acgacgggcg ttccttgcgc   4080
agctgtgctc gacgttgtca ctgaagcggg aagggactgg ctgctattgg gcgaagtgcc   4140
ggggcaggat ctcctgtcat ctcaccttgc tcctgccgag aaagtatcca tcatggctga   4200
tgcaatgcgg cggctgcata cgcttgatcc ggctacctgc ccattcgacc accaagcgaa   4260
acatcgcatc gagcgagcac gtactcggat ggaagccggt cttgtcgatc aggatgatct   4320
```

```
ggacgaagag catcaggggc tcgcgccagc cgaactgttc gccaggctca aggcgcgcat    4380
gcccgacggc gaggatctcg tcgtgaccca tggcgatgcc tgcttgccga atatcatggt    4440
ggaaaatggc cgcttttctg gattcatcga ctgtggccgg ctgggtgtgg cggaccgcta    4500
tcaggacata gcgttggcta cccgtgatat tgctgaagag cttggcggcg aatgggctga    4560
ccgcttcctc gtgctttacg gtatcgccgc tcccgattcg cagcgcatcg ccttctatcg    4620
ccttcttgac gagttcttct gagcgggact ctggggttcg cgaaatgacc gaccaagcga    4680
cgcccaacct gccatcacga gatttcgatt ccaccgccgc cttctatgaa aggttgggct    4740
tcggaatcgt tttccgggac gccggctgga tgatcctcca gcgcgggat ctcatgctgg     4800 agttcttcgc ccaccccaac ttgtttattg cagcttataa tggttacaaa taaagcaata    4860
gcatcacaaa tttcacaaat aaagcatttt tttcactgca ttctagttgt ggtttgtcca    4920
aactcatcaa tgtatcttat catgtctgta taccgtcgac ctctagctag agcttggcgt    4980
aatcatggtc atagctgttt cctgtgtgaa attgttatcc gctcacaatt ccacacaaca    5040
tacgagccgg aagcataaag tgtaaagcct ggggtgccta atgagtgagc taactcacat    5100
taattgcgtt gcgctcactg cccgctttcc agtcgggaaa cctgtcgtgc cagctgcatt    5160
aatgaatcgg ccaacgcgcg gggagaggcg gtttgcgtat tggcgctct ccgcttcct     5220 cgctcactga ctcgctgcgc tcggtcgttc ggctgcggcg agcggtatca gctcactcaa    5280
aggcggtaat acggttatcc acagaatcag gggataacgc aggaaagaac atgtgagcaa    5340
aaggccagca aaaggccagg aaccgtaaaa aggccgcgtt gctggcgttt ttccataggc    5400
tccgcccccc tgacgagcat cacaaaaatc gacgctcaag tcagaggtgg cgaaacccga    5460
caggactata aagataccag gcgtttcccc ctggaagctc cctcgtgcgc tctcctgttc    5520
cgaccctgcc gcttaccgga tacctgtccg cctttctccc ttcgggaagc gtggcgcttt    5580
ctcaatgctc acgctgtagg tatctcagtt cggtgtaggt cgttcgctcc aagctgggct    5640
gtgtgcacga accccccgtt cagcccgacc gctgcgcctt atccggtaac tatcgtcttg    5700
agtccaaccc ggtaagacac gacttatcgc cactggcagc agccactggt aacaggatta    5760
gcagagcgag gtatgtaggc ggtgctacag agttcttgaa gtggtggcct aactacggct    5820
acactagaag gacagtattt ggtatctgcg ctctgctgaa gccagttacc ttcggaaaaa    5880
gagttggtag ctcttgatcc ggcaaacaaa ccaccgctgg tagcggtggt ttttttgttt    5940
gcaagcagca gattacgcgc agaaaaaaag gatctcaaga agatcctttg atcttttcta    6000
cggggtctga cgctcagtgg aacgaaaact cacgttaagg gattttggtc atgagattat    6060
caaaaaggat cttcacctag atccttttaa attaaaaatg aagttttaaa tcaatctaaa    6120
gtatatatga gtaaacttgg tctgacagtt accaatgctt aatcagtgag gcacctatct    6180
cagcgatctg tctatttcgt tcatccatag ttgcctgact ccccgtcgtg tagataacta    6240
cgatacggga gggcttacca tctggcccca gtgctgcaat gataccgcga gacccacgct    6300
caccggctcc agatttatca gcaataaacc agccagccgg aagggccgag cgcagaagtg    6360
gtcctgcaac tttatccgcc tccatccagt ctattaattg ttgccgggaa gctagagtaa    6420
gtagttcgcc agttaatagt ttgcgcaacg ttgttgccat tgctacaggc atcgtggtgt    6480
cacgctcgtc gtttggtatg gcttcattca gctccggttc ccaacgatca aggcgagtta    6540
catgatcccc catgttgtgc aaaaaagcgg ttagctcctt cggtcctccg atcgttgtca    6600
gaagtaagtt ggccgcagtg ttatcactca tggttatggc agcactgcat aattctctta    6660
```

```
ctgtcatgcc atccgtaaga tgcttttctg tgactggtga gtactcaacc aagtcattct    6720
gagaatagtg tatgcggcga ccgagttgct cttgcccggc gtcaatacgg gataataccg    6780
cgccacatag cagaacttta aaagtgctca tcattggaaa acgttcttcg gggcgaaaac    6840
tctcaaggat cttaccgctg ttgagatcca gttcgatgta acccactcgt gcacccaact    6900
gatcttcagc atcttttact ttcaccagcg tttctgggtg agcaaaaaca ggaaggcaaa    6960
atgccgcaaa aaagggaata agggcgacac ggaaatgttg aatactcata ctcttccttt    7020
ttcaatatta ttgaagcatt tatcagggtt attgtctcat gagcggatac atatttgaat    7080
gtatttagaa aaataaacaa ataggggttc cgcgcacatt tccccgaaaa gtgccacctg    7140
acgtc                                                                7145
```

<210> SEQ ID NO 2
<211> LENGTH: 6702
<212> TYPE: DNA
<213> ORGANISM: Artificial Sequence
<220> FEATURE:
<223> OTHER INFORMATION: Description of Artificial Sequence: Synthetic
    polynucleotide construct CLuc-FKBP

<400> SEQUENCE: 2

```
aatattattg aagcatttat cagggttatt gtctcatgag cggatacata tttgaatgta      60
tttagaaaaa taaacaaata ggggttccgc gcacatttcc ccgaaaagtg ccacctgacg     120
tcgacggatc gggagatctc ccgatcccct atggtcgact ctcagtacaa tctgctctga    180
tgccgcatag ttaagccagt atctgctccc tgcttgtgtg ttggaggtcg ctgagtagtg    240
cgcgagcaaa atttaagcta caacaaggca aggcttgacc gacaattgca tgaagaatct    300
gcttagggtt aggcgttttg cgctgcttcg cgatgtacgg gccagatata cgcgttgaca    360
ttgattattg actagccttt tgcaaaaagc tttgcaaaga tggataaagt tttaaacaga    420
gaggaatctt tgcagctaat ggaccttcta ggtcttgaaa ggagtgcctc gtgaggctcc    480
ggtgcccgtc agtgggcaga gcgcacatcg cccacagtcc ccgagaagtt ggggggaggg    540
gtcggcaatt gaaccggtgc ctagagaagg tggcgcgggg taaactggga aagtgatgtc    600
gtgtactggc tccgcctttt tcccgagggt gggggagaac cgtatataag tgcagtagtc    660
gccgtgaacg ttctttttcg caacgggttt gccgccagaa cacaggtaag tgccgtgtgt    720
ggttcccgcg ggcctggcct ctttacgggt tatggccctt gcgtgccttg aattacttcc    780
acctggctgc agtacgtgat tcttgatccc gagcttcggg ttggaagtgg gtgggagagt    840
tcgaggcctt gcgcttaagg agccccttcg cctcgtgctt gagttgaggc ctggcctggg    900
cgctggggcc gccgcgtgcg aatctggtgg caccttcgcg cctgtctcgc tgctttcgat    960
aagtctctag ccatttaaaa ttttgatga cctgctgcga cgctttttt ctggcaagat    1020 agtcttgtaa atgcgggcca agatctgcac actggtattt cggtttttgg ggccgcgggc    1080
ggcgacgggg cccgtgcgtc ccagcgcaca tgttcggcga ggcggggcct gcgagcgcgg    1140
ccaccgagaa tcggacgggg gtagtctcaa gctggccggc ctgctctggt gcctggcctc    1200
gcgccgccgt gtatcgcccc gccctgggcg gcaaggctgg cccggtcggc accagttgcg    1260
tgagcggaaa gatggccgct tcccggccct gctgcaggga gctcaaaatg gaggacgcgg    1320
cgctcgggag agcgggcggg tgagtcaccc acacaaagga aaagggcctt tccgtcctca    1380
gccgtcgctt catgtgactc cacggagtac cggcgccgt ccaggcacct cgattagttc    1440
tcgagctttt ggagtacgtc gtctttaggt tggggggagg ggttttatgc gatggagttt    1500
```

-continued

```
ccccacactg agtgggtgga gactgaagtt aggccagctt ggcacttgat gtaattctcc    1560
ttggaatttg ccctttttga gtttggatct tggttcattc tcaagcctca gacagtggtt    1620
caaagttttt ttcttccatt tcaggtgtcg tgaggaatta gcttggtact aatacgactc    1680
actataggga gacccaagct ggctaggtaa gcttggtacc gagctcggat ccactagtcc    1740
agtgtggtgg aattgccctt acaccaccat gtccggttat gtaaacaatc cggaagcgac    1800
caacgccttg attgacaagg atggatggct acattctgga acatagctt actgggacga     1860
agacgaacac ttcttcatcg ttgaccgcct gaagtctctg attaagtaca aaggctatca    1920
ggtggctccc gctgaattgg aatccatctt gctccaacac cccaacatct tcgacgcagg    1980
tgtcgcaggt cttcccgacg atgacgccgg tgaacttccc gccgccgttg ttgttttgga    2040
gcacggaaag acgatgacgg aaaaagagat cgtggattac gtcgccagtc aagtaacaac    2100
cgcgaaaaag ttgcgcggag gagttgtgtt tgtggacgaa gtaccgaaag gtcttaccgg    2160
aaaactcgac gcaagaaaaa tcagagagat cctcataaag gccaagaagg gcggaaagat    2220
cgccgtggga ggtggctcat ctggcggagg tcagatctcg tacgcgtccc ggggcggagt    2280
gcaggtggaa accatctccc caggagacgg gcgcaccttc cccaagcgcg ccagacctg     2340
cgtggtgcac tacaccggga tgcttgaaga tggaaagaaa tttgattcct cccgggacag    2400
aaacaagccc tttaagttta tgctaggcaa gcaggaggtg atccgaggct gggaagaagg    2460
ggttgcccag atgagtgtgg gtcagagagc caaactgact atatctccag attatgccta    2520
tggtgccact gggcacccag gcatcatccc accacatgcc actctcgtct tcgatgtgga    2580
gcttctaaaa ctgaatgaa ctagttagta agcttctgca aagggcaat tctgcagata      2640
tccagcacag tggcggccgc tcgagtctag agggcccgcg gttcgaaggt aagcctatcc    2700
ctaaccctct cctcggtctc gattctacgc gtaccggtca tcatcaccat caccattgag    2760
tttaaacccg ctgatcagcc tcgactgtgc cttctagttg ccagccatct gttgtttgcc    2820
cctcccccgt gccttccttg accctggaag gtgccactcc cactgtcctt tcctaataaa    2880
atgaggaaat tgcatcgcat tgtctgagta ggtgtcattc tattctgggg ggtggggtgg    2940
ggcaggacag caaggggag gattgggaag acaatagcag gcatgctggg gatgcggtgg     3000
gctctatggc ttctgaggcg gaaagaacca gctgggctc tagggggtat ccccacgcgc     3060
cctgtagcgg cgcattaagc gcggcgggtg tggtggttac gcgcagcgtg accgctacac    3120
ttgccagcgc cctagcgccc gctcctttcg ctttcttccc ttcctttctc gccacgttcg    3180
ccggctttcc ccgtcaagct ctaaatcggg gcatcccttt agggttccga tttagtgctt    3240
tacggcacct cgaccccaaa aaacttgatt agggtgatgg ttcacgtagt gggccatcgc    3300
cctgatagac ggttttcgc cctttgacgt tggagtccac gttctttaat agtggactct    3360
tgttccaaac tggaacaaca ctcaaccccta tctcggtcta ttcttttgat ttataaggga    3420
ttttgggat tcggcctat tggttaaaaa atgagctgat ttaacaaaaa tttaacgcga      3480
attaattctg tggaatgtgt gtcagttagg gtgtggaaag tccccaggct ccccaggcag    3540
gcagaagtat gcaaagcatg catctcaatt agtcagcaac caggtgtgga aagtcccag     3600
gctccccagc aggcagaagt atgcaaagca tgcatctcaa ttagtcagca accatagtcc    3660
cgcccctaac tccgcccatc ccgcccctaa ctccgcccag ttccgcccat tctccgcccc    3720
atggctgact aatttttttt atttatgcag aggccgaggc cgcctctgcc tctgagctat    3780
tccagaagta gtgaggaggc ttttttggag gcctaggctt ttgcaaaaag ctcccggga     3840
cttgtatatc cattttcgga tctgatcagc acgtgttgac aattaatcat cggcatagta    3900
```

```
tatcggcata gtataatacg acaaggtgag gaactaaacc atggccaagc ctttgtctca   3960
agaagaatcc accctcattg aaagagcaac ggctacaatc aacagcatcc ccatctctga   4020
agactacagc gtcgccagcg cagctctctc tagcgacggc cgcatcttca ctggtgtcaa   4080
tgtatatcat tttactgggg gaccttgtgc agaactcgtg gtgctgggca ctgctgctgc   4140
tgcggcagct ggcaacctga cttgtatcgt cgcgatcgga aatgagaaca ggggcatctt   4200
gagcccctgc ggacggtgtc gacaggtgct tctcgatctg catcctggga tcaaagcgat   4260
agtgaaggac agtgatggac agccgacggc agttgggatt cgtgaattgc tgccctctgg   4320
ttatgtgtgg gagggctaag cacttcgtgg ccgaggagca ggactgacac gtgctacgag   4380
atttcgattc caccgccgcc ttctatgaaa ggttgggctt cggaatcgtt ttccgggacg   4440
ccggctggat gatcctccag cgcggggatc tcatgctgga gttcttcgcc caccccaact   4500
tgtttattgc agcttataat ggttacaaat aaagcaatag catcacaaat ttcacaaata   4560
aagcattttt ttcactgcat tctagttgtg gtttgtccaa actcatcaat gtatcttatc   4620
atgtctgtat accgtcgacc tctagctaga gcttggcgta atcatggtca tagctgtttc   4680
ctgtgtgaaa ttgttatccg ctcacaattc cacacaacat acgagccgga agcataaagt   4740
gtaaagcctg gggtgcctaa tgagtgagct aactcacatt aattgcgttg cgctcactgc   4800
ccgctttcca gtcgggaaac ctgtcgtgcc agctgcatta atgaatcggc caacgcgcgg   4860
ggagaggcgg tttgcgtatt gggcgctctt ccgcttcctc gctcactgac tcgctgcgct   4920
cggtcgttcg gctgcggcga gcggtatcag ctcactcaaa ggcggtaata cggttatcca   4980
cagaatcagg ggataacgca ggaaagaaca tgtgagcaaa aggccagcaa aaggccagga   5040
accgtaaaaa ggccgcgttg ctggcgtttt tccataggct ccgcccccct gacgagcatc   5100
acaaaaatcg acgctcaagt cagaggtggc gaaacccgac aggactataa agataccagg   5160
cgtttccccc tggaagctcc ctcgtgcgct ctcctgttcc gaccctgccg cttaccggat   5220
acctgtccgc ctttctccct tcgggaagcg tggcgctttc tcaatgctca cgctgtaggt   5280
atctcagttc ggtgtaggtc gttcgctcca agctgggctg tgtgcacgaa ccccccgttc   5340
agcccgaccg ctgcgcctta tccggtaact atcgtcttga gtccaacccg gtaagacacg   5400
acttatcgcc actggcagca gccactggta acaggattag cagagcgagg tatgtaggcg   5460
gtgctacaga gttcttgaag tggtggccta actacggcta cactagaagg acagtatttg   5520
gtatctgcgc tctgctgaag ccagttacct tcggaaaaag agttggtagc tcttgatccg   5580
gcaaacaaac caccgctggt agcggtggtt tttttgtttg caagcagcag attacgcgca   5640
gaaaaaaagg atctcaagaa gatcctttga tcttttctac ggggtctgac gctcagtgga   5700
acgaaaactc acgttaaggg attttggtca tgagattatc aaaaaggatc ttcacctaga   5760
tccttttaaa ttaaaaatga agttttaaat caatctaaag tatatatgag taaacttggt   5820
ctgacagtta ccaatgctta atcagtgagg cacctatctc agcgatctgt ctatttcgtt   5880
catccatagt tgcctgactc cccgtcgtgt agataactac gatacgggag ggcttaccat   5940
ctggccccag tgctgcaatg ataccgcgag acccacgctc accggctcca gatttatcag   6000
caataaacca gccagccgga agggccgagc gcagaagtgg tcctgcaact ttatccgcct   6060
ccatccagtc tattaattgt tgccgggaag ctagagtaag tagttcgcca gttaatagtt   6120
tgcgcaacgt tgttgccatt gctacaggca tcgtggtgtc acgctcgtcg tttggtatgg   6180
cttcattcag ctccggttcc caacgatcaa ggcgagttac atgatccccc atgttgtgca   6240
```

```
aaaaagcggt tagctccttc ggtcctccga tcgttgtcag aagtaagttg gccgcagtgt    6300
tatcactcat ggttatggca gcactgcata attctcttac tgtcatgcca tccgtaagat    6360
gcttttctgt gactggtgag tactcaacca agtcattctg agaatagtgt atgcggcgac    6420
cgagttgctc ttgcccggcg tcaatacggg ataataccgc gccacatagc agaactttaa    6480
aagtgctcat cattggaaaa cgttcttcgg ggcgaaaact ctcaaggatc ttaccgctgt    6540
tgagatccag ttcgatgtaa cccactcgtg cacccaactg atcttcagca tcttttactt    6600
tcaccagcgt ttctgggtga gcaaaaacag gaaggcaaaa tgccgcaaaa aagggaataa    6660
gggcgacacg gaaatgttga atactcatac tcttcctttt tc                      6702
```

<210> SEQ ID NO 3
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gln Ile Ser Tyr Ala Ser Arg Gly Gly Gly Ser Ser Gly Gly Gly
 1               5                  10                  15

<210> SEQ ID NO 4
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Gly Gly Ser Ser Gly Gly Gly Gln Ile Ser Tyr Ala Ser Arg Gly
 1               5                  10                  15